United States Patent
Chaudhuri et al.

(10) Patent No.: US 10,463,014 B2
(45) Date of Patent: *Nov. 5, 2019

(54) PEPPERS WITH UNIQUE AROMA AND TASTE

(71) Applicant: Seminis Vegetable Seeds, Inc., St. Louis, MO (US)

(72) Inventors: Swapan K. Chaudhuri, Sacramento, CA (US); Howard L. Constant, Sacramento, CA (US); Graeme S. Garvey, Woodland, CA (US); Brian J. Just, Fort Myers, FL (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/368,392

(22) Filed: Dec. 2, 2016

(65) Prior Publication Data

US 2017/0156279 A1 Jun. 8, 2017

Related U.S. Application Data

(60) Provisional application No. 62/261,951, filed on Dec. 2, 2015.

(51) Int. Cl.
| | | |
|---|---|---|
| *A01H 6/82* | (2018.01) | |
| *A01H 1/04* | (2006.01) | |
| *A01H 5/08* | (2018.01) | |
| *C12Q 1/68* | (2018.01) | |
| *C12Q 1/6895* | (2018.01) | |

(52) U.S. Cl.
CPC ............ *A01H 6/822* (2018.05); *A01H 1/04* (2013.01); *A01H 5/08* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,498,287 | B2 | 12/2002 | Nash |
| 8,420,905 | B2 * | 4/2013 | Leij .......................... A01H 5/08 435/430.1 |
| 8,471,113 | B2 | 6/2013 | McCarthy et al. |
| 8,536,419 | B2 * | 9/2013 | Lindeman ................ A01H 5/08 435/421 |
| 8,802,939 | B2 | 8/2014 | Phan et al. |
| 9,730,405 | B2 * | 8/2017 | Just .................... C12N 15/8286 |
| 2009/0064369 | A1 | 3/2009 | Berke |
| 2009/0255012 | A1 | 10/2009 | McCarthy |
| 2010/0058494 | A1 | 3/2010 | Phan et al. |
| 2012/0151616 | A1 | 6/2012 | McCarthy et al. |
| 2013/0145489 | A1 | 6/2013 | Gorguet et al. |
| 2014/0380516 | A1 | 12/2014 | Braun, III et al. |

OTHER PUBLICATIONS

Rodriguez-Burruezo et al. Journal of Agricultural and Food Chemistry 58(7): 4388-4400 (2010).*
Pino et al. Food Chemistry 125(3): 860-864 (Apr. 2011).*
1,4-cadinadiene Kovats Retention Index from www.pherobase.com accessed Jun. 2018.*
Moreno et al. Scientia Horticulturae 135: 87-97 (2012).*
Paran et al. Molecular Breeding 13: 251-261 (2004).*
Lefebvre et al. Genome 38: 112-121 (1995).*
Bernardo et al. Journal of Food Quality 31: 701-716 (2008).*
Eggink et al. Theoretical and Applied Genetics 127: 373-390 (2014).*
Arús et al., "Marker-assisted selection," In *Plant Breeding: Principles and Prospects*, Chapman and Hall: London, pp. 314-331 (1993).
Barrett et al., "Color, Flavor, Texture, and Nutritional Quality of Fresh-Cut Fruits and Vegetables: Desirable Levels, Instrumental and Sensory Measurement, and the Effects of Processing," *Critical Reviews in Food Science and Nutrition*, 50(5):369-389 (2010).
Camacho Villa et al., "Defining and identifying crop landraces," *Plant Genetic Resources*, 3(3):373-384 (2006).
Gaj et al., "ZFN, TALEN, and CRISPR/Cas-based methods for genome engineering," *Trends in Biotechnology*, 31:397-405 (2013).
Garces-Claver et al., "Determination of Capsaicin and Dihydrocapsaicin in Capsicum Fruit by Liquid Chromatography-Electrospray/Time-of-Flight Mass Spectrometry," *J. Agric. Food Chem.*, 54:9303-9311 (2006).
Hedrick, P.W., "Gametic Disequilibrium Measures: Proceed With Caution," *Genetics*, 117(2):331-341 (1987).
Bogusz Junior et al., "Analysis of the volatile compounds of Brazilian chilli peppers (*Capsicum* spp.) at two stages of maturity by solid phase micro-extraction and gas chromatography-mass spectrometry," *Food Research International*, 48:98-107 (2012).
Lander and Botstein, "Mapping Mendelian Factors Underlying Quantitative Traits Using RFLP Linkage Maps," *Genetics*, 121(1):185-199 (1989).
Openshaw et al., "Marker-assisted Selection in Backcross Breeding," In *Analysis of Molecular Marker Data*, pp. 41-43 (1994).
Ragot et al., "Marker-assisted backcrossing: a practical example," *Techniques et utilisations des marqueurs moléculaires*, 72:45-56 (1995).
Sung et al., "Capsaicin biosynthesis in water-stressed hot pepper fruits," *Bot. Bull. Acad. Sin.*, 46:35-42 (2005).

(Continued)

Primary Examiner — David T Fox
(74) *Attorney, Agent, or Firm* — Matthew L. Madsen; Arnold & Porter Kaye Scholer LLP

(57) ABSTRACT

This disclosure concerns the improvement of flavor in peppers by addition of aromas from other or the same pepper species. The disclosure describes novel *Capsicum* germplasm with aromatic components from *Capsicum chinense* and other horticultural traits from *Capsicum annuum*. The disclosure also describes a method for improving the flavor of a pepper through metabolomic-assisted selection to produce a pepper fruit with desirable aromas. The disclosure further provides multiple quantitative trait loci (QTLs), associated markers, and their use for genetic breeding of pepper plants with desired sweetness and flavor.

19 Claims, 4 Drawing Sheets

Specification includes a Sequence Listing.

(56) References Cited

OTHER PUBLICATIONS

Votava et al., "'NuMex Suave Red' and 'NuMex Suave Orange' Mild *Capsicum chinense* Cultivars," *HortScience*, 39(3):627-624 (2004).

Wahyuni, "Breeding for pepper fruit quality: A genetical metabolomics approach," Wageningen University, Chapter 1, p. 6 (2014).

"All about "Brix,"" Murray Family Farms, Bakersfield, California, https://www.murrayfamilyfarms.org/facts/brix.

Bogusz et al., "Analysis of the volatile compounds of Brazilian chilli peppers (*Capsicum* spp.) at two stages of maturity by solid phase micro-extraction and gas chromatography-mass spectrometry," *Food Research International*, 48(1):98-107 (2012).

Extended European Search Report dated Apr. 24, 2019, in European Patent Aplication No. 16871662.9.

Kleinhenz et al., "Using °Brix as an Indicator of Vegetable Quality: Linking Measured Values to Crop Management," The Ohio State University College of Food, Agricultural, and Environmental Sciences (2012) https://ohioline.osu.edu/factsheet/HYG-1651.

Kollmannsberger et al., "Comparative analysis of volatile compounds involved in the flavor of Capsicum annuum fruits," Progress in Research on Capsicum and Eggplant, Proceedings of the XIIIth Eucarpia Meeting, Warsaw, Poland, pp. 195-203 (2007).

"Sweet Pepper (in the polytunnel) Final Trials Report 2016," Final Report for Trial No. 1972—Royal Horticultural Society, pp. 1-22 (2016).

\* cited by examiner

Figure 1

| For fruits/cubes used | Retail Orange | Retail Yellow | SV2635PS |
|---|---|---|---|
| Puree of diced peppers | | | |
| - Brix | 9.0b | 8.8b | 10.3a |
| - TA | 3.1b | 2.8c | 4.1a |
| - Total Sugars (%) | 5.1b | 5.0b | 7.1a |
| | | | |
| - Aroma (Sum of volatiles 23 measured) | 344 | 206 | 260 |
| - Aroma (Chinense volatiles) | 0 | 0 | 0 |

US 10,463,014 B2

PEPPERS WITH UNIQUE AROMA AND TASTE

REFERENCE TO RELATED APPLICATION

This application claims the benefit of U.S. provisional application No. 62/261,951, filed on Dec. 2, 2015, which is herein incorporated by reference in its entirety.

INCORPORATION OF SEQUENCE LISTING

A computer readable form of the Sequence Listing is filed with this application by electronic submission and is incorporated into this application by reference in its entirety. The Sequence Listing is contained in the file created on Dec. 1, 2016, having the file name P34325US01 SEQ ID file_ST25.txt, and which is 24,618 bytes in size (as measured in the MS-Windows®).

FIELD

The present disclosure relates to and includes novel pepper plants and methods of their production. In particular the disclosure relates to the improvement of flavor in sweet peppers by addition of desirable aromas from other pepper species. The disclosure also describes metabolomics-assisted selection of pepper plants with desirable aromas or flavors.

BACKGROUND

Peppers are members of the Solanaceae family and the genus *Capsicum*, which includes species such as *C. annuum, C. baccatum, C. cardenasii, C. chacoense, C. chinense, C. ciliatum, C. eximium, C. flexuosum, C. frutescens, C. galapagoense, C. praetermissum, C. pubescens*, and *C. tovarii*. Peppers are cultivated and used around the world as sweet peppers, such as bell peppers (*C. annuum*); or as pungent chili peppers, jalapeno peppers, Habanero peppers (*C. chinense*) and TABASCO® peppers (*C. frutescens*); or as a source of dried powders of various colors, such as paprika. Cultivated peppers can be distinguished by their pungency, fruit shape, color and size (see for example U.S. Pat. No. 6,498,287).

Some consumers regard certain types of peppers, for example, sweet bell peppers, as lacking in aroma, or as having a bland flavor, or as having an undesirable flavor. One approach is to breed for sweet peppers with more desirable aromas. *C. chinense* comprises some extremely pungent peppers and has traditionally been used as donors for certain disease resistance traits. However, *C. chinense* has not been explored as a source for desirable pepper flavor. Little is known about aromatic components (e.g., aroma compounds) underlying the *C. chinense* fruit flavor. No objective analytical method has been reported to assess *C. chinense* aroma or flavor. It is also unclear whether *C. chinense* fruit aromas are separable from its high pungency. Numex Suave Orange (*C. chinense*) has been reported as a mild habanero-type pepper, but not a sweet pepper. See Votava and Bosland, *HortScience*, 39(3):627-28 (2004). Accordingly, there is a need in pepper breeding to incorporate desirable aromas or flavor (e.g., aromas characteristic of *C. chinense*) into sweet peppers.

SUMMARY

In an aspect, this disclosure provides a *Capsicum* seed or plant grown therefrom, where the *Capsicum* plant exhibits a pepper fruit at, or immediately prior to, maturity having pericarp comprising a total sugar content of at least 5.5% and one or more aroma molecules characteristic of *Capsicum chinense*. In an aspect, a pepper fruit disclosed herein comprises one or more aroma molecules characteristic of *Capsicum chinense* selected from the group consisting of alpha-Cubebene, delta-Cadinene, 1,4-Cadinadiene, and combinations thereof. In an aspect, a pepper fruit comprises pericarp having a titratable acidity at a level higher than that of pericarp of hybrid pepper PS09954859 grown under similar conditions. In another aspect, a pepper fruit comprises pericarp having a titratable acidity of at least 4.2 millimole (mmol) $H^+$/100 g fresh tissue.

In an aspect, a pepper fruit disclosed herein comprises pericarp comprising alpha-Cubebene at a level having a Relative GC/MS Response Score of at least 0.25. In another aspect, a pepper fruit disclosed herein comprises pericarp comprising delta-Cadinene at a level having a Relative GC/MS Response Score of at least 0.25. In a further aspect, a pepper fruit disclosed herein comprises pericarp comprising 1,4-Cadinadiene at a level having a Relative GC/MS Response Score of at least 0.15.

In another aspect, this disclosure provides a *Capsicum* seed or plant grown therefrom, where the *Capsicum* plant exhibits a pepper fruit at, or immediately prior to, maturity having pericarp comprising a total sugar content of at least 5.5% and one or more aroma molecules characteristic of *Capsicum chinense*, where the one or more aroma molecules are absent from a *Capsicum* with no *Capsicum chinense* in the pedigree, absent from the pericarp of hybrid pepper PS09954859 or at a higher level than that of pericarp of hybrid pepper PS09954859 grown under similar conditions.

In an aspect, a *Capsicum* seed, plant, or fruit disclosed herein is a progeny of *Capsicum* line ZSP8T14-6274 or SVPS2625, where a representative sample of seed of the *Capsicum* line ZSP8T14-6274 has been deposited at ATCC under Accession No. PTA-122300, and where a representative sample of seed of the *Capsicum* line SVPS2625 has been deposited at ATCC under Accession No. PTA-122296.

In another aspect, a *Capsicum* seed, plant, or fruit disclosed herein is an $F_1$ progeny of *Capsicum* line ZSP8T14-6274 or SVPS2625, where a representative sample of seed of the *Capsicum* line ZSP8T14-6274 has been deposited at ATCC under Accession No. PTA-122300, and where a representative sample of seed of the *Capsicum* line SVPS2625 has been deposited at ATCC under Accession No. PTA-122296.

In an aspect, a *Capsicum* seed, plant, or fruit disclosed herein is an $F_2$ progeny of *Capsicum* line ZSP8T14-6274 or SVPS2625, where a representative sample of seed of the *Capsicum* line ZSP8T14-6274 has been deposited at ATCC under Accession No. PTA-122300, and where a representative sample of seed of the *Capsicum* line SVPS2625 has been deposited at ATCC under Accession No. PTA-122296.

In another aspect, a *Capsicum* seed, plant, or fruit disclosed herein is essentially derived from *Capsicum* line ZSP8T14-6274 or SVPS2625, where a representative sample of seed of the *Capsicum* line ZSP8T14-6274 has been deposited at ATCC under Accession No. PTA-122300, and where a representative sample of seed of the *Capsicum* line SVPS2625 has been deposited at ATCC under Accession No. PTA-122296.

In a further aspect, a *Capsicum* seed, plant, or fruit disclosed herein comprises one or more introgressed loci from *Capsicum* line ZSP8T14-6274 or SVPS2625, where a representative sample of seed of the *Capsicum* line ZSP8T14-6274 has been deposited at ATCC under Accession No. PTA-122300, where a representative sample of seed of the *Capsicum* line SVPS2625 has been deposited at ATCC under Accession No. PTA-122296, and where the one or more introgressed loci provide the genetic determinant for producing the one or more aroma molecules characteristic of *Capsicum chinense*.

In an aspect, this disclosure provides a *Capsicum* seed or plant grown therefrom, where the *Capsicum* plant exhibits a fruit comprising at maturity one or more aroma molecules characteristic of *Capsicum chinense* at a level equal to or higher than that of a *Capsicum* line when grown under similar conditions, where said *Capsicum* line is selected from the group consisting of lines ZSP8T14-6274 and SVPS2625, where a representative sample of seed of *Capsicum* line ZSP8T14-6274 has been deposited at ATCC under Accession No. PTA-122300, where a representative sample of seed of *Capsicum* line SVPS2625 has been deposited at ATCC under Accession No. PTA-122296.

In an aspect, a *Capsicum* seed or plant disclosed herein exhibits a pepper fruit at, or immediately prior to, maturity having pericarp comprising a total sugar content of at least 5.5% and one or more terpene molecules selected from the group consisting of alpha-Cubebene at a level having a Relative GC/MS Response Score of at least 0.25, delta-Cadinene at a level having a Relative GC/MS Response Score of at least 0.25, 1,4-Cadinadiene at a level having a Relative GC/MS Response Score of at least 0.15, and any combination thereof.

In another aspect, this disclosure provides a sweet bell pepper fruit comprising at maturity one or more aroma molecules characteristic of *Capsicum chinense*, where the one or more aroma molecules are absent from pericarp of hybrid pepper PS09954859 or at a higher level than that of pericarp of hybrid pepper PS09954859 grown under similar conditions.

In another aspect, this disclosure provides a method of producing a pepper fruit, where the method comprises: cultivating a pepper plant provided herein; and collecting a pepper fruit from the plant.

In an aspect, this disclosure provides a method for producing a *Capsicum* plant capable of producing a sweet pepper fruit comprising one or more aroma molecules characteristic of *Capsicum chinense*, where the method comprises: (a) crossing a *C. annuum* plant or hybrid with a *C. chinense* plant or hybrid to produce a population of progeny *Capsicum* plants; and (b) selecting a progeny *Capsicum* plant comprising a *C. annuum* fruit type and producing a fruit at, or immediately prior to, maturity comprising one or more aroma molecules characteristic of *C. chinense*, where the one or more aroma molecules are selected from the group consisting of alpha-Cubebene at a level having a Relative GC/MS Response Score of at least 0.25; delta-Cadinene at a level having a Relative GC/MS Response Score of at least 0.25; 1,4-Cadinadiene at a level having a Relative GC/MS Response Score of at least 0.15; and any combinations thereof.

In another aspect, this disclosure provides a method for producing a *Capsicum* plant capable of producing a sweet pepper fruit comprising one or more aroma molecules characteristic of *Capsicum chinense*, where the method comprises: (a) crossing a *C. annuum* plant or hybrid with a *C. chinense* plant or hybrid to produce a population of progeny *Capsicum* plants; and (b) selecting a progeny *Capsicum* plant comprising a *C. annuum* fruit type and producing a fruit at, or immediately prior to, maturity comprising one or more aroma molecules characteristic of *C. chinense*.

In another aspect, this disclosure provides a method for selecting a sweet pepper fruit comprising one or more aroma molecules characteristic of *Capsicum chinense*, where the method comprises: (a) obtaining a sweet pepper fruit; and (b) detecting in the sweet pepper fruit one or more aroma molecules selected from the group consisting of alpha-Cubebene, delta-Cadinene, 1,4-Cadinadiene, and combinations thereof.

In another aspect, this disclosure provides a method for introducing a desired *Capsicum chinense* specific aroma molecule into a sweet pepper plant, where the desired *Capsicum chinense* specific aroma molecule is selected from the group consisting of alpha-Cubebene, delta-Cadinene, 1,4-Cadinadiene, and any combinations thereof, where the method comprises:

a. crossing a sweet pepper plant with a plant selected from the group consisting of *Capsicum* line ZSP8T14-6274, a representative sample seed of which line having been deposited at ATCC under Accession No. PTA-122300, a progeny line of *Capsicum* line ZSP8T14-6274, *Capsicum* line SVPS2625, a representative sample of seed of which line having been deposited at ATCC under Accession No. PTA-122296, and a progeny line of *Capsicum* line SVPS2625, b. selecting an $F_1$ progeny pepper plant comprising the desired *Capsicum chinense* specific aroma molecule in a fruit at, or immediately prior to, maturity;

c. backcrossing the $F_1$ progeny to the sweet pepper plant;

d. selecting a backcrossed progeny pepper plant comprising the desired *Capsicum chinense* specific aroma molecule;

e. repeating steps (c) and (d) three or more times in succession to produce selected fourth or higher backcross progeny that comprise the desired *Capsicum chinense* specific aroma molecule.

In another aspect, this disclosure provides a method for producing a *Capsicum* plant exhibiting a sweet pepper fruit comprising one or more desirable aromas, where the method comprises: (a) crossing a *C. annuum* plant or hybrid with a *Capsicum* plant or hybrid capable of producing a fruit exhibiting the one or more desirable aromas to produce a population of progeny *Capsicum* plants; and (b) selecting a progeny *Capsicum* plant comprising a *C. annuum* fruit type and exhibiting a fruit comprising the one or more desirable aromas.

BRIEF DESCRIPTION OF THE FIGURES

FIG. 1: Sample specifications for the consumer liking test detailing hybrid pepper SVPS2625, PERO® brand mini-pointy yellow, and PERO® brand mini-pointy orange peppers (PERO® Family Farms Food Company, LLC).

DETAILED DESCRIPTION

Figure 2:
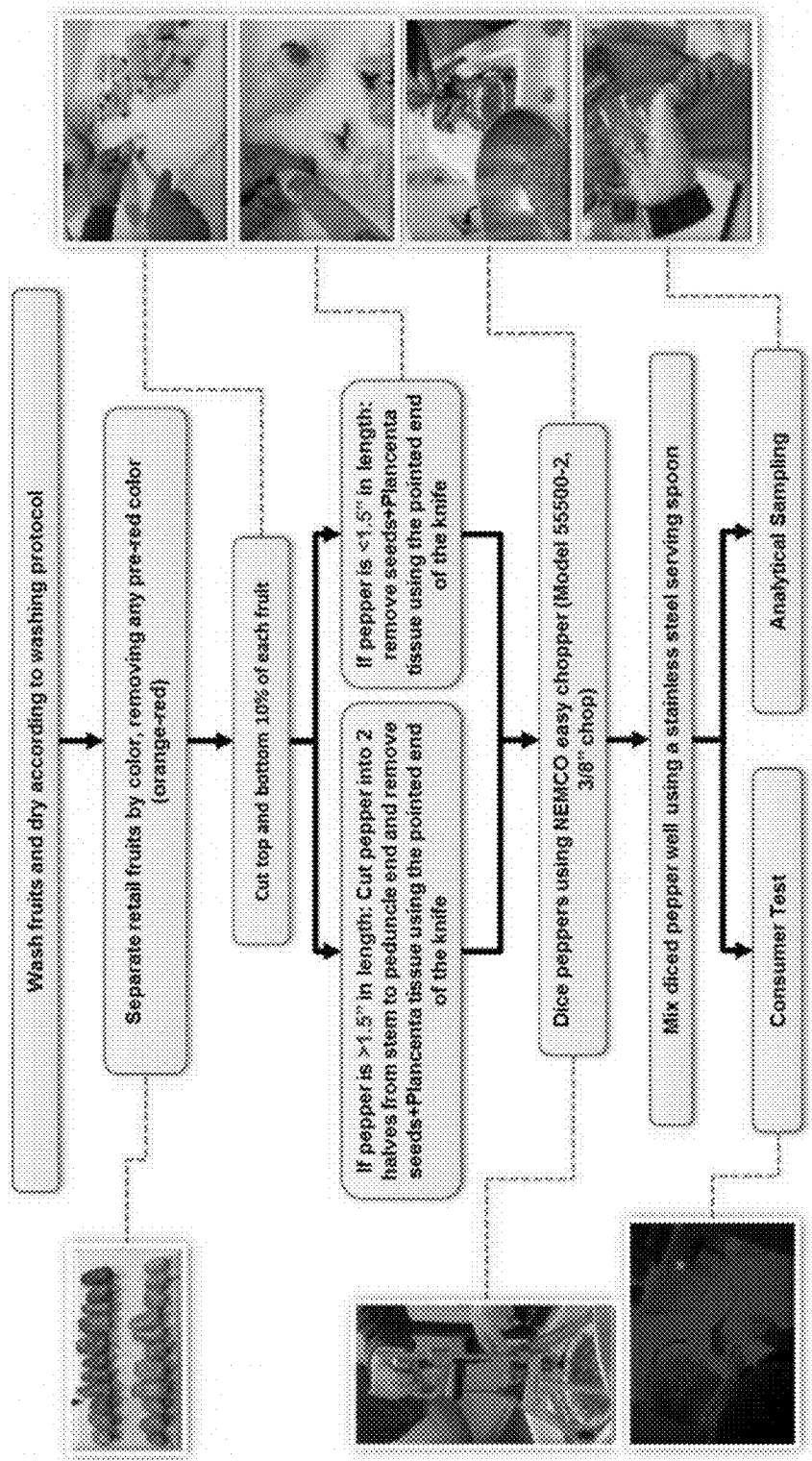
FIG. 2: Flow chart of the preparation steps for diced peppers used in the consumer liking test.

Unless defined otherwise herein, terms are to be understood according to conventional usage by those of ordinary skill in the relevant art.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant.

As used herein, "metabolomics assisted selection" (MAS) is a process by which phenotypes are selected based on a metabolic profile. "Metabolomics assisted selection breeding" refers to the process of selecting a desired trait or traits in a plant or plants by detecting one or more metabolites from the plant, where the metabolites are associated with the desired trait, and then selecting the plant or germplasm possessing those one or more metabolites.

As used herein, a "pepper" refers to a plant of the genus *Capsicum* or a fruit thereof.

As used herein, a "sweet pepper" refers to a fruit or a plant of a non-pungent sweet pepper variety. Example sweet peppers include, but are not limited to, bell peppers (*C. annuum*), the "Thai sweet"—also a cultivar of *C. annuum*, and the "dulce"—a popular cultivar of *C. baccatum*.

As used herein, a "bell pepper" refers to a *C. annuum* pepper plant or fruit with a bell-shaped or blocky fruit. For bell peppers, the fruit length divided by the fruit width is in a range from 0.8 to 1.2.

As used herein, a "*C. annuum* fruit type" refers to a fruit type having a *C. annuum* fruit appearance, e.g., a bell-shaped, blocky, pointed, or round fruit.

Sweet bell pepper, a cultivar of *C. annuum*, has a zero rating on the Scoville scale. Without being bound by any scientific theory, the lack of capsaicin in sweet bell peppers is reported to be due to a recessive mutation that eliminates capsaicin. The Pun1 locus, formerly known as the C locus, encodes a putative acyltransferase AT3, of which the allelic state functions as an on-off switch for pungency in pepper. Hot (pungent) peppers have a functional CS (Pun1) allele, but in sweet (non-pungent) peppers the predominant pun1-1 allele has a deletion in an AT3 gene and, as a consequence, capsaicinoids cannot be formed. See Wahyuni, Ph.D. thesis entitled "Breeding for pepper fruit quality: A genetical metabolomics approach," Wageningen University, Chapter 1, page 6 (2014).

As used herein, "maturity" or "harvest maturity" refers to a pepper fruit developmental stage when the pepper fruit has fully developed (e.g., reached its final size) and is ready for harvest. The development of pepper fruits shows a growth (between 4-7 weeks after fruit set) and ripening (7-10 weeks after fruit set) phase. During growth, fresh weight increases rapidly, while during ripening the color turns from green to a mature color, for example red, yellow or orange, which is reflected in a decreased level of chlorophyll a (i.e., green pigment) and an increased level of carotenoids (i.e., orange/red pigments). As used herein, "at or near maturity" or "at or immediately prior to maturity" refers to a pepper fruit ripening stage where between about 50% and 100% (more preferably between 75% and 100%) of total fruit surface area exhibits mature color.

As used herein, "flavor" refers to the sensory impression of a pepper fruit or fruit part (fruit flesh) perceived during consumption. Flavor is determined mainly by the chemical senses of taste and smell. Flavor can be influenced by volatile and/or non-volatile chemical components (organic acids, lipids, carbohydrates, salts, etc.). The composition of non-volatile compounds influences mainly the sensory perceived taste. Non-volatile compounds include, but are not limited to, sugars (e.g., sucrose, glucose, and fructose) and organic acids (e.g., ascorbic acid, citric acid, malic acid, oxalic acid, fumaric acid, shikimic acid, and pyroglutamic acid).

As used herein, fruit "aroma" refers to the smell of a fruit and is mainly affected by volatile compounds. Exemplary aromatic compounds in sweet peppers have been reported, including 2,3-butanedione (caramel odor), 1-penten-3-one (chemical/pungent, spicy), hexanal (grassy), 3-carene (red bell pepper, rubbery), (Z)-β-ocimene (rancid, sweaty), octanal (fruity), 2-isobutyl-3-methoxypyrazine (green bell pepper), (Z)-linalooloxide, (Z)-2-penten-1-ol, (E)-geranylacetone, (E,Z)-2,6-nonadienal, and (E,E)-decadienal. See, e.g., Selahel et al., "Postharvest responses of red and yellow sweet peppers grown under photo-selective nets," *Food Chemistry*, 173:951-56 (2015); Junior et al., "Analysis of the volatile compounds of Brazilian chilli," *Food Research International* 48:98-107 (2012).

As used herein, "pepper aroma compounds" refer to compounds associated with the aroma of a pepper fruit. Concentrations of pepper aroma compounds can be measured by any known metabolite profiling methods in the art including, without limitation, gas chromatography mass spectrometry (GC-MS), nuclear magnetic resonance spectroscopy, liquid chromatography-linked mass spectrometry. See The Handbook of Plant Metabolomics, edited by Weckwerth and Kahl, (Wiley-Blackwell) (May 28, 2013); see also, Barrett et al., "Color, Flavor, Texture, and Nutritional Quality of Fresh-Cut Fruits and Vegetables: Desirable Levels, Instrumental and Sensory Measurement, and the Effects of Processing," *Critical Reviews in Food Science and Nutrition*, 50(5):369-89 (2010).

As used herein, "*C. chinense* specific aroma compounds" or "aroma compounds characteristic of *C. chinense*" refer to aroma compounds which are found in *C. chinense*, but not in *C. annuum*. Example *C. chinense* specific aroma compounds include, but are not limited to, α-Cubebene, δ-Cadinene, and 1,4-Cadinadiene.

As used herein, "titratable acidity" refers to the number of protons recovered during a titration with a strong base to a specified endpoint. It can also be expressed as a molar quantity (e.g., millimoles $H^+$/100 g) and measured by titration of a sample using a Mettler T90 titrator.

As used herein, "total sugar content" refers to the total percentage of fructose and glucose in a pepper sample.

As used herein, a "Relative GC/MS Response Score" refers to a relative quantification of a volatile compound using solid-phase microextraction (SPME) coupled with gas chromatography mass spectrometry (GC-MS) and an internal deuterated standard (5 ppm, d3-Ethyl Acetate in methanol) as described in Example 2. In short, the retention time and unique ions for a compound of interest are first used to extract the area under its curve. Curve area for a deuterated internal standard is then calculated using a retention time of 61.2 seconds and selected ions (46+91 m/z). The relative GC-MS response score of a compound is then determined using the following formula: Relative GC-MS Response Score of compound X=Area of Compound X/Area of Deuterated Internal Standard.

As used herein, "capsaicinoid" refers to a collection of compounds including capsaicin [N-vanillyl-8-methyl-6-nonenamide], dihydrocapsaicin, and other analogs.

As used herein, "pericarp" refers to the wall of a pepper fruit, which is the colored, edible part of the pepper fruit.

A "*C. annuum* plant" is a plant of the genus *Capsicum* and of the species *annuum*. A *C. annuum* plant can be a pure *C. annuum* plant (e.g., 100% of its genetic material is from *C. annuum*) or a *C. annuum* hybrid. A "*C. annuum* hybrid" is a *C. annuum* plant having one or more segments of nuclear DNA introgressed from another member of the *Capsicum* genus, where greater than about 50%, 60%, 75% of the nuclear DNA is DNA derived from a *C. annuum* plant.

A "*C. chinense* plant" is a plant of the genus *Capsicum* and of the species *chinense*. A *C. chinense* plant can be a pure *C. chinense* plant (e.g., 100% of its genetic material is from *C. chinense*) or a *C. chinense* hybrid. A "*C. chinense* hybrid" is a *C. chinense* plant having one or more segments of nuclear DNA introgressed from another member of the *Capsicum* genus, where greater than about 75% of the nuclear DNA is DNA derived from a *C. chinense* plant. In an aspect, a *C. chinense* hybrid has greater than 80%, 85%, 90%, 95%, 98% or 99% of its nuclear DNA derived from a *C. chinense* plant.

As used herein, "germplasm" refers to living sources of genetic material. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, ovules, or cells that can be cultured into a whole plant.

As used herein, the phrase "associated with" refers to a recognizable and/or assayable relationship between two entities. For example, the phrase "associated with a *C. chinense* aroma" refers to a trait, locus, gene, allele, marker, phenotype, metabolic profile, etc., or the expression thereof, the presence or absence of which can influence or indicate an extent, degree, and/or rate at which a plant or a part of interest thereof has a *C. chinense* aroma. As such, a metabolite marker is "associated with" a trait when it is linked to it and when the presence of the metabolite marker is an indicator of whether and/or to what extent the desired trait or trait form will occur in a plant/germplasm comprising the metabolite marker.

As used herein, "male sterile" or "male sterility" refers to plants that are not usually capable of breeding from self-pollination, but are capable of breeding from cross-pollination. One type of male sterility is cytoplasmic male sterility (CMS). Several CMS systems have been reported in pepper breeding, such as the Peterson CMS system and *Baccatum* CMS system (see US 2013/0145489 A1, published Jun. 6, 2013). In the Peterson CMS system, the male sterility factors are coded in the mitochondrial DNA. The cytoplasm, including the mitochondria, is passed from the female parent to its progeny. Progeny plants coming from a cross between two parents carry the cytoplasm of the female parental plant. Therefore, if the female parental plant displays a CMS trait, then all progenies will also carry the CMS trait in the absence of "Restorer" alleles. In the presence of Restorer alleles, a plant will be fertile even if its cytoplasm is derived from a CMS maternal parent.

As used herein, "genetic element" or "gene" refers to a heritable sequence of DNA, e.g., a genomic sequence, with functional significance. The term "gene" can also be used to refer to, e.g., a cDNA and/or an mRNA encoded by a genomic sequence, as well as to that genomic sequence. A "genetic determinant" refers to one or more genes, gene elements, or combinations thereof that are capable of providing a trait of interest.

As used herein, "crossed" or "cross" means to produce progeny via fertilization (e.g. cells, seeds or plants) and includes crosses between plants (sexual) and self-fertilization (selfing).

As used herein, the term "inbred" means a line that has been bred for genetic homogeneity.

As used herein, the term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines.

As used herein, "introgression" refers to the transmission of a desired allele of a genetic locus from one genetic background to another.

As used herein, the term "chromosome interval" or "chromosomal interval" designates a contiguous linear span of genomic DNA that resides on a single chromosome.

As used herein, "flanked by," when used to describe a chromosomal interval, refers to two loci physically surrounding the chromosomal interval, with one locus on each side of the chromosomal interval. As referenced herein, a chromosomal interval flanked by two marker loci includes the two marker loci.

As used herein, "locus" is a chromosome region or chromosomal region where a polymorphic nucleic acid, trait determinant, gene, or marker is located. A locus can represent a single nucleotide, a few nucleotides or a large number of nucleotides in a genomic region. The loci of this disclosure comprise one or more polymorphisms in a population (e.g., alternative alleles are present in some individuals).

As used herein, "allele" refers to an alternative nucleic acid sequence at a particular locus. The length of an allele can be as small as one nucleotide base. For example, a first allele can occur on one chromosome, while a second allele occurs on a second homologous chromosome, e.g., as occurs for different chromosomes of a heterozygous individual, or between different homozygous or heterozygous individuals in a population.

As used herein, "marker assay" means a method for detecting a polymorphism at a particular locus using a particular method, e.g. measurement of at least one phenotype (such as seed color, flower color, or other visually detectable traits), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, a "population of plants" or a "population of seeds" means a set comprising any number, at least two, of individuals, objects, or data from which samples are taken for evaluation. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants or seeds. The population members need not be identical to the population members selected for use in subsequent cycles of analyses or those ultimately selected to obtain final progeny plants or seeds. Often, a population of plants or seeds is derived from a single biparental cross, but can also derive from two or more crosses between the same or different parents. Although a population of plants or seeds can comprise any number of individuals, those of skill in the art will recognize that plant breeders commonly use population sizes ranging from one or two hundred individuals to several thousand, and that the highest performing 5% to 20% of a population is what is commonly selected to be used in subsequent crosses in order to improve the performance of subsequent generations of the population.

As used herein, "backcross" and "backcrossing" refer to the process whereby a progeny plant is repeatedly crossed back to one of its parents. In a backcrossing scheme, a "donor" parent refers to the parental plant with the desired gene, locus, or trait to be introgressed. A "recipient" parent (used one or more times) or "recurrent" parent (used two or more times) refers to a parental plant into which the gene, locus, or trait is being introgressed. For example, see Ragot, M. et al. Marker-assisted Backcrossing: A Practical Example, in Techniques Et Utilisations Des Marqueurs Moleculaires Les Colloques, Vol. 72, pp. 45-56 (1995); and Openshaw et al., Marker-assisted Selection in Backcross Breeding, in Proceedings Of The Symposium "Analysis of Molecular Marker Data," pp. 41-43 (1994). The initial cross gives rise to the F1 generation. The term "BC1" (backcross 1) refers to the second use of the recurrent parent, "BC2" refers to the third use of the recurrent parent, and so on. In an aspect, a backcross is performed repeatedly, with a progeny individual of each successive backcross generation being itself backcrossed to the same parental genotype.

As used herein, "elite line" or "elite variety" means any line that has resulted from breeding and selection for superior agronomic performance. Similarly, an "elite germplasm" or elite strain of germplasm is an agronomically superior germplasm. Exemplary named pepper types or varieties include Aleppo, Anaheim, ancho, bell, cascabel, cayenne, chilaca, chiltepin, cubanelle, de arbol, dandicut, Fresno, guajillo, Hungarian wax, Italian sweet, jalapeno, Japanese, mirasol, macho, mulato, New Mexico, pasilla, pepperoncini (Tuscan), piquin, pimento, poblano, puya, Serrano and Tientsin (Tien Tsin).

As used herein, "genotype" or "genetic composition" or "genetic complement" is the genetic constitution of an individual (or group of individuals) at one or more genetic loci, as contrasted with the observable trait (phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

As used herein, "selecting" or "selection" in the context of metabolomics-assisted selection, marker-assisted selection, or breeding refer to the act of picking or choosing desired individuals, normally from a population, based on certain pre-determined criteria.

As used herein, the term "trait," "phenotypic trait," or "phenotype" refer to one or more detectable characteristics of a cell or organism which can be influenced by genotype. The phenotype can be observable to the naked eye, or by any other means of evaluation known in the art, e.g., microscopy, biochemical analysis, genomic analysis, transcriptional profiling, metabolic profiling, etc. In some cases, a phenotype is directly controlled by a single gene or genetic locus, e.g., a "single gene trait." In other cases, a phenotype is the result of several genes or genetic loci.

As used herein, a "centimorgan" (cM) is a unit of measure of recombination frequency and genetic distance between two loci. One cM is equal to a 1% chance that a marker at one genetic locus will be separated from a marker at a second locus due to crossing over in a single generation.

As used herein, "linkage" refers to relative frequency at which types of gametes are produced in a cross. For example, if locus A has genes "A" or "a" and locus B has genes "B" or "b," then a cross between parent 1 with AABB and parent 2 with aabb can produce four possible gametes segregating into AB, Ab, aB and ab genotypes. The null expectation is that there will be independent equal segregation into each of the four possible genotypes, i.e. no linkage between locus A and locus B results in ¼ of the gametes from each genotype (AB, Ab, aB, and ab). Segregation of gametes into genotype ratios differing from ¼ indicates linkage between locus A and locus B. As used herein, linkage can be between two markers, or alternatively between a marker and a phenotype. A marker locus can be associated with (linked to) a trait, e.g., a marker locus can be associated with tolerance or improved tolerance to a plant pathogen when the marker locus is in linkage disequilibrium (LD) with the tolerance trait. The degree of linkage of a molecular marker to a phenotypic trait (e.g., a QTL) is measured, e.g., as a statistical probability of co-segregation of that molecular marker with the phenotype.

As used herein, "linkage disequilibrium" (LD) refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. Linkage disequilibrium can be measured using any one of the methods provided in Hedrick, Gametic disequilibrium measures: proceed with caution. *Genetics*, 117:331-41 (1987). The term "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

As used herein, the linkage relationship between a molecular marker and a phenotype is given as the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p<0.5). For example, a significant probability can be less than 0.25, less than 0.20, less than 0.15, or less than 0.1.

As used herein, the term "linked" or "genetically linked," when used in the context of markers and/or genomic regions, means that recombination between two linked loci occurs with a frequency of equal to or less than about 10% (i.e., are separated on a genetic map by not more than 10 cM). In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 20, 19, 18, 17, 16, 15, 14, 13, 12, 11, 10, 9, 8, 7, 6, 5, 4, 3, 2, 1, 0.75, 0.5 or 0.25 cM or less from each other.

As used herein, "marker," "genetic marker," "molecular marker," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

As used herein, "polymorphism" means the presence of one or more variations in a population. A polymorphism can manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation can comprise, but is not limited to, one or more nucleotide base changes, the insertion of one or more nucleotides or the deletion of one or more nucleotides. A polymorphism can arise from random processes in nucleic acid replication, through mutagenesis, as a result of mobile genomic elements, from copy number variation and during the process of meiosis, such as unequal crossing over, genome duplication, and chromosome breaks and fusions. The variation can be commonly found or can exist at low frequency within a population, the former having greater utility in general plant breeding and the latter can be associated with rare but important phenotypic variation. Useful polymorphisms can include a single nucleotide polymorphisms (SNP), an insertion or deletion in DNA sequence (indel), a simple sequence repeats of DNA sequence (SSR), a restriction fragment length polymorphism (RFLP), and a tag SNP. A genetic marker, a gene, a DNA-derived sequence, a RNA-derived sequence, a promoter, a 5' untranslated region of a gene, a 3' untranslated region of a gene, micro-RNA, small interfering RNA, a tolerance locus, a satellite marker, a transgene, mRNA, double-stranded RNA, a transcriptional profile, and a methylation pattern can also comprise a polymorphism. In addition, the presence, absence, or variation in copy number of the preceding can comprise a polymorphism.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "quantitative trait locus (QTL)" means a genetic domain that effects a phenotype that can be described in quantitative terms and can be assigned a "phenotypic value" which corresponds to a quantitative value for the phenotypic trait. A QTL can act through a single gene mechanism or by a polygenic mechanism. In one embodiment of this invention, the boundaries of genomic regions are drawn to encompass markers that will be linked to one or more QTL. In other words, the chromosome interval is drawn such that any marker that lies within that region (including the terminal markers that define the boundaries of the region) is genetically linked to the QTL. Each region comprises at least one QTL, and furthermore, may indeed comprise more than one QTL. Close proximity of multiple QTL in the same region may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention.

As used herein "LOD" means a $\log_{10}$ of an odds ratio and is used to estimate a QTLs location. QTL location estimates are determined empirically. A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander and Botstein, (Lander and Botstein, Mapping Mendelian Factors Underlying Quantitative Traits Using RFLP Linkage Maps. *Genetics,* 121:185-199 (1989), and further described by Arús and Moreno-Gonzalez, *Plant Breeding*, Hayward, Bosemark, Romagosa (eds.) Chapman & Hall, London, pp. 314-331 (1993).

As used herein, a "plant" refers to a whole plant or a cell or tissue culture derived from a plant, comprising any of: whole plants, plant components or organs (e.g., leaves, stems, roots, etc.), plant tissues, seeds, plant cells, and/or progeny of the same. A progeny plant can be from any filial generation, e.g., $F_1, F_2, F_3, F_4, F_5, F_6, F_7$, etc. A plant cell is a biological cell of a plant, taken from a plant or derived through culture from a cell taken from a plant.

As used herein, a "population of plants" or "plant population" means a set comprising any number, including one, of individuals, objects, or data from which samples are taken for evaluation. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

As used herein, "cultivar" and "variety" are used synonymously and mean a group of plants within a species (e.g., *C. annuum*) that share certain genetic traits that separate them from other possible varieties within that species. Pepper cultivars can be inbreds or hybrids.

As used herein, "introgression" or "introgressing" refers to the transmission of a desired trait or a desired allele of a genetic locus from one genetic background to another.

As used herein, "single gene converted" or "single gene conversion" refers to plants that are developed using a plant breeding technique known as backcrossing, or via genetic engineering, where essentially all of the desired morphological and physiological characteristics of a variety are recovered in addition to the single gene transferred into the variety via the backcrossing technique or via genetic engineering.

As used herein, "similar conditions" or "similar growth conditions" refer to similar environmental conditions and agronomic practices for growing plants and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Exemplary ways of cultivating peppers include open field, greenhouse and shade house production.

As used herein, "part(s) of a plant" or a "plant part(s)" includes, without limitation, leaves, calyx, pollen, embryos, pedicle, peduncle, cotyledon, hypocotyl, meristematic cells, roots, root tips, anthers, flowers, seeds, stem, and pepper fruit.

As used herein, "Brix" or "Brix rating" is a measure of the percent of total soluble solids in a fruit. Brix is measured in Degree Brix (° B) using a refractometer or density meter (e.g. Refracto 30PX, Mettler-Toledo, Columbus, Ohio). The amount of sucrose, fructose, vitamins, minerals, proteins, hormones, and other soluble solids can affect Brix ratings. Typically for peppers, a Brix rating of 4 is considered poor, a Brix rating of 6 is considered average, a Brix rating of 8 is considered good, and a Brix rating of 10 is considered excellent. As used here, a Brix rating (° B) can be higher than a total sugar content (%), due to the former reflecting more than the reducing sugars (fructose and glucose) measured by the latter.

As used herein, "hedonic attribute test" is a form of sequential monadic liking test used by consumers for the comparison of sample pepper fruits. Consumers are asked to rate the hedonic attributes of overall rating, flavor, and sweetness. An exemplary evaluation process is described in Example 6. On a scale of 1 to 9, consumers grade each of the attributes in a sample comparison. A score of 1 meaning "dislike extremely", a score of 2 meaning "dislike very much", a score of 3 meaning "dislike moderately", a score of 4 meaning "dislike slightly", a score of 5 meaning "neither like nor dislike", a score of 6 meaning "like slightly", a score of 7 meaning "like moderately", a score of 8 meaning "like very much", and a score of 9 meaning "like extremely".

Peppers are commonly broken down into three groupings: bell peppers, sweet peppers, and hot peppers. Most popular pepper varieties fall into one of these categories, or as a cross between them. These groupings are not absolute, as both "hot pepper" and "sweet pepper" encompass members belonging to several different species. Additionally, members of each of the groups may be different cultivars of the same species. For example, the bell pepper, the jalapeno pepper, and the "Thai sweet" all belong to the species *C. annuum* L. Hot peppers are grown for edible as well as ornamental and medicinal uses. While there are pungent (i.e., "hot") varieties of *C. annuum*, many well-known hot peppers are members of different species. For example, both the cayenne pepper and the TABASCO® pepper are varieties of *C. frutescens*, while some members of *C. chinense*, including the habanero and naga varieties, are well-known hot peppers.

Depending on its pungency, a pepper fruit may be referred to as sweet, mild, medium, hot or very hot pepper varieties as defined in U.S. Pat. No. 8,802,939. For example, a "sweet" pepper has about 0 Scoville Heat Units (SHU) or less than about 0.5 ppm (parts per million) which is less than about 7 SHU of total capsaicinoids (capsaicin, norhydrocapsaicin, and dihydrocapsaicin). A "mild" pepper has greater than about 0.5 ppm (greater than about 7.5 SHU) to about 4.0 ppm (60 SHU) of total capsaicinoids, or more preferably about 2 ppm (30 SHU) to 3 ppm (45 SHU) of total capsaicinoids based upon the weight and capsaicin content of whole pepper fruit.

Capsaicin content or SHU units can be determined by methods known in the art including HPLC methods as described for example in Garces-Claver et al., "Determination of Capsaicin and Dihydrocapsaicin in *Capsicum* Fruit by Liquid Chromatography-Electrospray/Time-of-Flight Mass Spectrometry," *J. Agric. Food Chem.* 54:9303-9311 (2006), hereby incorporated by reference in its entirety. A skilled artisan will understand that capsaicin levels can vary, and that the capsaicin content of some pepper fruit tissues (e.g., placenta) can be higher than that of other tissues. See, Sung et al., "Capsaicin biosynthesis in water-stressed hot pepper fruits," *Bot. Bull. Acad. Sin.* 46:35-42 (2005). The conversion between total capsaicinoid levels and Scoville Heat Units (SHU) was developed by Wilbur Scoville. The number of Scoville units equals the approximate number of times a pepper extract would need to be diluted for the spiciness to be imperceptible. By definition, one part per million (ppm) of capsaicin has a pungency of 15 SHU.

Traditionally, pepper breeding has focused on developing cultivars with high yield (i.e. larger fruit size and more fruits per plant), improving quality attributes (such as bright fruit color and balanced spiciness) and to enhance field performance (improved pathogen resistance and stress tolerance). As discussed above, there is a need to identify aromatic components (e.g., aroma compounds) underlying pepper fruit flavor and aromas. There is also a need to develop an objective analytical method to assess pepper (e.g., *C. chinense*) aroma or flavor. There is also a need in pepper breeding to incorporate desirable aromas or flavor (e.g., aromas characteristic of *C. chinense*) into sweet peppers.

In an aspect, this disclosure provides a *Capsicum* seed or plant grown therefrom, where the *Capsicum* plant is capable of producing a pepper fruit having pericarp comprising a total sugar content of at least 5.5% and one or more aroma molecules characteristic of *C. chinense*. In an aspect, this disclosure provides a *Capsicum* seed or plant grown therefrom, where the *Capsicum* plant exhibits a pepper fruit at, or immediately prior to, maturity having pericarp comprising a total sugar content of at least 5.5% and one or more aroma molecules characteristic of *C. chinense*, where the one or more aroma molecules are absent from pericarp of hybrid pepper PS09954859 or at a higher level than that of pericarp of hybrid pepper PS09954859 grown under similar conditions. In one aspect, total sugar content is quantified using an Agilent HPLC. In an aspect, a *Capsicum* seed is a *C. annuum* seed. In another aspect, one or more aroma molecules are terpene molecules. In a further aspect, terpene molecules are selected from the group consisting of α-Cubebene, δ-Cadinene, 1,4-Cadinadiene, and combinations thereof. In an aspect, a pericarp of a pepper fruit disclosed herein comprises alpha-Cubebene, delta-Cadinene, and 1,4-Cadinadiene. In an aspect, a pepper fruit comprises pericarp having a titratable acidity at a higher level than that of pericarp of hybrid pepper PS09954859 grown under similar conditions. In another aspect, a pepper fruit comprises pericarp having a titratable acidity of at least 4.2, 4.3, 4.4, 4.5, 4.6, 4.7, 4.8, 4.9, 5.0, 5.1, 5.2, 5.3, 5.4, 5.5, 5.6, or 5.7 millimole (mmol) $H^+/100$ g fresh tissue. In another aspect, a pepper fruit comprises pericarp having a titratable acidity of between 4.2 and 5.5, between 4.2 and 5.4, between 4.2 and 5.3, between 4.2 and 5.2, between 4.2 and 5.1, between 4.2 and 5.1, between 4.2 and 5.0, between 4.2 and 4.9, between 4.2 and 4.8, between 4.2 and 4.7, between 4.2 and 4.6, between 4.2 and 4.5, or between 4.2 and 4.4 millimole (mmol) $H^+/100$ g fresh tissue. In one aspect, titratable acidity is determined using 0.1N NaOH to obtain an end pH point of 8.1 endpoint (AOAC, 1990). In one aspect, titratable acidity is determined using a Mettler Toledo T90 automatic titrator.

Aroma molecules, e.g., terpenes, can be sampled from pepper fruits harvested at various maturation stages. These stages are characterized by the percentage of total fruit surface area exhibiting mature color (e.g., color change from green to red, orange or yellow). In one aspect, an aroma molecule described here is detected and measured in a pepper fruit harvested at a stage having at least about 5%, 10%, 25%, 35%, 50%, 60%, 70%, 75%, 80%, 85%, 90%, 95%, or 100% color change. In another aspect, an aroma molecule described here is detected and measured in a pepper fruit harvested at a stage having between 5% and 50%, between 10% and 50%, between 25% and 50%, between 35% and 50%, between 50% and 100%, between 60% and 100%, between 70% and 100%, between 75% and 100%, between 80% and 100%, between 85% and 100%, between 90% and 100%, or between 95% and 100% color change. In a further aspect, an aroma molecule described here is detected and measured in a pepper fruit harvested at a stage having between 60% and 95%, between 70% and 90%, or between 75% and 85% color change. In another aspect, an aroma molecule described here is detected and measured in a pepper fruit harvested at a stage having between 5% and 10%, between 10% and 15%, between 15% and 25%, between 25% and 30%, between 50% and 60%, between 60% and 70%, between 70% and 75%, between 75% and 80%, between 80% and 85%, between 85% and 90%, or between 90% and 95% color change. Aroma molecules are typically measured within 1 week of harvest, more preferably within 5 days, within 3 days, within 1 day, between 1 day and 1 week, between 1 day and 5 days, between 1 day and 3 days, or between 3 days and 5 days of harvesting.

In an aspect, this disclosure provides a *Capsicum* seed or plant grown therefrom, where the *Capsicum* plant exhibits a pepper fruit at maturity having pericarp comprising a total sugar content of at least 5.5% and having a titratable acidity of at least 4.2, 4.3, 4.4, 4.5, 4.6, 4.7, 4.8, 4.9, 5.0, 5.1, 5.2, 5.3, 5.4, 5.5, 5.6, or 5.7 millimole (mmol) $H^+/100$ g fresh tissue. In one aspect, a *Capsicum* seed or plant is a sweet bell pepper. In one aspect, a *Capsicum* seed or plant comprises substantially no pungency. In another aspect, a *Capsicum* seed or plant comprises a pungency of substantially zero Scoville Heat Units (SHUs) or a pungency of below 4000, 3000, 2000, 1000, 500, 250, 200, 150, 100, 50, 40, 30, 20, 10, or 5 SHUs.

In an aspect, this disclosure provides a *Capsicum* seed or plant grown therefrom, where the *Capsicum* plant exhibits a pepper fruit at maturity having pericarp having a titratable acidity of at least 4.2, 4.3, 4.4, 4.5, 4.6, 4.7, 4.8, 4.9, 5.0, 5.1, 5.2, 5.3, 5.4, 5.5, 5.6, or 5.7 millimole (mmol) $H^+/100$ g fresh tissue, and comprising one or more aroma molecules characteristic of *C. chinense*, where the one or more aroma molecules are absent from pericarp of hybrid pepper PS09954859 or at a higher level than that of pericarp of hybrid pepper PS09954859 grown under similar conditions. In another aspect, one or more aroma molecules are selected from the group consisting of α-Cubebene, δ-Cadinene, 1,4-Cadinadiene, and combinations thereof. In an aspect, a pericarp of a pepper fruit disclosed herein comprises alpha-Cubebene, delta-Cadinene, and 1,4-Cadinadiene. In another aspect, one or more aroma molecules are selected from the group consisting of alpha-Cubebene at a level having a Relative GC/MS Response Score of at least 0.25, delta-Cadinene at a level having a Relative GC/MS Response Score of at least 0.25, 1,4-Cadinadiene at a level having a Relative GC/MS Response Score of at least 0.15, or any combination thereof.

In an aspect, this disclosure provides a *Capsicum* seed or plant grown therefrom, where the *Capsicum* plant exhibits a pepper fruit at maturity having pericarp comprising a total sugar content of at least 5.5%, having a titratable acidity of at least 4.2, 4.3, 4.4, 4.5, 4.6, 4.7, 4.8, 4.9, 5.0, 5.1, 5.2, 5.3, 5.4, 5.5, 5.6, or 5.7 millimole (mmol) $H^+/100$ g fresh tissue, comprises a pungency of substantially zero Scoville Heat Units (SHUs) or below 5 SHUs, and further comprising one or more aroma molecules characteristic of *C. chinense* selected from the group consisting of alpha-Cubebene at a level having a Relative GC/MS Response Score of at least 0.25, delta-Cadinene at a level having a Relative GC/MS Response Score of at least 0.25, 1,4-Cadinadiene at a level having a Relative GC/MS Response Score of at least 0.15, or any combination thereof.

In one aspect, a *Capsicum* seed or plant grown therefrom is provided, where the *Capsicum* plant exhibits a pepper fruit at maturity having pericarp comprising a total sugar content of at least about 5.5%, 5.6%, 5.7%, 5.8%, 5.9%, 6.0%, 6.1%, 6.2%, 6.4%, 6.5%, 6.6%, 6.8%, 7.0%, 7.2%, 7.4%, 7.6%, 7.8%, 8.0%, 8.2%, 8.4%, 8.6%, 8.8%, or 9.0%. In one aspect, a *Capsicum* seed or plant grown therefrom is provided, where the *Capsicum* plant exhibits a pepper fruit at, or immediately prior to, maturity having pericarp comprising a total sugar content of between 5.5% and 9.0%, between 5.6% and 9.0%, between 5.7% and 9.0%, between 5.8% and 9.0%, between 5.9% and 9.0%, between 6.0% and 9.0%, between 6.1% and 9.0%, between 6.2% and 9.0%, between 6.4% and 9.0%, between 6.5% and 9.0%, between 6.6% and 9.0%, between 6.8% and 9.0%, between 7.0% and 9.0%, between 7.2% and 9.0%, between 7.4% and 9.0%, between 7.6% and 9.0%, between 7.8% and 8.0% and 9.0%, between 8.2% and 9.0%, between 8.4% and 9.0%, between 8.6% and 9.0%, or between 8.8% and 9.0%. In another aspect, a *Capsicum* seed or plant grown therefrom is provided, where the *Capsicum* plant exhibits a pepper fruit at, or immediately prior to, maturity having pericarp comprising a total sugar content of between 5.5% and 8.8%, between 5.6% and 8.6%, between 5.7% and 8.4%, between 5.8% and 8.2%, between 5.9% and 8.0%, between 6.0% and 7.8%, between 6.1% and 7.6%, between 6.2% and 7.4%, between 6.4% and 7.2%, between 6.5% and 7.1%, between 6.6% and 7.0%, or between 6.8% and 7.0%.

In another aspect, a pepper disclosed herein comprises alpha-Cubebene in pericarp at maturity at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5. In another aspect, a pepper disclosed herein comprises alpha-Cubebene in pericarp at maturity at a level having a Relative GC/MS Response Score of between 0.25 and 17.5, between 0.3 and 17.5, between 0.4 and 17.5, between 0.5 and 17.5, between 0.6 and 17.5, between 0.7 and 17.5, between 0.8 and 17.5, between 0.9 and 17.5, between 1.0 and 17.5, between 1.5 and 17.5 between 2.0 and 17.5, between 2.5 and 17.5, between 3.0 and 17.5, between 4.0 and 17.5, between 5.0 and 17.5, between 7.5 and 17.5, between 10.0 and 17.5, between 12.5 and 17.5, between 15.0 and 17.5, between 0.3 and 15, between 0.4 and 12.5, between 0.5 and 10, between 0.6 and 7.5, between 0.7 and 5.0, between 0.8 and 4.0, between 0.9 and 3.0, between 1.0 and 2.0, between 1.5 and 2.0, between 2.0 and 2.5, between 2.5 and 3.0, between 3.0 and 4.0, between 4.0 and 5.0, between 5.0 and 7.5, between 7.5 and 10.0, between 10.0 and 12.5, or between 12.5 and 15. In a further aspect, a pepper disclosed herein comprises alpha-Cubebene in pericarp at maturity at a level above 1, 2, 3, 4, 5, 6, 7, 8, 9, 10, 15, 20, 25, 30, 35, 40, 50, 60, 100, 150, 200, 300 µg/g fresh fruit. In a further aspect, a pepper disclosed herein comprises alpha-Cubebene in pericarp at maturity at a level between 1 and 2, between 2 and 3, between 3 and 4, between 4 and 5, between 5 and 6, between 6 and 7, between 7 and 8, between 8 and 9, between 9 and 10, between 10 and 15, between 15 and 20, between 20 and 25, between 25 and 30, between 30 and 35, between 35 and 40, between 40 and 50, between 50 and 60, between 60 and 100, between 100 and 150, between 150 and 200, or between 200 and 300 µg/g fresh fruit.

In an aspect, a pepper disclosed herein comprises delta-Cadinene in pericarp at maturity at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5. In another aspect, a pepper disclosed herein comprises delta-Cadinene in pericarp at maturity at a level having a Relative GC/MS Response Score of between 0.25 and 17.5, between 0.3 and 17.5, between 0.4 and 17.5, between 0.5 and 17.5, between 0.6 and 17.5, between 0.7 and 17.5, between 0.8 and 17.5, between 0.9 and 17.5, between 1.0 and 17.5, between 1.5 and 17.5 between 2.0 and 17.5, between 2.5 and 17.5, between 3.0 and 17.5, between 4.0 and 17.5, between 5.0 and 17.5, between 7.5 and 17.5, between 10.0 and 17.5, between 12.5 and 17.5, between 15.0 and 17.5, between 0.3 and 15, between 0.4 and 12.5, between 0.5 and 10, between 0.6 and 7.5, between 0.7 and 5.0, between 0.8 and 4.0, between 0.9 and 3.0, between 1.0 and 2.0, between 1.5 and 2.0, between 2.0 and 2.5, between 2.5 and 3.0, between 3.0 and 4.0, between 4.0 and 5.0, between 5.0 and 7.5, between 7.5 and 10.0, between 10.0 and 12.5, or between 12.5 and 15. In another aspect, a pepper disclosed herein comprises delta-Cadinene in pericarp at maturity at a level above 1, 2, 3, 4, 5, 6, 7, 8, 9, 10, 15, 20, 25, 30, 35, 40, 50, 60, 100, 150, 200, 300 µg/g fresh fruit. In a further aspect, a pepper disclosed herein comprises delta-Cadinene in pericarp at maturity at a level between 1 and 2, between 2 and 3, between 3 and 4, between 4 and 5, between 5 and 6, between 6 and 7, between 7 and 8, between 8 and 9, between 9 and 10, between 10 and 15, between 15 and 20, between 20 and 25, between 25 and 30, between 30 and 35, between 35 and 40, between 40 and 50, between 50 and 60, between 60 and 100, between 100 and 150, between 150 and 200, or between 200 and 300 µg/g fresh fruit.

In an aspect, a pepper disclosed herein comprises 1,4-Cadinadiene in pericarp at maturity at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5. In another aspect, a pepper disclosed herein comprises 1,4-Cadinadiene in pericarp at maturity at a level having a Relative GC/MS Response Score of between 0.15 and 17.5, between 0.18 and 17.5, between 0.2 and 17.5, between 0.25 and 17.5, between 0.3 and 17.5, between 0.4 and 17.5, between 0.5 and 17.5, between 0.6 and 17.5, between 0.7 and 17.5, between 0.8 and 17.5, between 0.9 and 17.5, between 1.0 and 17.5, between 1.5 and 17.5 between 2.0 and 17.5, between 2.5 and 17.5, between 3.0 and 17.5, between 4.0 and 17.5, between 5.0 and 17.5, between 7.5 and 17.5, between 10.0 and 17.5, between 12.5 and 17.5, between 15.0 and 17.5, between 0.15 and 0.18, between 0.18 and 0.2, between 0.2 and 0.25, between 0.25 and 0.3, between 0.3 and 15, between 0.4 and 12.5, between 0.5 and 10, between 0.6 and 7.5, between 0.7 and 5.0, between 0.8 and 4.0, between 0.9 and 3.0, between 0.3 and 0.4, between 0.4 and 0.5, between 0.5 and 0.6, between 0.6 and 0.7, between 0.7 and 0.8, between 0.8 and 0.9, between 0.9 and 1.0, between 1.0 and 2.0, between 1.5 and 2.0, between 2.0 and 2.5, between 2.5 and 3.0, between 3.0 and 4.0, between 4.0 and 5.0, between 5.0 and 7.5, between 7.5 and 10.0, between 10.0 and 12.5, or between 12.5 and 15. In another aspect, a pepper disclosed herein comprises 1,4-Cadinadiene in pericarp at maturity at a level above 1, 2, 3, 4, 5, 6, 7, 8, 9, 10, 15, 20, 25, 30, 35, 40, 50, 60, 100, 150, 200, 300 µg/g fresh fruit. In a further aspect, a pericarp disclosed herein comprises 1,4-Cadinadiene at a level between 1 and 2, between 2 and 3, between 3 and 4, between 4 and 5, between 5 and 6, between 6 and 7, between 7 and 8, between 8 and 9, between 9 and 10, between 10 and 15, between 15 and 20, between 20 and 25, between 25 and 30, between 30 and 35, between 35 and 40, between 40 and 50, between 50 and 60, between 60 and 100, between 100 and 150, between 150 and 200, or between 200 and 300 µg/g fresh fruit. In an aspect, total sugar content and aroma molecules are measured at a maturity stage, e.g., substantially near maximum sweetness and flavor intensity.

In an aspect, a pepper disclosed herein comprises pericarp at maturity having alpha-Cubebene at a concentration equal to or higher than that of a pepper selected from the group consisting of inbred pepper ZSP8T14-6274 and hybrid pepper SVPS2625, when grown under similar conditions. In an aspect, a pepper disclosed herein comprises pericarp at maturity having alpha-Cubebene at a concentration of at least about 5%, 10%, 15%, 20%, 25%, 30%, 40%, 50%, 60%, 70%, 80%, 90%, 100%, 150%, 200%, or 300% higher than that of a pepper selected from the group consisting of inbred pepper ZSP8T14-6274, hybrid pepper SVPS2625, and hybrid pepper PS09954859, when grown under similar conditions. In another aspect, a pepper disclosed herein comprises pericarp at maturity having alpha-Cubebene at a concentration of between 10% and 300%, between 20% and 300%, between 30% and 300%, between 40% and 300%, between 50% and 300%, between 75% and 300%, between 100% and 300%, between 150% and 300%, between 200% and 300%, or between 250% and 300% higher than that of a pepper selected from the group consisting of inbred pepper ZSP8T14-6274, hybrid pepper SVPS2625, and hybrid pepper PS09954859, when grown under similar conditions. In a further aspect, a pepper disclosed herein comprises pericarp at maturity having alpha-Cubebene at a concentration of about 1, 2, 3, 4, 5, 6, 7, 8, 9, 10, 11, 15, 20, 30, or 50 folds higher than that of a pepper selected from the group consisting of inbred pepper ZSP8T14-6274, hybrid pepper SVPS2625, and hybrid pepper PS09954859, when grown under similar conditions.

In an aspect, a pepper disclosed herein comprises pericarp at maturity having delta-Cadinene at a concentration equal to or higher than that of a pepper selected from the group consisting of inbred pepper ZSP8T14-6274 and hybrid pepper SVPS2625, when grown under similar conditions. In an aspect, a pepper disclosed herein comprises pericarp at maturity having delta-Cadinene at a concentration of at least about 5%, 10%, 15%, 20%, 25%, 30%, 40%, 50%, 60%, 70%, 80%, 90%, 100%, 150%, 200%, or 300% higher than that of a pepper selected from the group consisting of inbred pepper ZSP8T14-6274, hybrid pepper SVPS2625, and hybrid pepper PS09954859, when grown under similar conditions. In another aspect, a pepper disclosed herein comprises pericarp at maturity having delta-Cadinene at a concentration of between 10% and 300%, between 20% and 300%, between 30% and 300%, between 40% and 300%, between 50% and 300%, between 75% and 300%, between 100% and 300%, between 150% and 300%, between 200% and 300%, or between 250% and 300% higher than that of a pepper selected from the group consisting of inbred pepper ZSP8T14-6274, hybrid pepper SVPS2625, and hybrid pepper PS09954859, when grown under similar conditions. In a further aspect, a pepper disclosed herein comprises pericarp at maturity having delta-Cadinene at a concentration of about 1, 2, 3, 4, 5, 6, 7, 8, 9, 10, 11, 15, 20, 30, or 50 folds higher than that of a pepper selected from the group consisting of inbred pepper ZSP8T14-6274, hybrid pepper SVPS2625, and hybrid pepper PS09954859, when grown under similar conditions.

In an aspect, a pepper disclosed herein comprises pericarp at maturity having 1,4-Cadinadiene at a concentration equal to or higher than that of a pepper selected from the group consisting of inbred pepper ZSP8T14-6274 and hybrid pepper SVPS2625, when grown under similar conditions. In an aspect, a pepper disclosed herein comprises pericarp at maturity having 1,4-Cadinadiene at a concentration of at least about 5%, 10%, 15%, 20%, 25%, 30%, 40%, 50%, 60%, 70%, 80%, 90%, 100%, 150%, 200%, or 300% higher than that of a pepper selected from the group consisting of inbred pepper ZSP8T14-6274, hybrid pepper SVPS2625, and hybrid pepper PS09954859, when grown under similar conditions. In another aspect, a pepper disclosed herein comprises pericarp at maturity having 1,4-Cadinadiene at a concentration of between 10% and 300%, between 20% and 300%, between 30% and 300%, between 40% and 300%, between 50% and 300%, between 75% and 300%, between 100% and 300%, between 150% and 300%, between 200% and 300%, or between 250% and 300% higher than that of a pepper selected from the group consisting of inbred pepper ZSP8T14-6274, hybrid pepper SVPS2625, and hybrid pepper PS09954859, when grown under similar conditions. In a further aspect, a pepper disclosed herein comprises pericarp at maturity having 1,4-Cadinadiene at a concentration of about 1, 2, 3, 4, 5, 6, 7, 8, 9, 10, 11, 15, 20, 30, or 50 folds higher than that of a pepper selected from the group consisting of inbred pepper ZSP8T14-6274, hybrid pepper SVPS2625, and hybrid pepper PS09954859, when grown under similar conditions.

In an aspect, a pepper disclosed herein comprises pericarp at maturity having alpha-Cubebene at a level having a Relative GC/MS Response Score equal to or at least about 5%, 10%, 15%, 20%, 25%, 30%, 40%, 50%, 60%, 70%, 80%, 90%, 100%, 150%, 200%, or 300% higher than that of a pepper selected from the group consisting of inbred pepper ZSP8T14-6274, hybrid pepper SVPS2625, and hybrid pepper PS09954859, when grown under similar conditions. In another aspect, a pepper disclosed herein comprises pericarp at maturity having alpha-Cubebene at a level having a Relative GC/MS Response Score of between 10% and 300%, between 20% and 300%, between 30% and 300%, between 40% and 300%, between 50% and 300%, between 75% and 300%, between 100% and 300%, between 150% and 300%, between 200% and 300%, or between 250% and 300% higher than that of a pepper selected from the group consisting of inbred pepper ZSP8T14-6274, hybrid pepper SVPS2625, and hybrid pepper PS09954859, when grown under similar conditions. In a further aspect, a pepper disclosed herein comprises pericarp at maturity having alpha-Cubebene at a level having a Relative GC/MS Response Score of about 1, 2, 3, 4, 5, 6, 7, 8, 9, 10, 11, 15, 20, 30, or 50 folds higher than that of a pepper selected from the group consisting of inbred pepper ZSP8T14-6274, hybrid pepper SVPS2625, and hybrid pepper PS09954859, when grown under similar conditions.

In an aspect, a pepper disclosed herein comprises pericarp at maturity having delta-Cadinene at a level having a Relative GC/MS Response Score equal to or at least about 5%, 10%, 15%, 20%, 25%, 30%, 40%, 50%, 60%, 70%, 80%, 90%, 100%, 150%, 200%, or 300% higher than that of a pepper selected from the group consisting of inbred pepper ZSP8T14-6274, hybrid pepper SVPS2625, and hybrid pepper PS09954859, when grown under similar conditions. In another aspect, a pepper disclosed herein comprises pericarp at maturity having delta-Cadinene at a level having a Relative GC/MS Response Score of between 10% and 300%, between 20% and 300%, between 30% and 300%, between 40% and 300%, between 50% and 300%, between 75% and 300%, between 100% and 300%, between 150% and 300%, between 200% and 300%, or between 250% and 300% higher than that of a pepper selected from the group consisting of inbred pepper ZSP8T14-6274, hybrid pepper SVPS2625, and hybrid pepper PS09954859, when grown under similar conditions. In a further aspect, a pepper disclosed herein comprises pericarp at maturity having delta-Cadinene at a level having a Relative GC/MS Response Score of about 1, 2, 3, 4, 5, 6, 7, 8, 9, 10, 11, 15, 20, 30, or 50 folds higher than that of a pepper selected from the group consisting of inbred pepper ZSP8T14-6274, hybrid pepper SVPS2625, and hybrid pepper PS09954859, when grown under similar conditions.

In an aspect, a pepper disclosed herein comprises pericarp at maturity having 1,4-Cadinadiene at a level having a Relative GC/MS Response Score equal to or at least about 5%, 10%, 15%, 20%, 25%, 30%, 40%, 50%, 60%, 70%, 80%, 90%, 100%, 150%, 200%, or 300% higher than that of a pepper selected from the group consisting of inbred pepper ZSP8T14-6274, hybrid pepper SVPS2625, and hybrid pepper PS09954859, when grown under similar conditions. In another aspect, a pepper disclosed herein comprises pericarp at maturity having 1,4-Cadinadiene at a level having a Relative GC/MS Response Score of between 10% and 300%, between 20% and 300%, between 30% and 300%, between 40% and 300%, between 50% and 300%, between 75% and 300%, between 100% and 300%, between 150% and 300%, between 200% and 300%, or between 250% and 300% higher than that of a pepper selected from the group consisting of inbred pepper ZSP8T14-6274, hybrid pepper SVPS2625, and hybrid pepper PS09954859, when grown under similar conditions. In a further aspect, a pepper disclosed herein comprises pericarp at maturity having 1,4-Cadinadiene at a level having a Relative GC/MS Response Score of about 1, 2, 3, 4, 5, 6, 7, 8, 9, 10, 11, 15, 20, 30, or 50 folds higher than that of a pepper selected from the group consisting of inbred pepper ZSP8T14-6274, hybrid pepper SVPS2625, and hybrid pepper PS09954859, when grown under similar conditions.

In an aspect, a pepper disclosed herein further comprises one or more aroma compounds selected from the group consisting of 2,3-butanedione (caramel odor), 1-penten-3-one (chemical/pungent, spicy), hexanal (grassy), 3-carene (red bell pepper, rubbery), (Z)-β-ocimene (rancid, sweaty), octanal (fruity), 2-isobutyl-3-methoxypyrazine (green bell pepper), (Z)-linalooloxide, (Z)-2-penten-1-ol, (E)-geranylacetone, (E,Z)-2,6-nonadienal, and (E,E)-decadienal. In another aspect, a pepper disclosed herein comprises pericarp at maturity having one or more foregoing aroma compounds at a concentration equal to or higher than that of a pepper selected from the group consisting of inbred pepper ZSP8T14-6274, hybrid pepper SVPS2625, and hybrid pepper PS09954859, when grown under similar conditions.

In an aspect, a *Capsicum* seed or plant provided herein exhibits or produces a pepper fruit comprising no capsaicinoid. In an aspect, a pepper fruit provided herein comprises no capsaicinoid at maturity. In an aspect, a pepper fruit from a pepper seed or plant provided herein comprises an equivalent level of capsaicinoid compared to *C. annuum* grown under similar growth conditions. In another aspect, a pepper fruit provided herein comprises a total sugar content of at least 5.5% and a lower level of capsaicinoid compared to *C. chinense* grown under similar growth conditions. In a further aspect, a pepper fruit from a pepper seed or plant provided herein comprises a pungency of substantially zero Scoville Heat Units (SHUs). In another aspect, a pepper fruit from a pepper seed or plant provided herein comprises a pungency of below 4000, 3000, 2000, 1000, 500, 250, 200, 150, 100, 50, 40, 30, 20, 10, or 5 SHUs. In an aspect, the pericarp of a pepper fruit from a pepper seed or plant provided herein comprises a comparable or higher level of one or more aroma molecules selected from the group consisting of alpha-Cubebene, delta-Cadinene, and 1,4-Cadinadiene than *C. chinense* pericarp grown under similar conditions. In an aspect, the pericarp of a pepper fruit from a pepper seed or plant provided herein comprises a higher level of one or more aroma molecules selected from the group consisting of alpha-Cubebene, delta-Cadinene, and 1,4-Cadinadiene than *C. annuum* pericarp grown under similar conditions.

In an aspect, a *Capsicum* seed or plant provided herein is a hybrid. In another aspect, a *Capsicum* seed or plant provided herein is an inbred. In a further aspect, a *Capsicum* seed or plant provided herein is capable of producing a seedless pepper fruit. In an aspect, a *Capsicum* seed or plant provided herein is transgenic. In another aspect, a *Capsicum* seed or plant provided herein is an elite line. In a further aspect, a *Capsicum* seed or plant provided herein is a single gene or locus conversion. In another aspect, a *Capsicum* seed or plant provided herein has multiple genes or loci (e.g., QTLs) introgressed from a *C. chinense* background. In a further aspect, a *Capsicum* seed or plant provided herein is a *C. annuum* line that has been altered with gene editing methods to contain *C. chinense* alleles associated with the aroma molecules described herein.

In an aspect, a *Capsicum* seed or plant provided herein comprises at least about 70%, 75%, 77.5%, 80%, 82.5%, 85%, 86%, 87.5%, 90%, 92.5%, 95%, 97.5%, 98%, 99%, 99.5% of its nuclear genetic material from *C. annuum*. In another aspect, a *Capsicum* seed or plant provided herein comprises equal to or less than about 30%, 25%, 20%, 15%, 14%, 13%, 12.5%, 10%, 7.5%, 5%, 2.5%, 2%, 1%, 0.5% of its nuclear genetic material from a *C. chinense* background. In a further aspect, a *Capsicum* seed or plant provided herein further comprises one or more traits selected from the group consisting of resistance to geminivirus, resistance to *Xanthomonas*, resistance to aphids, resistance to powdery mildew, ease of fruit shedding, cold tolerance, having leaf hairs, thick fruit walls, flavor differences, and the clustering of seed-bearing placental tissue close to the stem of a fruit.

In an aspect, a pepper fruit from a pepper seed or plant disclosed herein comprises a shape selected from the group consisting of block, pointed, and round. In another aspect, a pepper fruit from a pepper seed or plant disclosed herein comprises a color selected from the group consisting of green, yellow, red, purple, black, brown, white, and orange.

In an aspect, a *Capsicum* seed or plant provided herein is a progeny of *Capsicum* line ZSP8T14-6274 or SVPS2625, where a representative sample of seed of the *Capsicum* line ZSP8T14-6274 has been deposited at ATCC under Accession No. PTA-122300, and where a representative sample of seed of the *Capsicum* line SVPS2625 has been deposited at ATCC under Accession No. PTA-122296.

In another aspect, a *Capsicum* seed or plant provided herein is an $F_1$ progeny of *Capsicum* line ZSP8T14-6274 or SVPS2625, where a representative sample of seed of the *Capsicum* line ZSP8T14-6274 has been deposited at ATCC under Accession No. PTA-122300, and where a representative sample of seed of the *Capsicum* line SVPS2625 has been deposited at ATCC under Accession No. PTA-122296.

In a further aspect, a *Capsicum* seed or plant provided herein is an $F_2$ progeny of *Capsicum* line ZSP8T14-6274 or SVPS2625, where a representative sample of seed of the *Capsicum* line ZSP8T14-6274 has been deposited at ATCC under Accession No. PTA-122300, and where a representative sample of seed of the *Capsicum* line SVPS2625 has been deposited at ATCC under Accession No. PTA-122296.

In an aspect, a *Capsicum* seed or plant provided herein is essentially derived from *Capsicum* line ZSP8T14-6274 or SVPS2625, where a representative sample of seed of the *Capsicum* line ZSP8T14-6274 has been deposited at ATCC under Accession No. PTA-122300, and where a representative sample of seed of the *Capsicum* line SVPS2625 has been deposited at ATCC under Accession No. PTA-122296.

In another aspect, a *Capsicum* seed or plant provided herein comprises one or more introgressed loci from *Capsicum* line ZSP8T14-6274 or SVPS2625, where a representative sample of seed of the *Capsicum* line ZSP8T14-6274 has been deposited at ATCC under Accession No. PTA-122300, where a representative sample of seed of the *Capsicum* line SVPS2625 has been deposited at ATCC under Accession No. PTA-122296, and where the one or more introgressed loci provide genetic determinant for producing the one or more aroma molecules characteristic of *Capsicum chinense*.

In a further aspect, the instant disclosure provides a *Capsicum* seed or plant grown therefrom, where the *Capsicum* plant exhibits a pepper fruit having pericarp comprising a total sugar content of at least 5.5%, alpha-Cubebene at a level having a Relative GC/MS Response Score of at least 0.25, delta-Cadinene at a level having a Relative GC/MS Response Score of at least 0.25, and 1,4-Cadinadiene at a level having a Relative GC/MS Response Score of at least 0.15.

In another aspect, the instant disclosure provides a sweet bell pepper fruit comprising one or more aroma molecules characteristic of *C. chinense*, where the one or more aroma molecules are absent from pericarp of hybrid pepper PS09954859 or at a higher level than that of pericarp of hybrid pepper PS09954859 grown under similar conditions. In an aspect, a sweet bell pepper fruit disclosed herein comprises a total sugar content of at least 5.5%. In another aspect, a sweet bell pepper fruit disclosed herein comprises one or more terpene molecules at a higher level than hybrid pepper PS09954859 grown under similar conditions. In an aspect, a sweet bell pepper fruit disclosed herein comprises one or more molecules selected from the group consisting of alpha-Cubebene, delta-Cadinene, and 1,4-Cadinadiene. In another aspect, a sweet bell pepper fruit disclosed herein comprises a higher level of alpha-Cubebene, delta-Cadinene, 1,4-Cadinadiene, or any combination thereof than hybrid pepper PS09954859 grown under similar conditions.

In an aspect, a *Capsicum* plant or seed disclosed herein is capable of producing a pepper fruit comprising a total sugar content of at least 5.5%, 6.0%, 6.5%, or 7.0% and a Brix rating of at least 8.0, 8.5, 9.0, or 9.5. In an aspect, a pepper fruit is preferred by 30%, 35%, 40%, 45%, 50%, 55%, 60%, or 65% more consumers when compared to a commercially available or morphologically comparable sweet pepper fruit in a test of consumer preference. In an aspect, the produced pepper fruit is described by at least 70%, 75%, or 80% of consumers in a test of consumer preference as more flavorful, more sweet, and less bitter when compared to a commercially available or morphologically comparable sweet pepper fruit. In an aspect, a produced pepper fruit scores at least 20% higher than a commercially available or morphologically comparable sweet pepper fruit as based on a consumer graded hedonic attribute test for one or more categories selected from the group consisting of overall rating, flavor, and sweetness. In an aspect, a produced pepper fruit scores at least 5.5, 6.0, 6.5, or greater for one or more categories selected from the group consisting of overall rating, flavor, and sweetness as based on a consumer graded hedonic attribute test. In an aspect, a plant or seed capable of producing a pepper fruit is heterozygous for a QTL SMO2 identifiable by markers SEQ ID NO: 1 or 2 and heterozygous for a QTL SMO3 identifiable by markers SEQ ID NO: 3 or 4.

In an aspect, a pepper fruit is provided comprising a total sugar content of at least 5.5%, 6.0%, 6.5%, 7.0%, 7.5%, 8.0%, 8.5%, or 9.0% and a Brix rating of at least 8.0, 8.5, 9.0, 9.5, 10.0, or 10.5. In an aspect, a pepper fruit is preferred by 30%, 35%, 40%, 45%, 50%, 55%, 60%, or 65% more consumers when compared to a commercially available or morphologically comparable sweet pepper fruit in a test of consumer preference. In an aspect, a pepper fruit is described by at least 70%, 75%, or 80% of consumers in a test of consumer preference as more flavorful, more sweet, and less bitter when compared to a commercially available or morphologically comparable sweet pepper fruit. In an aspect, a pepper fruit scores at least 20% higher than a commercially available or morphologically comparable sweet pepper fruit as based on a consumer graded hedonic attribute test for one or more categories selected from the group consisting of overall rating, flavor, and sweetness. In an aspect, a pepper fruit scores at least 5.5, 6.0, 6.5, or greater for one or more categories selected from the group consisting of overall rating, flavor, and sweetness as based on a consumer graded hedonic attribute test. In an aspect, a plant or seed capable of producing a pepper fruit is heterozygous for a QTL SMO2 identifiable by markers SEQ ID NO: 1 or 2 and heterozygous for a QTL SMO3 identifiable by markers SEQ ID NO: 3 or 4.

In one aspect, a *Capsicum* seed or plant grown therefrom is provided capable of producing a pepper fruit comprising at, or immediately prior to, maturity a pericarp comprising a total sugar content of at least 5.5%, 6.0%, 6.5%, or 7.0% and one or more aroma molecules characteristic of *Capsicum chinense*, wherein a *Capsicum* plant shares a genetic determinant with *Capsicum* line SVPS2625; wherein a genetic determinant provides a total sugar level of at least 5.5%, 6.0%, 6.5%, or 7.0%, a desired *Capsicum chinense* specific aroma molecule, or both. In one aspect, the *Capsicum* seed or plant grown therefrom, contains a genetic determinant also present in a sample seed of SVPS2625, that sample seed having been deposited at ATCC under Accession No. PTA-122296. In one aspect, a *Capsicum* seed or plant grown therefrom, has a desired *Capsicum chinense* specific aroma molecule selected from the group consisting of alpha-Cubebene, delta-Cadinene, 1,4-Cadinadiene.

In one aspect, a *Capsicum* seed or plant grown therefrom is provided capable of producing a pepper fruit exhibiting at, or immediately prior to, maturity a pericarp comprising one or more aroma molecules characteristic of *Capsicum chinense*, wherein a *Capsicum* plant is a progeny of *Capsicum* line ZSP8T14-6274. A representative sample seed *Capsicum* line ZSP8T14-6274 has been deposited at ATCC under Accession No. PTA-122300. In one aspect, a *Capsicum* seed or plant grown therefrom further comprises a total sugar content of at least 5.5%, 6.0%, 6.5%, or 7.0%. In one aspect, a *Capsicum* seed or plant grown therefrom shares a genetic determinant with ZSP8T14-6274 for a desired *Capsicum chinense* specific aroma molecule. In one aspect, a desired *Capsicum chinense* specific aroma molecule is selected from the group consisting of alpha-Cubebene, delta-Cadinene, 1,4-Cadinadiene.

In one aspect, a *Capsicum* plant, or part thereof, disclosed herein is provided capable of producing a pepper fruit exhibiting at, or immediately prior to, maturity a pericarp comprising a total sugar content of at least 5.5%, 6.0%, 6.5%, or 7.0%, wherein a *Capsicum* plant is a progeny of *Capsicum* line SMO8T14-6275. In one aspect, *Capsicum* line SMO8T14-6275 provides a genetic determinant for a total sugar level of at least 5.5%, 6.0%, 6.5%, or 7.0%. In one aspect, *Capsicum* line SMO8T14-6275 is homozygous for SMO2 and SMO3 QTLs, wherein a SMO2 QTL is identifiable by markers SEQ ID NO: 1 or 2, and wherein a SMO3 QTL is identifiable by markers SEQ ID NO: 3 or 4. In an aspect, a progeny plant of *Capsicum* line SMO8T14-6275 is heterozygous for SMO2 and SMO3 QTLs, wherein a SMO2 QTL is identifiable by markers SEQ ID NO: 1 or 2, and wherein a SMO3 QTL is identifiable by markers SEQ ID NO: 3 or 4.

In one aspect, a method is disclosed herein to obtain a *Capsicum* plant by isolating a nucleic acid molecule from a *Capsicum* plant, assaying the isolated nucleic acid molecule for a marker molecule associated with said SMO2 QTL, where a marker molecule is within 10 centimorgans or less from a marker selected from the group consisting of SEQ ID NO: 1 and SEQ ID NO: 2, and selecting a *Capsicum* plant based on the genotyping results that comprises a marker molecule SEQ ID NO: 1 or 2, thereby selecting a SMO2 containing *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 1 and SEQ ID NO: 2. In an aspect, a marker molecule can be within a genomic region flanked by SEQ ID NOs: 1 and 2.

In one aspect, a method is disclosed herein to obtain a *Capsicum* plant by isolating a nucleic acid molecule from a *Capsicum* plant, assaying the isolated nucleic acid molecule for a marker molecule associated with said SMO3 QTL, where a marker molecule is within 10 centimorgans or less from a marker selected from the group consisting of SEQ ID NO: 3 and SEQ ID NO: 4, and selecting a *Capsicum* plant based on the genotyping results that comprises a marker molecule SEQ ID NO: 3 or 4, thereby selecting a SMO3 containing *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 3 and SEQ ID NO: 4. In an aspect, a marker molecule can be within a genomic region flanked by SEQ ID NOs: 3 and 4.

In one aspect, a method is disclosed herein to obtain a *Capsicum* plant by isolating a nucleic acid molecule from a *Capsicum* plant, assaying the isolated nucleic acid molecule for a marker molecule associated with said SMO8 QTL, where a marker molecule is within 10 centimorgans or less from a marker selected from the group consisting of SEQ ID NO: 5 and SEQ ID NO: 6, and selecting a *Capsicum* plant based on the genotyping results that comprises a marker molecule SEQ ID NO: 5 or 6, thereby selecting a SMO8 containing *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 5 and SEQ ID NO: 6. In an aspect, a marker molecule can be within a genomic region flanked by SEQ ID NOs: 5 and 6.

In one aspect, a method is disclosed herein to obtain a *Capsicum* plant by isolating a nucleic acid molecule from a *Capsicum* plant, assaying the isolated nucleic acid molecule for a marker molecule associated with said SZZ3 QTL, where a marker molecule is within 10 centimorgans or less from a marker selected from the group consisting of SEQ ID NO: 7 and SEQ ID NO: 8, and selecting a *Capsicum* plant based on the genotyping results that comprises a marker molecule SEQ ID NO: 7 or 8, thereby selecting a SZZ3 containing *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 7 and SEQ ID NO: 8. In an aspect, a marker molecule can be within a genomic region flanked by SEQ ID NOs: 7 and 8.

In one aspect, a method is disclosed herein to obtain a *Capsicum* plant by isolating a nucleic acid molecule from a *Capsicum* plant, assaying the isolated nucleic acid molecule for a marker molecule associated with said SZZ4 QTL, where a marker molecule is within 10 centimorgans or less from a marker selected from the group consisting of SEQ ID NO: 9 and SEQ ID NO: 10, and selecting a *Capsicum* plant based on the genotyping results that comprises a marker molecule SEQ ID NO: 9 or 10, thereby selecting a SZZ4 containing *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 9 and SEQ ID NO: 10. In an aspect, a marker molecule can be within a genomic region flanked by SEQ ID NOs: 9 and 10.

In one aspect, a method is disclosed herein to obtain a *Capsicum* plant by isolating a nucleic acid molecule from a *Capsicum* plant, assaying the isolated nucleic acid molecule for a marker molecule associated with said SZZ11 QTL, where a marker molecule is within 10 centimorgans or less from a marker selected from the group consisting of SEQ ID NO: 11 and SEQ ID NO: 12, and selecting a *Capsicum* plant based on the genotyping results that comprises a marker molecule SEQ ID NO: 11 or 12, thereby selecting a SZZ11 containing *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 11 and SEQ ID NO: 12. In an aspect, a marker molecule can be within a genomic region flanked by SEQ ID NOs: 11 and 12.

In one aspect, a method is disclosed herein to obtain a *Capsicum* plant by isolating a nucleic acid molecule from a *Capsicum* plant, assaying the isolated nucleic acid molecule for a marker molecule associated with said SHY1 QTL, where a marker molecule is within 10 centimorgans or less from a marker selected from the group consisting of SEQ ID NO: 13 and SEQ ID NO: 14, and selecting a *Capsicum* plant based on the genotyping results that comprises a marker molecule SEQ ID NO: 13 or 14, thereby selecting a SHY1 containing *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 13 and SEQ ID NO: 14. In an aspect, a marker molecule can be within a genomic region flanked by SEQ ID NOs: 13 and 14.

In one aspect, a method is disclosed herein to obtain a *Capsicum* plant by isolating a nucleic acid molecule from a *Capsicum* plant, assaying the isolated nucleic acid molecule for a marker molecule associated with said SHY12 QTL, where a marker molecule is within 10 centimorgans or less from a marker selected from the group consisting of SEQ ID NO: 15 and SEQ ID NO: 16, and selecting a *Capsicum* plant based on the genotyping results that comprises a marker molecule SEQ ID NO: 15 or 16, thereby selecting a SHY12 containing *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 15 and SEQ ID NO: 16. In an aspect, a marker molecule can be within a genomic region flanked by SEQ ID NOs: 15 and 16.

In one aspect, a method is disclosed herein to obtain a population of *Capsicum* plants comprising genotyping a population using a marker molecule associated with a SMO2 QTL, where a marker molecule is within 10 centimorgans or less from a marker selected from the group consisting of SEQ ID NO: 1 and SEQ ID NO: 2, selecting a *Capsicum* plant based on the genotyping results, and producing a progeny from the selected *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 1 and SEQ ID NO: 2. In an aspect, a marker molecule can be within a genomic region flanked by SEQ ID NOs: 1 and 2.

In one aspect, a method is disclosed herein to obtain a population of *Capsicum* plants comprising genotyping a population using a marker molecule associated with a SMO3 QTL, where a marker molecule is within 10 centimorgans or less from a marker selected from the group consisting of SEQ ID NO: 3 and SEQ ID NO: 4, selecting a *Capsicum* plant based on the genotyping results, and producing a progeny from the selected *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 3 and SEQ ID NO: 4. In an aspect, a marker molecule can be within a genomic region flanked by SEQ ID NOs: 3 and 4.

In one aspect, a method is disclosed herein to obtain a population of *Capsicum* plants comprising genotyping a population using a marker molecule associated with a SMO8 QTL, where a marker molecule is within 10 centimorgans or less from a marker selected from the group consisting of SEQ ID NO: 5 and SEQ ID NO: 6, selecting a *Capsicum* plant based on the genotyping results, and producing a progeny from the selected *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 5 and SEQ ID NO: 6. In an aspect, a marker molecule can be within a genomic region flanked by SEQ ID NOs: 5 and 6.

In one aspect, a method is disclosed herein to obtain a population of *Capsicum* plants comprising genotyping a population using a marker molecule associated with a SZZ3 QTL, where a marker molecule is within 10 centimorgans or less from a marker selected from the group consisting of SEQ ID NO: 7 and SEQ ID NO: 8, selecting a *Capsicum* plant based on the genotyping results, and producing a progeny from the selected *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 7 and SEQ ID NO: 8. In an aspect, a marker molecule can be within a genomic region flanked by SEQ ID NOs: 7 and 8.

In one aspect, a method is disclosed herein to obtain a population of *Capsicum* plants comprising genotyping a population using a marker molecule associated with a SZZ4 QTL, where a marker molecule is within 10 centimorgans or less from a marker selected from the group consisting of SEQ ID NO: 9 and SEQ ID NO: 10, selecting a *Capsicum* plant based on the genotyping results, and producing a progeny from the selected *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 9 and SEQ ID NO: 10. In an aspect, a marker molecule can be within a genomic region flanked by SEQ ID NOs: 9 and 10.

In one aspect, a method is disclosed herein to obtain a population of *Capsicum* plants comprising genotyping a population using a marker molecule associated with a SZZ11 QTL, where a marker molecule is within 10 centimorgans or less from a marker selected from the group consisting of SEQ ID NO: 11 and SEQ ID NO: 12, selecting a *Capsicum* plant based on the genotyping results, and producing a progeny from the selected *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 11 and SEQ ID NO: 12. In an aspect, a marker molecule can be within a genomic region flanked by SEQ ID NOs: 11 and 12.

In one aspect, a method is disclosed herein to obtain a population of *Capsicum* plants comprising genotyping a population using a marker molecule associated with a SHY1 QTL, where a marker molecule is within 10 centimorgans or less from a marker selected from the group consisting of SEQ ID NO: 13 and SEQ ID NO: 14, selecting a *Capsicum* plant based on the genotyping results, and producing a progeny from the selected *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 13 and SEQ ID NO: 14. In an aspect, a marker molecule can be within a genomic region flanked by SEQ ID NOs: 13 and 14.

In one aspect, a method is disclosed herein to obtain a population of *Capsicum* plants comprising genotyping a population using a marker molecule associated with a SHY12 QTL, where a marker molecule is within 10 centimorgans or less from a marker selected from the group consisting of SEQ ID NO: 15 and SEQ ID NO: 16, selecting a *Capsicum* plant based on the genotyping results, and producing a progeny from the selected *Capsicum* plant. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 15 and SEQ ID NO: 16. In an aspect, a marker molecule can be within a genomic region flanked by SEQ ID NOs: 15 and 16.

In an aspect, a method is disclosed herein to identify a plant or progeny plant of SVPS2625 by obtaining a *Capsicum* plant and genotyping a *Capsicum* plant using a marker molecule associated with a SMO2 QTL, where a marker molecule is within 10 centimorgans or less from a marker selected from the group consisting of SEQ ID NO: 1 and SEQ ID NO: 2. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 1 and SEQ ID NO: 2. In an aspect, a marker molecule can be within a genomic region flanked by SEQ ID NOs: 1 and 2.

In an aspect, a method is disclosed herein to identify a plant or progeny plant of SVPS2625 by obtaining a *Capsicum* plant and genotyping a *Capsicum* plant using a marker molecule associated with a SMO3 QTL, where a marker molecule is within 10 centimorgans or less from a marker selected from the group consisting of SEQ ID NO: 3 and SEQ ID NO: 4. In an aspect, a marker molecule can be within 8 centimorgans, within 5 centimorgans, within 3 centimorgans, within 2 centimorgans, or within 1 centimorgan or less from a marker selected from the group consisting of SEQ ID NO: 3 and SEQ ID NO: 4. In an aspect, a marker molecule can be within a genomic region flanked by SEQ ID NOs: 3 and 4.

In an aspect, a pepper seed or pepper plant disclosed herein is capable of producing a pepper having one or more desirable aroma compounds and further exhibits one or more traits selected from the group consisting of:

a. plants with prostrate, compact, erect growth habits;
b. plants that have glabrous stems or have sparse, intermediate or abundant stem pubescens;
c. plants that have glabrous leaves or have sparse, intermediate or abundant leaf pubescens;
d. plants with green or purple stems;
e. plants that have pendant, intermediate, or erect pedicle position at anthesis;
f. plants that have white, green-white, lavender, blue or violet corolla color;
g. plants with yellow, pale blue, blue, or purple anthers;
h. plants with white or blue filament colors;
i. plants having a stigma included within the anthers, at the same level as the anthers, or exerted beyond the anthers at full anthesis;
j. plants that are male sterile or male fertile;
k. plants that have low, intermediate or high fruit set;
l. plants with white, straw or cream, yellow, brown, dark brown, or black seeds;
m. plants that have smooth, intermediate, or dentate calyx margins;
n. plants that have or lack an annular constriction at the junction of the calyx and peduncle;
o. plants that have declining, intermediate, or erect fruit position;
p. plants that have green, yellow, orange, red, purple, brown, white, or black immature fruit;
q. plants that have green, yellow, orange, red, purple, brown, white or black mature fruit;
r. plants with pepper fruit that is sweet, or has low (i.e. mild), intermediate (i.e. medium) or high (i.e. hot or very hot) pungency;
s. plants that have an average fruit length at ripeness that is very short (less than about one cm), short (about 5 cm or about 2 to about 7 cm), medium (about 10 cm or about 7 to about 12 cm), long (about 15 cm or about 13 to about 25 cm) or very long (greater than 25 cm or about 25 cm to about 40 cm);
t. plants with a fruit wall thickness (measured halfway between the point of attachment of the stem and the blossom end) from about 0.5 to 1.5 mm or from about 1 to about 2.5 mm or from about 1.5 to about 4 mm or from about 2 to about 5 mm, or from about 3 to about 6 mm, or from about 3.5 mm to about 7.5 mm;
u. plants that have an average fruit width at ripeness that is about 0.3 to 1 cm, about 1 to 2 cm, about 2 to 4 cm, about 3 to 7, about 6 to 10, about 7 to 11 or greater than about 11 cm;
v. plants without persistent fruit or plants with persistent fruit (fruit that persists and maintains an attachment to the plant after ripening);
w. plants with pepper fruit having an average weight at ripeness from about 1 to 5 g, 5 to 25 g, 25 to 50 g, 50 to 100 g, 100 to 250 g, 150 to 450 g, 200 to 500 g or 300 to 550 g.
x. plants with pepper fruit that is elongate, oblate, round, conical or pointed, campanulate, or bell/blocky;
y. plants where the pepper fruit shape at the point of attachment is acute, obtuse, truncate, cordate, or lobate;
z. plants where the pepper fruit has or lacks a neck at the base of the fruit;
aa. plants where the blossom end is pointed, blunt, or sunken;
bb. plants where the pepper fruit has a smooth, slightly corrugated, intermediate, or very corrugated cross section;
cc. plants with resistance to one or more pests (e.g., nematodes and aphids);
dd. plants with resistance to diseases caused by one or more bacteria or fungi (e.g., *Xanthamonas* sp. and *Leveillula taurica*);
ee. plants with resistance to diseases caused by one or more viruses (e.g., geminivirus, tobamovirus);
ff. plants having or lacking anthocyanins in unripe pepper fruit;
gg. plants having or lacking anthocyanins in ripe pepper fruit;
hh. plants that are resistant or susceptible to low temperature;
ii. plants that are resistant or susceptible to high temperature;
jj. plants that are resistant or susceptible to drought;
kk. plants that are resistant or susceptible to high salt;
ll. plants that are resistant or susceptible to flooding;
mm. plants that are resistant or susceptible to heavy metal;
nn. plants that are resistant or susceptible to high soil moisture;
oo. plants that are resistant or susceptible to high humidity; and
pp. plants that shed fruit easily or do not shed fruit easily.

In another aspect, this disclosure provides a container of pepper seeds described herein and a population of pepper plants described herein. A container of pepper seeds of the instant disclosure may contain any number, weight or volume of seeds. For example, a container can contain at least, or greater than, about 10, 25, 50, 100, 200, 300, 400, 500, 600, 700, 800, 900, 1000, 1500, 2000, 2500, 3000, 3500, 4000 or more seeds. Alternatively, the container can contain at least, or greater than, about 5 grams, 10 grams, 15 grams, 20 grams, 25 grams, 50 grams, 100 grams, 250 grams, 500 grams, or 1000 grams of seeds. Alternatively, the container can contain at least, or greater than, about 1 ounce, 5 ounces, 10 ounces, 1 pound, 2 pounds, 3 pounds, 4 pounds, 5 pounds or more seeds. Containers of pepper seeds may be any container available in the art. By way of non-limiting example, a container may be a box, a bag, a can, a packet, a pouch, a tape roll, a pail, a tube, or a bottle.

In an aspect, methods, pepper plants or seeds disclosed herein are used in combination with one or more pesticides including, but not limited to, herbicides, fungicides, insecticides, microbiocides, nematicides, insect repellents, bactericides, and other substances used to control pests. In another aspect, methods or pepper plants disclosed herein are used in combination with one or more triazoles, strobilurins, acylamino acids, pyrimidines, pyridines, arylphenyl ketones, amides, benzanilides, imidazoles, dinitrophenols, morpholines, phenylsulfamides and organophosphorus cpds, derivatives thereof and combinations thereof which may be applied as seed, foliar, drench or drip treatments.

In one aspect, pepper seeds disclosed herein are untreated. In another aspect, pepper seeds disclosed herein can be subjected to various treatments. For example, the seeds can be treated to improve germination by priming the seeds or by disinfection to protect against seedborne pathogens. In another aspect, seeds can be coated with any available coating to improve, for example, plantability, seed emergence, and protection against soilborne pathogens. Seed coating can be any form of seed coating including, but not limited to, pelleting, film coating, and encrustments.

In one aspect, this disclosure provides pepper plant cells, tissues, and organs that are not reproductive material and do not mediate the natural reproduction of the plant. In another aspect, this disclosure also provides pepper plant cells, tissues, and organs that are reproductive material and mediate the natural reproduction of the plant. In another aspect, this disclosure provides pepper plant cells, tissues, and organs that cannot maintain themselves via photosynthesis. In another aspect, this disclosure provides somatic pepper plant cells. Somatic cells, contrary to germline cells, do not mediate plant reproduction.

The provided cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, bud, or vascular tissue. In another aspect, this disclosure provides a pepper plant chloroplast. In a further aspect, this disclosure provides epidermal cells, stomata cell, leaf or root hairs, a storage root, or a tuber. In another aspect, this disclosure provides a pepper protoplast, mitochondria, or callus.

Skilled artisans understand that pepper plants naturally reproduce via seeds, not via asexual reproduction or vegetative propagation. In one aspect, this disclosure provides pepper endosperm. In another aspect, this disclosure provides pepper endosperm cells. In a further aspect, this disclosure provides a male or female sterile pepper plant, which cannot reproduce without human intervention.

In a further aspect, this disclosure provides processed products made from the disclosed pepper plants. Such products include, but are not limited to, prepared or cut pericarp, meal, oil, plant extract, starch, or fermentation or digestion products.

In another aspect, the instant disclosure also provides a method of producing a pepper fruit, the method comprising: (a) cultivating a pepper plant disclosure herein; and (b) collecting a pepper fruit from the pepper plant.

In a further aspect, the instant disclosure also provides a method for producing a *Capsicum* plant capable of producing a sweet pepper fruit comprising one or more aroma molecules characteristic of *C. chinense*, where the method comprises: (a) crossing a *C. annuum* plant or hybrid with a *C. chinense* plant or hybrid to produce a population of progeny *Capsicum* plants; and (b) selecting a progeny *Capsicum* plant comprising a *C. annuum* fruit type and producing a fruit comprising one or more aroma molecules characteristic of *C. chinense*. In an aspect, a method further comprises: (c) backcrossing a selected progeny *Capsicum* plant with a *C. annuum* plant to produce a further progeny generation of *Capsicum* plant. In another aspect, a method further comprises: (d) a further progeny *Capsicum* plant comprising a *C. annuum* fruit type and producing a fruit comprising one or more aroma molecules characteristic of *C. chinense*.

In an aspect, a *C. annuum* plant or hybrid produced from or used in a method disclosed herein is male sterile. In another aspect, a *C. annuum* plant or hybrid produced from or used in a method disclosed herein is cytoplasmic male sterile. In an aspect, a *C. chinense* plant or hybrid produced from or used in a method disclosed herein is male sterile. In another aspect, a *C. chinense* plant or hybrid produced from or used in a method disclosed herein is cytoplasmic male sterile.

In an aspect, a *C. annuum* hybrid produced from or used in a method disclosed herein has equal to or greater than about 75%, 77.5%, 80%, 85%, 86%, 87.5%, 90%, 95%, 98% or 99% of its nuclear DNA derived from a *C. annuum* plant. In an aspect, a *C. annuum* hybrid provided herein comprises an introgression from another *Capsicum* species. In an aspect, an introgression found in a *C. annuum* hybrid is an introgression from one or more *Capsicum* species selected from the group consisting of *C. chinense*, *C. baccatum*, *C. praetermissum*, *C. frutescens*, *C. galapagoense*, and *C. eximium*. In another aspect, an introgression found in a *C. annuum* hybrid is an introgression from *Capsicum chinense*. The fraction of the genome that is derived from *C. chinense* or *C. annuum* can be established by any method known in the art including, but not limited to, the detection of markers or sequencing to determine where introgressions have occurred.

In an aspect, a method disclosed herein further comprises detecting one or more aroma molecules in fruits of the population of progeny *Capsicum* plants via GC/MS. In another aspect, one or more aroma molecules detected in a method disclosed herein are terpene molecules. In another aspect, one or more aroma molecules detected in a method disclosed herein are selected from the group consisting of alpha-Cubebene, delta-Cadinene, 1,4-Cadinadiene, and combinations thereof. In an aspect, a fruit of a selected progeny *Capsicum* plant comprises alpha-Cubebene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5. In another aspect, a fruit of a selected progeny *Capsicum* plant comprises delta-Cadinene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5. In a further aspect, a fruit of a selected progeny *Capsicum* plant comprises 1,4-Cadinadiene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5. In another aspect, a selected progeny *Capsicum* plant is capable of producing a fruit having a total sugar content of at least 5.5%.

In an aspect, the instant disclosure further provides a method for selecting a sweet pepper fruit comprising one or more aroma molecules characteristic of *C. chinense*, where the method comprises: (a) obtaining a sweet pepper fruit; (b) detecting in the sweet pepper fruit one or more aroma molecules selected from the group consisting of alpha-Cubebene, delta-Cadinene, 1,4-Cadinadiene, and combinations thereof.

In another aspect, the instant disclosure further provides a method for introducing a desired *C. chinense* specific aroma molecule into a sweet pepper plant, the method comprising: (a) crossing a sweet pepper plant with a plant selected from the group consisting of *Capsicum* line ZSP8T14-6274, a representative sample seed of which line having been deposited at ATCC under Accession No. PTA-122300, a progeny line of *Capsicum* line ZSP8T14-6274, *Capsicum* line SVPS2625, a representative sample of seed of which line having been deposited at ATCC under Accession No. PTA-122296, and a progeny line of *Capsicum* line SVPS2625; (b) selecting an $F_1$ progeny pepper plant comprising the desired *C. chinense* specific aroma molecule; (c) backcrossing the $F_1$ progeny to the sweet pepper plant; (d) selecting a backcrossed progeny pepper plant comprising the desired *C. chinense* specific aroma molecule; and (e) repeating steps (c) and (d) three or more times in succession to produce selected fourth or higher backcross progeny that comprise the desired *C. chinense* specific aroma molecule. In an aspect, the desired *C. chinense* specific aroma molecule is selected from the group consisting of alpha-Cubebene, delta-Cadinene, 1,4-Cadinadiene, and combinations thereof.

In an aspect, the instant disclosure provides a method for producing a *Capsicum* plant exhibiting a sweet pepper fruit comprising one or more desirable aromas, where said method comprises: (a) crossing a *C. annuum* plant or hybrid with a *Capsicum* plant or hybrid capable of producing a fruit exhibiting said one or more desirable aromas to produce a population of progeny *Capsicum* plants; and (b) selecting a progeny *Capsicum* plant comprising a *C. annuum* fruit type and exhibiting a fruit comprising said one or more desirable aromas. In an aspect, a method disclosed herein comprises detecting said one or more desirable aromas via GC/MS. In another aspect, one or more desirable aromas comprise terpene molecules. In a further aspect, one or more desirable aromas comprising a terpene are selected from the group consisting of alpha-Cubebene, delta-Cadinene, 1,4-Cadinadiene, and combinations thereof. In another aspect, one or more desirable aromas comprise alpha-Cubebene, delta-Cadinene, and 1,4-Cadinadiene. In another aspect, a method disclosed herein further comprises genotyping the Pun1 locus in a selected progeny *Capsicum* plant. In a further aspect, genotyping further comprises detecting a pun1-1 allele. In a further aspect, progeny in a breeding cross are selected based on the outcome of detection of the pun1-1 allele.

Pepper plants, seeds, or fruits disclosed herein can be identified by assessing their genetic complements. Plant genetic complements may be assessed by genetic marker profiles, and by the expression of phenotypic traits that are characteristic of the expression of the genetic complement, e.g., isozyme typing profiles. Genetic marker assays include many well-known techniques, such as Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), Simple Sequence Repeat (SSR), INDEL (INsertion/DELetion) and Single Nucleotide Polymorphisms (SNPs).

Pepper plants or seeds disclosed herein (e.g., line ZSP8T14-6274 and hybrids SVPS2625, 2626, and 2646) can be used as starting varieties to develop or derive new pepper varieties. The development of new varieties using one or more starting varieties is well known in the art. For example, novel varieties may be created by crossing a pepper disclosed herein with a different pepper plant followed by multiple generations of breeding according to well-known methods.

In selecting such a second plant to cross for the purpose of developing novel lines or varieties, it may be desired to choose those plants which either themselves exhibit one or more selected desirable characteristics or which exhibit the desired characteristic(s) when in hybrid combination. Examples of desirable traits include: high seed yield, high seed germination rate, seedling vigor, early fruit maturity, high fruit yield, ease of fruit setting, disease tolerance or resistance, and adaptability for soil and climate conditions. Consumer-driven traits, such as a preference for a given fruit size, shape, color, and texture are other traits that may be incorporated into new lines of sweet pepper plants developed by this disclosure.

Particularly desirable traits that may be incorporated by this disclosure are improved resistance to different viral, fungal, and bacterial pathogens. *Anthracnose* and *Phytophthora* blight are fungal diseases affecting various species of pepper. Fruit lesions and fruit rot are the commercially important aspects of these diseases. Bacterial leaf spot and bacterial wilt are other diseases affecting pepper plants, especially during the wet season. Viral pathogens affecting pepper plants include Tomato spotted wilt virus, Cucumber mosaic virus, Chili veinal mottle virus, Geminiviruses, Potyviruses, Pepper mosaic virus, and Tobacco mosaic virus.

Improved resistance to insect pests is another desirable trait that may be incorporated into new lines of pepper plants developed by this disclosure. Insect pests affecting the various species of pepper include the European corn borer, corn earworm, aphids, flea beetles, whiteflies, mites, broad mites, the pepper weevil and thrips.

Once initial crosses have been made, inbreeding and selection take place to produce new varieties. Molecular markers or metabolic profiling can be used to assist selection of desired progenies and further breeding. For development of a uniform line, often five or more generations of selfing and selection are involved.

Uniform lines of new pepper varieties may also be developed by way of double-haploids. Pepper is naturally a diploid and the basic chromosome number of the genus is x=12, most are 2n=2x=24, including the cultivated ones. A few wild species have 2n=26. Ploidy changes (both tetraploidy and haploidy) are relatively easy to induce in *Capsicum* species. In fact, the inducement of an octaploid *C. annuum* was reported (Panda et al., *Theor. Appl. Genet.* 68: 567-570 (1984)). Doubled haploids have proved particularly valuable in breeding. This technique allows the creation of true breeding lines without the need for multiple generations of selfing and selection. In this manner true breeding lines can be produced in as little as one generation.

Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the disclosure, any of such techniques may be used to achieve a homozygous line.

Besides doubled haploid, backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci in the pepper genome. The last backcross generation would be selfed to give pure breeding progeny for the trait being transferred.

In a further aspect, pepper plants disclosed herein can also be subject to additional breeding using one or more known methods in the art, e.g., pedigree breeding, recurrent selection, mass selection, and mutation breeding. Pedigree breeding starts with the crossing of two genotypes, such as a pepper variety comprising a desirable aroma disclosed herein and another pepper variety lacking such an aroma. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding to fix loci in the variety, successive filial generations will serve to increase seed of the developed variety. The developed variety may comprise homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a pepper variety may be crossed with another variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet one or several of the desired attributes of the non-recurrent parent. This approach leverages the value and strengths of the recurrent parent for use in new pepper varieties.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic line. A synthetic line is the resultant progeny formed by the intercrossing of several selected varieties.

Mass selection is another useful technique when used in conjunction with metabolic marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self-pollination, directed pollination could be used as part of the breeding program.

Mutation breeding can also be used to introduce new traits into pepper plants disclosed herein. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines). Transposon- or T-DNA-based mutagenesis is also encompassed by the present disclosure. Once a desired trait is observed through mutagenesis the trait may then be incorporated into existing germplasm by traditional breeding techniques. A pepper plant or seed provided herein can also be produced by one or more genome engineering techniques or subject to further genomic editing. For example, one or more genes or loci can be introduced into a *C. annuum* background. Exemplary genome engineering techniques include meganucleases, zinc-finger nucleases, TALENs, and CRISPR/Cas9 systems. See, e.g., Gaj et al., ZFN, TALEN, and CRISPR/Cas-based methods for genome engineering. *Trends in Biotechnology*, 31:397-405 (2013).

Pepper plants or lines disclosed herein can also be genetically engineered to express various phenotypes of agronomic interest. Exemplary genes implicated in this regard include, but are not limited to, genes that confer resistance to pests or disease, genes that confer resistance or tolerance to an herbicide, genes that control male sterility, genes that affect abiotic stress resistance (e.g., against salt, heavy metal, flooding), and other genes and transcription factors that affect plant growth and agronomic traits such as yield, flowering, plant growth or plant architecture.

The following are exemplary embodiments of the present application:

Embodiment 1

A *Capsicum* seed or plant grown therefrom, wherein the *Capsicum* plant exhibits a pepper fruit at, or immediately prior to, maturity having pericarp comprising a total sugar content of at least 5.5% and one or more aroma molecules characteristic of *Capsicum chinense*.

Embodiment 2

A *Capsicum* seed or plant grown therefrom, wherein the *Capsicum* plant exhibits a pepper fruit at, or immediately prior to, maturity having pericarp comprising a total sugar content of at least 5.5% and one or more aroma molecules characteristic of *Capsicum chinense*, wherein the one or more aroma molecules are absent from pericarp of hybrid pepper PS09954859 or at a higher level than that of pericarp of hybrid pepper PS09954859 grown under similar conditions.

Embodiment 3

The *Capsicum* seed or plant grown therefrom, according to Embodiment 1, wherein the pericarp comprises a titratable acidity at a higher level than that of pericarp of hybrid pepper PS09954859 grown under similar conditions.

Embodiment 4

The *Capsicum* seed or plant grown therefrom, according to Embodiment 1, wherein the pericarp comprises a titratable acidity of at least 4.2, 4.3, 4.4, 4.5, 4.6, 4.7, 4.8, 4.9, 5.0, 5.1, 5.2, 5.3, 5.4, 5.5, 5.6, or 5.7 mmol H$^+$/100 g fresh tissue.

Embodiment 5

The *Capsicum* seed or plant grown therefrom, according to Embodiment 1, wherein the *Capsicum* seed is a *Capsicum annuum* seed.

Embodiment 6

The *Capsicum* seed or plant grown therefrom, according to Embodiment 1, wherein the one or more aroma molecules are terpene molecules.

Embodiment 7

The *Capsicum* seed or plant grown therefrom, according to Embodiment 6, wherein the terpene molecules are selected from the group consisting of alpha-Cubebene, delta-Cadinene, 1,4-Cadinadiene, and combinations thereof.

Embodiment 8

The *Capsicum* seed or plant grown therefrom, according to Embodiment 6, wherein the pericarp comprises alpha-Cubebene, delta-Cadinene, and 1,4-Cadinadiene.

Embodiment 9

The *Capsicum* seed or plant grown therefrom, according to Embodiment 6, wherein the pericarp comprises alpha-Cubebene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5.

Embodiment 10

The *Capsicum* seed or plant grown therefrom, according to Embodiment 6, wherein the pericarp comprises alpha-Cubebene at a level above 1, 2, 3, 4, 5, 6, 7, 8, 9, 10, 15, 20, 25, 30, 35, 40, 50, 60, 100, 150, 200, 300 µg/g fresh fruit.

Embodiment 11

The *Capsicum* seed or plant grown therefrom, according to Embodiment 6, wherein the pericarp comprises delta-Cadinene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5.

Embodiment 12

The *Capsicum* seed or plant grown therefrom, according to Embodiment 6, wherein the pericarp comprises delta-Cadinene at a level above 1, 2, 3, 4, 5, 6, 7, 8, 9, 10, 15, 20, 25, 30, 35, 40, 50, 60, 100, 150, 200, 300 µg/g fresh fruit.

Embodiment 13

The *Capsicum* seed or plant grown therefrom, according to Embodiment 6, wherein the pericarp comprises 1,4-Cadinadiene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5.

Embodiment 14

The *Capsicum* seed or plant grown therefrom, according to Embodiment 6, wherein the pericarp comprises 1,4-Cadinadiene at a level above 1, 2, 3, 4, 5, 6, 7, 8, 9, 10, 15, 20, 25, 30, 35, 40, 50, 60, 100, 150, 200, 300 µg/g fresh fruit.

Embodiment 15

The *Capsicum* seed or plant grown therefrom, according to any one of Embodiments 1 to 14, wherein the pepper fruit comprises no capsaicinoid.

Embodiment 16

The *Capsicum* seed or plant grown therefrom, according to any one of Embodiments 1 to 14, wherein the pepper fruit comprises a lower level of capsaicinoid compared to *Capsicum annuum*.

Embodiment 17

The *Capsicum* seed or plant grown therefrom, according to any one of Embodiments 1 to 14, wherein the pepper fruit comprises a lower level of capsaicinoid compared to *Capsicum chinense*.

Embodiment 18

The *Capsicum* seed or plant grown therefrom, according to any one of Embodiments 1 to 14, wherein the pepper fruit comprises a pungency of zero Scoville Heat Unit (SHU).

Embodiment 19

The *Capsicum* seed or plant grown therefrom, according to any one of Embodiments 1 to 14, wherein the pepper fruit comprises a pungency of below 4000, 3000, 2000, 1000, 500, 250, 200, 150, 100, 50, 40, 30, 20, 10, or 5 Scoville Heat Units (SHUs).

Embodiment 20

The *Capsicum* seed or plant grown therefrom, according to any one of Embodiments 1 to 14, wherein the pericarp has a comparable level of the one or more aroma molecules than *Capsicum chinense* pericarp grown under similar conditions.

Embodiment 21

The *Capsicum* seed or plant grown therefrom, according to any one of Embodiments 1 to 14, wherein the pericarp has a higher level of the one or more aroma molecules than *Capsicum chinense* pericarp grown under similar conditions.

Embodiment 22

The *Capsicum* seed or plant grown therefrom, according to any one of Embodiments 1 to 14, wherein the *Capsicum* seed is a hybrid.

Embodiment 23

The *Capsicum* seed or plant grown therefrom, according to any one of Embodiments 1 to 14, wherein the *Capsicum* seed is an inbred.

Embodiment 24

The *Capsicum* seed or plant grown therefrom, according to any one of Embodiments 1 to 14, wherein the *Capsicum* seed or plant yields a seedless fruit.

Embodiment 25

The *Capsicum* seed or plant grown therefrom, according to any one of Embodiments 1 to 14, wherein the *Capsicum* seed is transgenic.

Embodiment 26

The *Capsicum* seed or plant grown therefrom, according to any one of Embodiments 1 to 14, wherein at least 70%, 75%, 77.5%, 80%, 82.5%, 85%, 86%, 87.5%, 90%, 92.5%, 95%, 97.5%, 98%, 99%, 99.5% of the *Capsicum* seed's nuclear genetic material is from a *C. annuum* background.

Embodiment 27

The *Capsicum* seed or plant grown therefrom, according to any one of Embodiments 1 to 14, wherein less than 30%, 25%, 20%, 15%, 14%, 13%, 12.5%, 10%, 7.5%, 5%, 2.5%, 2%, 1%, 0.5% of the *Capsicum* seed's nuclear genetic material is from a *C. chinense* background.

Embodiment 28

The *Capsicum* seed or plant grown therefrom, according to any one of Embodiments 1 to 14, wherein the *Capsicum* plant comprises one or more traits selected from the group consisting of resistance to geminivirus, resistance to *Xanthomonas*, resistance to aphids, resistance to powdery mildew, ease of fruit shedding, cold tolerance, having leaf hairs, thick fruit walls, flavor differences, and the clustering of seed-bearing placental tissue close to the stem of a fruit.

Embodiment 29

The *Capsicum* seed or plant grown therefrom, according to any one of Embodiments 1 to 14, wherein the pepper fruit has a shape selected from the group consisting of block, pointed, and round.

Embodiment 30

The *Capsicum* seed or plant grown therefrom, according to any one of Embodiments 1 to 14, wherein the pepper fruit has a color selected from the group consisting of green yellow, red, purple, black, brown, white, and orange

Embodiment 31

The *Capsicum* seed or plant grown therefrom, according to any one of Embodiments 1 to 14, wherein the *Capsicum* seed is a progeny of *Capsicum* line ZSP8T14-6274 or SVPS2625, wherein a representative sample of seed of the *Capsicum* line ZSP8T14-6274 has been deposited at ATCC under Accession No. PTA-122300, and wherein a representative sample of seed of the *Capsicum* line SVPS2625 has been deposited at ATCC under Accession No. PTA-122296.

Embodiment 32

The *Capsicum* seed or plant grown therefrom, according to any one of Embodiments 1 to 14, wherein the *Capsicum* seed is a $F_1$ progeny of *Capsicum* line ZSP8T14-6274 or SVPS2625, wherein a representative sample of seed of the *Capsicum* line ZSP8T14-6274 has been deposited at ATCC under Accession No. PTA-122300, and wherein a representative sample of seed of the *Capsicum* line SVPS2625 has been deposited at ATCC under Accession No. PTA-122296.

Embodiment 33

The *Capsicum* seed or plant grown therefrom, according to any one of Embodiments 1 to 14, wherein the *Capsicum* seed is a $F_2$ progeny of *Capsicum* line ZSP8T14-6274 or SVPS2625, wherein a representative sample of seed of the *Capsicum* line ZSP8T14-6274 has been deposited at ATCC under Accession No. PTA-122300, and wherein a representative sample of seed of the *Capsicum* line SVPS2625 has been deposited at ATCC under Accession No. PTA-122296.

Embodiment 34

The *Capsicum* seed or plant grown therefrom, according to any one of Embodiments 1 to 14, wherein the *Capsicum* seed is essentially derived from *Capsicum* line ZSP8T14-6274 or SVPS2625, wherein a representative sample of seed of the *Capsicum* line ZSP8T14-6274 has been deposited at ATCC under Accession No. PTA-122300, and wherein a representative sample of seed of the *Capsicum* line SVPS2625 has been deposited at ATCC under Accession No. PTA-122296.

Embodiment 35

The *Capsicum* seed or plant grown therefrom, according to any one of Embodiments 1 to 14, wherein the *Capsicum* seed comprises one or more introgressed loci from *Capsicum* line ZSP8T14-6274 or SVPS2625, wherein a representative sample of seed of the *Capsicum* line ZSP8T14-6274 has been deposited at ATCC under Accession No. PTA-122300, wherein a representative sample of seed of the *Capsicum* line SVPS2625 has been deposited at ATCC under Accession No. PTA-122296, and wherein the one or more introgressed loci provide genetic determinant for producing the one or more aroma molecules characteristic of *Capsicum chinense*.

Embodiment 36

The *Capsicum* seed or plant grown therefrom, according to any one of Embodiments 1 to 14, wherein the *Capsicum* plant exhibits a fruit comprising at maturity one or more aroma molecules characteristic of *Capsicum chinense* at a level equal to or higher than that of a *Capsicum* line when grown under similar conditions, wherein the *Capsicum* line is selected from the group consisting of lines ZSP8T14-6274 and SVPS2625, wherein a representative sample of seed of the *Capsicum* line ZSP8T14-6274 has been deposited at ATCC under Accession No. PTA-122300, wherein a representative sample of seed of the *Capsicum* line SVPS2625 has been deposited at ATCC under Accession No. PTA-122296.

Embodiment 37

A *Capsicum* seed or plant grown therefrom, wherein the *Capsicum* plant exhibits a pepper fruit at, or immediately prior to, maturity having pericarp comprising a total sugar content of at least 5.5% and alpha-Cubebene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5.

Embodiment 38

A *Capsicum* seed or plant grown therefrom, wherein the *Capsicum* plant exhibits a pepper fruit at, or immediately prior to, maturity having pericarp comprising a total sugar content of at least 5.5% and delta-Cadinene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5.

Embodiment 39

A *Capsicum* seed or plant grown therefrom, wherein the *Capsicum* plant exhibits a pepper fruit at, or immediately prior to, maturity having pericarp comprising a total sugar content of at least 5.5% and 1,4-Cadinadiene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5.

Embodiment 40

A *Capsicum* seed or plant grown therefrom, wherein the *Capsicum* plant exhibits a pepper fruit at, or immediately prior to, maturity having pericarp comprising a total sugar content of at least 5.5% and one or more terpene molecules selected from the group consisting of alpha-Cubebene at a level having a Relative GC/MS Response Score of at least 0.25, delta-Cadinene at a level having a Relative GC/MS Response Score of at least 0.25, 1,4-Cadinadiene at a level having a Relative GC/MS Response Score of at least 0.15, and any combination thereof.

Embodiment 41

The *Capsicum* seed or plant grown therefrom, according to any one of Embodiments 37 to 40, wherein the *Capsicum* is *Capsicum annuum*.

Embodiment 42

The *Capsicum* seed or plant grown therefrom, according to any one of Embodiments 37 to 40, wherein the pericarp comprises a titratable acidity at a higher level than that of pericarp of hybrid pepper PS09954859 grown under similar conditions.

Embodiment 43

The *Capsicum* seed or plant grown therefrom, according to any one of Embodiments 37 to 40, wherein the pericarp comprises a titratable acidity of at least 4.2, 4.3, 4.4, 4.5, 4.6, 4.7, 4.8, 4.9, 5.0, 5.1, 5.2, 5.3, 5.4, 5.5, 5.6, or 5.7 mmol $H^+$/100 g fresh tissue.

Embodiment 44

A container of *Capsicum* seeds according to any one of Embodiments 1 to 14.

Embodiment 45

A population of *Capsicum* plants according to any one of Embodiments 1 to 14.

Embodiment 46

A part of the *Capsicum* plant according to any one of Embodiments 1 to 14, wherein the part is selected from a cell, a protoplast, a leaf, pollen, an embryo, a root, a root tip, anther, a flower, a fruit, a pistil, a petiole, a meristem, a cotyledon, a hypocotyl, and a seed.

Embodiment 47

A sweet bell pepper fruit comprising at maturity one or more aroma molecules characteristic of *Capsicum chinense*, wherein the one or more aroma molecules are absent from pericarp of hybrid pepper PS09954859 or at a higher level than that of pericarp of hybrid pepper PS09954859 grown under similar conditions.

Embodiment 48

The sweet bell pepper fruit according to Embodiment 47, wherein the fruit comprises a total sugar content of at least 5.5%.

Embodiment 49

The sweet bell pepper fruit according to Embodiment 47, wherein the one or more aroma molecules are terpene molecules.

Embodiment 50

The sweet bell pepper fruit according to Embodiment 47, wherein the terpene molecules are selected from the group consisting of alpha-Cubebene, delta-Cadinene, and 1,4-Cadinadiene.

Embodiment 51

The sweet bell pepper fruit according to Embodiment 47, wherein the fruit comprises a titratable acidity at a higher level than that of a fruit of hybrid pepper PS09954859 grown under similar conditions.

Embodiment 52

The sweet bell pepper fruit according to Embodiment 47, wherein the fruit comprises a titratable acidity of at least 4.2, 4.3, 4.4, 4.5, 4.6, 4.7, 4.8, 4.9, 5.0, 5.1, 5.2, 5.3, 5.4, 5.5, 5.6, or 5.7 mmol $H^+$/100 g fresh tissue.

Embodiment 53

A method of producing a pepper fruit, the method comprising:
 a. cultivating a plant according to any one of Embodiments 1 to 14; and
 b. collecting a pepper fruit from the plant.

Embodiment 54

A method for producing a *Capsicum* plant capable of producing a sweet pepper fruit comprising one or more aroma molecules characteristic of *Capsicum chinense*, wherein the method comprises:
  a. crossing a *C. annuum* plant or hybrid with a *C. chinense* plant or hybrid to produce a population of progeny *Capsicum* plants; and
  b. selecting a progeny *Capsicum* plant comprising a *C. annuum* fruit type and producing a fruit at, or immediately prior to, maturity comprising one or more aroma molecules characteristic of *C. chinense*, wherein the one or more aroma molecules are selected from the group consisting of alpha-Cubebene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5; delta-Cadinene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5; 1,4-Cadinadiene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5; and any combinations thereof.

Embodiment 55

A method for producing a *Capsicum* plant capable of producing a sweet pepper fruit comprising one or more aroma molecules characteristic of *Capsicum chinense*, wherein the method comprises:
  c. crossing a *C. annuum* plant or hybrid with a *C. chinense* plant or hybrid to produce a population of progeny *Capsicum* plants; and
  d. selecting a progeny *Capsicum* plant comprising a *C. annuum* fruit type and producing a fruit at, or immediately prior to, maturity comprising one or more aroma molecules characteristic of *C. chinense*.

Embodiment 56

The method of Embodiment 55, wherein the method further comprises detecting one or more aroma molecules in fruits of the population of progeny *Capsicum* plants via GC/MS.

Embodiment 57

The method of Embodiment 55, wherein the one or more aroma molecules are terpene molecules.

Embodiment 58

The method of Embodiment 55, wherein the one or more aroma molecules are selected from the group consisting of alpha-Cubebene, delta-Cadinene, 1,4-Cadinadiene, and combinations thereof.

Embodiment 59

The method of Embodiment 55, wherein the one or more aroma molecules are alpha-Cubebene, delta-Cadinene, and 1,4-Cadinadiene.

Embodiment 60

The method of Embodiment 55, wherein the fruit of the selected progeny *Capsicum* plant comprises alpha-Cubebene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5.

Embodiment 61

The method of Embodiment 55, wherein the fruit of the selected progeny *Capsicum* plant comprises delta-Cadinene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5.

Embodiment 62

The method of Embodiment 55, wherein the fruit of the selected progeny *Capsicum* plant comprises 1,4-Cadinadiene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5.

Embodiment 63

The method of Embodiment 55, wherein the selected progeny *Capsicum* plant is capable of producing a fruit having a total sugar content of at least 5.5%.

Embodiment 64

The method of Embodiment 55, wherein the method further comprises:
  e. backcrossing the selected progeny *Capsicum* plant with the *C. annuum* plant to produce a population of further progeny *Capsicum* plants.

Embodiment 65

The method of Embodiment 55, wherein the method further comprises:
  f. selecting a further progeny *Capsicum* plant comprising a *C. annuum* fruit type and producing a fruit comprising one or more aroma molecules characteristic of *C. chinense*.

Embodiment 66

The method of Embodiment 55, wherein the *C. annuum* plant or hybrid is male sterile.

Embodiment 67

The method of Embodiment 55, wherein the *C. annuum* plant or hybrid is cytoplasmic male sterile.

Embodiment 68

The method of Embodiment 55, wherein the *C. chinense* plant or hybrid is male sterile.

Embodiment 69

The method of Embodiment 55, wherein the *C. chinense* plant or hybrid is cytoplasmic male sterile.

Embodiment 70

A method for selecting a sweet pepper fruit comprising one or more aroma molecules characteristic of *Capsicum chinense*, wherein the method comprises:
a. obtaining a sweet pepper fruit;
b. detecting in the sweet pepper fruit one or more aroma molecules selected from the group consisting of alpha-Cubebene, delta-Cadinene, 1,4-Cadinadiene, and combinations thereof.

Embodiment 71

A method for introducing a desired *Capsicum chinense* specific aroma molecule into a sweet pepper plant, wherein the desired *Capsicum chinense* specific aroma molecule is selected from the group consisting of alpha-Cubebene, delta-Cadinene, 1,4-Cadinadiene, and any combinations thereof, the method comprising:
a. Crossing a sweet pepper plant with a plant selected from the group consisting of *Capsicum* line ZSP8T14-6274, a representative sample seed of which line having been deposited at ATCC under Accession No. PTA-122300, a progeny line of *Capsicum* line ZSP8T14-6274, *Capsicum* line SVPS2625, a representative sample of seed of which line having been deposited at ATCC under Accession No. PTA-122296, and a progeny line of *Capsicum* line SVPS2625,
b. selecting an $F_1$ progeny pepper plant comprising the desired *Capsicum chinense* specific aroma molecule in a fruit at, or immediately prior to, maturity;
c. backcrossing the $F_1$ progeny to the sweet pepper plant;
d. selecting a backcrossed progeny pepper plant comprising the desired *Capsicum chinense* specific aroma molecule;
e. repeating steps (c) and (d) three or more times in succession to produce selected fourth or higher backcross progeny that comprise the desired *Capsicum chinense* specific aroma molecule.

Embodiment 72

The method of Embodiment 71, wherein the desired *Capsicum chinense* specific aroma molecule is selected from the group consisting of alpha-Cubebene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5; delta-Cadinene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5; 1,4-Cadinadiene at a level having a Relative GC/MS Response Score of at least 0.05, 0.08, 0.1, 0.12, 0.15, 0.18, 0.2, 0.25, 0.3, 0.4, 0.5, 0.6, 0.7, 0.8, 0.9, 1.0, 1.5, 2.0, 2.5, 3.0, 4.0, 5.0, 7.5, 10.0, 12.5, 15.0, or 17.5; and any combinations thereof.

Embodiment 73

A method for producing a *Capsicum* plant exhibiting a sweet pepper fruit comprising one or more desirable aromas, wherein the method comprises:
c. crossing a *C. annuum* plant or hybrid with a *Capsicum* plant or hybrid capable of producing a fruit exhibiting the one or more desirable aromas to produce a population of progeny *Capsicum* plants; and
d. selecting a progeny *Capsicum* plant comprising a *C. annuum* fruit type and exhibiting a fruit comprising the one or more desirable aromas.

Embodiment 74

The method of Embodiment 73, wherein the method comprises detecting the one or more desirable aromas via GC/MS.

Embodiment 75

The method of Embodiment 73, wherein the one or more desirable aromas comprise terpene molecules.

Embodiment 76

The method of Embodiment 73, wherein the one or more desirable aromas comprise a terpene are selected from the group consisting of alpha-Cubebene, delta-Cadinene, 1,4-Cadinadiene, and combinations thereof.

Embodiment 77

The method of Embodiment 73, wherein the one or more desirable aromas comprise alpha-Cubebene, delta-Cadinene, and 1,4-Cadinadiene.

Embodiment 78

The method of Embodiment 73, wherein the method further comprises genotyping the Pun1 locus in the selected progeny *Capsicum* plant.

Embodiment 79

The method of Embodiment 73, wherein the genotyping further comprises detecting a pun1-1 allele.

Embodiment 80

A *Capsicum* plant or seed capable of producing a pepper fruit comprising at or near maturity a total sugar content of at least 5.5%, 6.0%, 6.5%, 7.0%, 7.5%, 8.0%, 8.5%, or 9% and a Brix rating of at least 8.0, 8.5, 9.0, or 9.5.

Embodiment 81

The *Capsicum* plant or seed capable of producing a pepper fruit of Embodiment 80, wherein the fruit is preferred by at least 30%, 35%, 40%, 45%, 50%, 55%, 60%, or 65% more consumers when compared to a commercially available or morphologically comparable sweet pepper fruit in a test of consumer preference.

Embodiment 82

The *Capsicum* plant or seed capable of producing a pepper fruit of Embodiment 81, wherein the fruit is described by at least 30%, 35%, 40%, 45%, 50%, 55%, 60%, 70%, 75%, or 80% more consumers in a test of consumer preference as more flavorful, more sweet, and less bitter when compared to a commercially available or morphologically comparable sweet pepper fruit.

Embodiment 83

The *Capsicum* plant or seed capable of producing a pepper fruit of Embodiment 80, wherein the fruit scores at least 20% higher than a commercially available or morphologically comparable sweet pepper fruit based on a consumer graded hedonic attribute test for one or more categories selected from the group consisting of overall rating, flavor, and sweetness.

Embodiment 84

The *Capsicum* plant or seed capable of producing a pepper fruit of Embodiment 80, wherein the fruit scores at least 5.5, 6.0, or 6.5 for one or more categories selected from the group consisting of overall rating, flavor, and sweetness based on a consumer graded hedonic attribute test.

Embodiment 85

The *Capsicum* fruit comprising a total sugar content of at least 5.5%, 6.0%, 6.5%, or 7.0% and a Brix rating of at least 8.0, 8.5, 9.0, or 9.5 at or near maturity.

Embodiment 86

The *Capsicum* fruit of Embodiment 85, wherein the fruit is preferred by at least 30%, 35%, 40%, 45%, 50%, 55%, 60%, or 65% more consumers when compared to a commercially available or morphologically comparable sweet pepper fruit in a test of consumer preference.

Embodiment 87

The *Capsicum* fruit of Embodiment 86, wherein the fruit is described by at least 30%, 35%, 40%, 45%, 50%, 55%, 60%, 70%, 75%, or 80% more consumers in a test of consumer preference as more flavorful, more sweet, and less bitter when compared to a commercially available or morphologically comparable sweet pepper fruit.

Embodiment 88

The *Capsicum* fruit of Embodiment 85, wherein the fruit scores at least 20% higher than a commercially available sweet pepper fruit based on a consumer graded hedonic attribute test for one or more categories selected from the group consisting of overall rating, flavor, and sweetness.

Embodiment 89

The *Capsicum* fruit of Embodiment 85, wherein the fruit scores at least 5.5, 6.0, or 6.5 for one or more categories selected from the group consisting of overall rating, flavor, and sweetness based on a consumer graded hedonic attribute test.

Embodiment 90

A *Capsicum* seed or plant grown therefrom, capable of producing a pepper fruit comprising at, or immediately prior to, maturity a pericarp comprising a total sugar content of at least 5.5%, 6.0%, 6.5%, 7.5%, 8.5%, 9%, or 9.5% and one or more aroma molecules characteristic of *Capsicum chinense*, wherein the *Capsicum* plant shares a genetic determinant with *Capsicum* line SVPS2625, a sample seed of which having been deposited at ATCC under Accession No. PTA-122296; wherein the genetic determinant provides a total sugar level of at least 5.5%, 6.0%, 6.5%, 7.5%, 8.5%, 9%, or 9.5%, a desired *Capsicum chinense* specific aroma molecule, or both.

Embodiment 91

A *Capsicum* seed or plant grown therefrom, capable of producing a pepper fruit comprising at, or immediately prior to, maturity a pericarp comprising a total sugar content of at least 5.5%, 6.0%, 6.5%, 7.5%, 8.5%, 9%, or 9.5% and one or more aroma molecules characteristic of *Capsicum chinense*, wherein a genetic determinant providing said total sugar level of at least 5.5% or said desired *Capsicum chinense* specific aroma molecule is also present in SVPS2625, a sample seed of which having been deposited at ATCC under Accession No. PTA-122296.

Embodiment 92

The *Capsicum* seed or plant grown therefrom, of Embodiment 90 or 91, wherein the desired *Capsicum chinense* specific aroma molecule is selected from the group consisting of alpha-Cubebene, delta-Cadinene, 1,4-Cadinadiene.

Embodiment 93

A *Capsicum* seed or plant grown therefrom, capable of producing a pepper fruit exhibiting at, or immediately prior to, maturity a pericarp comprising one or more aroma molecules characteristic of *Capsicum chinense*, wherein the *Capsicum* plant is a progeny of *Capsicum* line ZSP8T14-6274, wherein a representative sample seed *Capsicum* line ZSP8T14-6274 has been deposited at ATCC under Accession No. PTA-122300.

Embodiment 94

The *Capsicum* seed or plant grown therefrom, of Embodiment 93, further comprising a total sugar content of at least 5.5%, 6.0%, 6.5%, 7.5%, 8.5%, 9%, or 9.5%.

Embodiment 95

The *Capsicum* seed or plant grown therefrom of Embodiment 93, wherein the *Capsicum* seed or plant shares with ZSP8T14-6274 a genetic determinant providing for the desired *Capsicum chinense* specific aroma molecule.

Embodiment 96

The *Capsicum* seed or plant grown therefrom of Embodiment 95, wherein the desired *Capsicum chinense* specific aroma molecule is selected from the group consisting of alpha-Cubebene, delta-Cadinene, 1,4-Cadinadiene.

Embodiment 97

A *Capsicum* plant, or part thereof, capable of producing a pepper fruit at, or immediately prior to, maturity comprising a pericarp comprising a total sugar content of at least 5.5%, 6.0%, 6.5%, 7.5%, 8.5%, 9%, or 9.5%, wherein the *Capsicum* plant is a progeny of *Capsicum* line SMO8T14-6275.

Embodiment 98

The *Capsicum* plant, or part thereof, of Embodiment 97, wherein the *Capsicum* plant comprises a genetic determinant from SMO8T14-6275 providing for a total sugar level of at least 5.5%, 6.0%, 6.5%, 7.5%, 8.5%, 9%, or 9.5%.

Embodiment 99

The *Capsicum* plant, or part thereof, of Embodiment 97, wherein the *Capsicum* plant is homozygous for the SMO2 and SMO3 QTLs, wherein the SMO2 QTL is identifiable by markers SEQ ID NO: 1 or 2, and wherein the SMO3 QTL is identifiable by markers SEQ ID NO: 3 or 4.

Embodiment 100

The *Capsicum* plant, or part thereof, of Embodiment 97, wherein the *Capsicum* plant is heterozygous for the SMO2 and SMO3 QTLs, wherein the SMO2 QTL is identifiable by markers SEQ ID NO: 1 or 2, and wherein the SMO3 QTL is identifiable by markers SEQ ID NO: 3 or 4.

Embodiment 101

The *Capsicum* plant, or part thereof, according to Embodiment 80 or 85, wherein the pepper plant is heterozygous for the QTL SMO2 identifiable by markers SEQ ID NO: 1 or 2.

Embodiment 102

The *Capsicum* plant, or part thereof, according to Embodiment 80 or 85, wherein the pepper plant is heterozygous for the QTL SMO3 identifiable by markers SEQ ID NO: 3 or 4.

Embodiment 103

A method to obtain a *Capsicum* plant, comprising:
a. isolating a nucleic acid molecule from a *Capsicum* plant,
b. assaying the isolated nucleic acid molecule for a marker molecule associated with a SMO2 QTL, where the marker molecule is within 10 centimorgans or less from a marker selected from the group consisting of SEQ ID NO: 1 and SEQ ID NO: 2, and
c. selecting a *Capsicum* plant based on the genotyping that comprises the marker molecule, thereby selecting a SMO2 containing *Capsicum* plant.

Embodiment 104

The method of Embodiment 103, wherein the marker molecule is within 8 centimorgans or less from a marker selected from the group consisting of SEQ ID NO: 1 and SEQ ID NO: 2.

Embodiment 105

The method of Embodiment 103, wherein the marker molecule is within 5 centimorgans or less from a marker selected from the group consisting of SEQ ID NO: 1 and SEQ ID NO: 2.

Embodiment 106

The method of Embodiment 103, wherein the marker molecule is within 3 centimorgans or less from a marker selected from the group consisting of SEQ ID NO: 1 and SEQ ID NO: 2.

Embodiment 107

The method of Embodiment 103, wherein the marker molecule is within 2 centimorgans or less from a marker selected from the group consisting of SEQ ID NO: 1 and SEQ ID NO: 2.

Embodiment 108

The method of Embodiment 103, wherein the marker molecule is within 1 centimorgans or less from a marker selected from the group consisting of SEQ ID NO: 1 and SEQ ID NO: 2.

Embodiment 109

A method to obtain a *Capsicum* plant, comprising:
a. isolating a nucleic acid molecule from a *Capsicum* plant,
b. assaying the isolated nucleic acid molecule for a marker molecule associated with a SMO3 QTL, where the marker molecule is within 10 centimorgans or less from a marker selected from the group consisting of SEQ ID NO: 3 and SEQ ID NO: 4, and
c. selecting a *Capsicum* plant based on the genotyping that comprises the marker molecule, thereby selecting a SMO3 containing *Capsicum* plant.

Embodiment 110

The method of Embodiment 109, wherein the marker molecule is within 8 centimorgans or less from a marker selected from the group consisting of SEQ ID NO: 3 and SEQ ID NO: 4.

Embodiment 111

The method of Embodiment 109, wherein the marker molecule is within 5 centimorgans or less from a marker selected from the group consisting of SEQ ID NO: 3 and SEQ ID NO: 4.

Embodiment 112

The method of Embodiment 109, wherein the marker molecule is within 3 centimorgans or less from a marker selected from the group consisting of SEQ ID NO: 3 and SEQ ID NO: 4.

Embodiment 113

The method of Embodiment 109, wherein the marker molecule is within 2 centimorgans or less from a marker selected from the group consisting of SEQ ID NO: 3 and SEQ ID NO: 4.

Embodiment 114

The method of Embodiment 109, wherein the marker molecule is within 1 centimorgans or less from a marker selected from the group consisting of SEQ ID NO: 3 and SEQ ID NO: 4.

Embodiment 115

A method comprising:
a. obtaining a population of *Capsicum* plants,
b. genotyping the population using a marker molecule associated with a SMO2 QTL, where the marker molecule is within 10 centimorgans or less from a marker selected from the group consisting of SEQ ID NO: 1 and SEQ ID NO: 2,
c. selecting a *Capsicum* plant based on the genotyping, and
d. producing a progeny from the selected *Capsicum* plant.

Embodiment 116

The method of Embodiment 115, wherein the marker molecule is within 8 centimorgans or less from a marker selected from the group consisting of SEQ ID NO: 1 and SEQ ID NO: 2.

Embodiment 117

The method of Embodiment 115, wherein the marker molecule is within 5 centimorgans or less from a marker selected from the group consisting of SEQ ID NO: 1 and SEQ ID NO: 2.

Embodiment 118

The method of Embodiment 115, wherein the marker molecule is within 3 centimorgans or less from a marker selected from the group consisting of SEQ ID NO: 1 and SEQ ID NO: 2.

Embodiment 119

The method of Embodiment 115, wherein the marker molecule is within 2 centimorgans or less from a marker selected from the group consisting of SEQ ID NO: 1 and SEQ ID NO: 2.

Embodiment 120

The method of Embodiment 115, wherein the marker molecule is within 1 centimorgans or less from a marker selected from the group consisting of SEQ ID NO: 1 and SEQ ID NO: 2.

Embodiment 121

A method comprising:
a. obtaining a population of *Capsicum* plants,
b. genotyping the population using a marker molecule associated with a SMO3 QTL, where the marker molecule is within 10 centimorgans or less from a marker selected from the group consisting of SEQ ID NO: 3 and SEQ ID NO: 4,
c. selecting a *Capsicum* plant based on the genotyping, and
d. producing a progeny from the selected *Capsicum* plant.

Embodiment 122

The method of Embodiment 121 wherein the marker molecule is within 8 centimorgans or less from a marker selected from the group consisting of SEQ ID NO: 3 and SEQ ID NO: 4.

Embodiment 123

The method of Embodiment 121, wherein the marker molecule is within 5 centimorgans or less from a marker selected from the group consisting of SEQ ID NO: 3 and SEQ ID NO: 4.

Embodiment 124

The method of Embodiment 121, wherein the marker molecule is within 3 centimorgans or less from a marker selected from the group consisting of SEQ ID NO: 3 and SEQ ID NO: 4.

Embodiment 125

The method of Embodiment 121, wherein the marker molecule is within 2 centimorgans or less from a marker selected from the group consisting of SEQ ID NO: 3 and SEQ ID NO: 4.

Embodiment 126

The method of Embodiment 121, wherein the marker molecule is within 1 centimorgans or less from a marker selected from the group consisting of SEQ ID NO: 3 and SEQ ID NO: 4.

Embodiment 127

A method comprising:
a. obtaining a *Capsicum* plant of Embodiment 80 or 85, and
b. genotyping the *Capsicum* plant using a marker molecule associated with a SMO2 QTL, where the marker molecule is within 10 centimorgans or less from a marker selected from the group consisting of SEQ ID NO: 1 and SEQ ID NO: 2.

Embodiment 128

The method of Embodiment 127, wherein the marker molecule is within 8 centimorgans or less from a marker selected from the group consisting of SEQ ID NO: 1 and SEQ ID NO: 2.

Embodiment 129

The method of Embodiment 127, wherein the marker molecule is within 5 centimorgans or less from a marker selected from the group consisting of SEQ ID NO: 1 and SEQ ID NO: 2.

Embodiment 130

The method of Embodiment 127, wherein the marker molecule is within 3 centimorgans or less from a marker selected from the group consisting of SEQ ID NO: 1 and SEQ ID NO: 2.

Embodiment 131

The method of Embodiment 127, wherein the marker molecule is within 2 centimorgans or less from a marker selected from the group consisting of SEQ ID NO: 1 and SEQ ID NO: 2.

Embodiment 132

The method of Embodiment 127, wherein the marker molecule is within 1 centimorgans or less from a marker selected from the group consisting of SEQ ID NO: 1 and SEQ ID NO: 2.

Embodiment 133

A method comprising:
a. obtaining a *Capsicum* plant of Embodiment 80 or 85, and
b. genotyping the *Capsicum* plant using a marker molecule associated with a SMO3 QTL, where the marker molecule is within 10 centimorgans or less from a marker selected from the group consisting of SEQ ID NO: 3 and SEQ ID NO: 4.

Embodiment 134

The method of Embodiment 133, wherein the marker molecule is within 8 centimorgans or less from a marker selected from the group consisting of SEQ ID NO: 3 and SEQ ID NO: 4.

Embodiment 135

The method of Embodiment 133, wherein the marker molecule is within 5 centimorgans or less from a marker selected from the group consisting of SEQ ID NO: 3 and SEQ ID NO: 4.

Embodiment 136

The method of Embodiment 133, wherein the marker molecule is within 3 centimorgans or less from a marker selected from the group consisting of SEQ ID NO: 3 and SEQ ID NO: 4.

Embodiment 137

The method of Embodiment 133, wherein the marker molecule is within 2 centimorgans or less from a marker selected from the group consisting of SEQ ID NO: 3 and SEQ ID NO: 4.

Embodiment 138

The method of Embodiment 133, wherein the marker molecule is within 1 centimorgans or less from a marker selected from the group consisting of SEQ ID NO: 3 and SEQ ID NO: 4.

Embodiment 139

The method of Embodiment 103, 115, or 127, wherein the marker molecule is in a genomic region flanked by SEQ ID NOs: 1 and 2.

Embodiment 140

The method of Embodiment 109, 121, or 133, wherein the marker molecule is in a genomic region flanked by SEQ ID NOs: 3 and 4.

Embodiment 141

A method to obtain a *Capsicum* plant, comprising:
a. isolating a nucleic acid molecule from a *Capsicum* plant,
b. assaying the isolated nucleic acid molecule for a marker molecule associated with a SMO8 QTL, where the marker molecule is within 10 centimorgans or less from a marker selected from the group consisting of SEQ ID NO: 5 and SEQ ID NO: 6, and
c. selecting a *Capsicum* plant based on the genotyping that comprises the marker molecule, thereby selecting a SMO8 containing *Capsicum* plant.

Embodiment 142

The method of Embodiment 141, wherein the marker molecule is within 8 centimorgans or less from a marker selected from the group consisting of SEQ ID NO: 5 and SEQ ID NO: 6.

Embodiment 143

The method of Embodiment 141, wherein the marker molecule is within 5 centimorgans or less from a marker selected from the group consisting of SEQ ID NO: 5 and SEQ ID NO: 6.

Embodiment 144

The method of Embodiment 141, wherein the marker molecule is within 3 centimorgans or less from a marker selected from the group consisting of SEQ ID NO: 5 and SEQ ID NO: 6.

Embodiment 145

The method of Embodiment 141, wherein the marker molecule is within 2 centimorgans or less from a marker selected from the group consisting of SEQ ID NO: 5 and SEQ ID NO: 6.

Embodiment 146

The method of Embodiment 141, wherein the marker molecule is within 1 centimorgans or less from a marker selected from the group consisting of SEQ ID NO: 5 and SEQ ID NO: 6.

Embodiment 147

The method of Embodiment 141, wherein the marker molecule is in a genomic region flanked by SEQ ID NOs: 5 and 6.

Embodiment 148

A method to obtain a *Capsicum* plant, comprising:
a. isolating a nucleic acid molecule from a *Capsicum* plant,
b. assaying the isolated nucleic acid molecule for a marker molecule associated with a SZZ3 QTL, where the marker molecule is within 10 centimorgans or less from a marker selected from the group consisting of SEQ ID NO: 7 and SEQ ID NO: 8, and
c. selecting a *Capsicum* plant based on the genotyping that comprises the marker molecule, thereby selecting a SZZ3 containing *Capsicum* plant.

Embodiment 149

The method of Embodiment 148, wherein the marker molecule is within 8 centimorgans or less from a marker selected from the group consisting of SEQ ID NO: 7 and SEQ ID NO: 8.

Embodiment 150

The method of Embodiment 148, wherein the marker molecule is within 5 centimorgans or less from a marker selected from the group consisting of SEQ ID NO: 7 and SEQ ID NO: 8.

Embodiment 151

The method of Embodiment 148, wherein the marker molecule is within 3 centimorgans or less from a marker selected from the group consisting of SEQ ID NO: 7 and SEQ ID NO: 8.

Embodiment 152

The method of Embodiment 148, wherein the marker molecule is within 2 centimorgans or less from a marker selected from the group consisting of SEQ ID NO: 7 and SEQ ID NO: 8.

Embodiment 153

The method of Embodiment 148, wherein the marker molecule is within 1 centimorgans or less from a marker selected from the group consisting of SEQ ID NO: 7 and SEQ ID NO: 8.

Embodiment 154

The method of Embodiment 148, wherein the marker molecule is in a genomic region flanked by SEQ ID NOs: 7 and 8.

Embodiment 155

A method to obtain a *Capsicum* plant, comprising:
a. isolating a nucleic acid molecule from a *Capsicum* plant,
b. assaying the isolated nucleic acid molecule for a marker molecule associated with a SZZ4 QTL, where the marker molecule is within 10 centimorgans or less from a marker selected from the group consisting of SEQ ID NO: 9 and SEQ ID NO: 10, and
c. selecting a *Capsicum* plant based on the genotyping that comprises the marker molecule, thereby selecting a SZZ4 containing *Capsicum* plant.

Embodiment 156

The method of Embodiment 155, wherein the marker molecule is within 8 centimorgans or less from a marker selected from the group consisting of SEQ ID NO: 9 and SEQ ID NO: 10.

Embodiment 157

The method of Embodiment 155, wherein the marker molecule is within 5 centimorgans or less from a marker selected from the group consisting of SEQ ID NO: 9 and SEQ ID NO: 10.

Embodiment 158

The method of Embodiment 155, wherein the marker molecule is within 3 centimorgans or less from a marker selected from the group consisting of SEQ ID NO: 9 and SEQ ID NO: 10.

Embodiment 159

The method of Embodiment 155, wherein the marker molecule is within 2 centimorgans or less from a marker selected from the group consisting of SEQ ID NO: 9 and SEQ ID NO: 10.

Embodiment 160

The method of Embodiment 155, wherein the marker molecule is within 1 centimorgans or less from a marker selected from the group consisting of SEQ ID NO: 9 and SEQ ID NO: 10.

Embodiment 161

The method of Embodiment 155, wherein the marker molecule is in a genomic region flanked by SEQ ID NOs: 9 and 10.

Embodiment 162

A method to obtain a *Capsicum* plant, comprising:
a. isolating a nucleic acid molecule from a *Capsicum* plant,
b. assaying the isolated nucleic acid molecule for a marker molecule associated with a SZZ11 QTL, where the marker molecule is within 10 centimorgans or less from a marker selected from the group consisting of SEQ ID NO: 11 and SEQ ID NO: 12, and
c. selecting a *Capsicum* plant based on the genotyping that comprises the marker molecule, thereby selecting a SZZ11 containing *Capsicum* plant.

Embodiment 163

The method of Embodiment 162, wherein the marker molecule is within 8 centimorgans or less from a marker selected from the group consisting of SEQ ID NO: 11 and SEQ ID NO: 12.

Embodiment 164

The method of Embodiment 162, wherein the marker molecule is within 5 centimorgans or less from a marker selected from the group consisting of SEQ ID NO: 11 and SEQ ID NO: 12.

Embodiment 165

The method of Embodiment 162, wherein the marker molecule is within 3 centimorgans or less from a marker selected from the group consisting of SEQ ID NO: 11 and SEQ ID NO: 12.

Embodiment 166

The method of Embodiment 162, wherein the marker molecule is within 2 centimorgans or less from a marker selected from the group consisting of SEQ ID NO: 11 and SEQ ID NO: 12.

Embodiment 167

The method of Embodiment 162, wherein the marker molecule is within 1 centimorgans or less from a marker selected from the group consisting of SEQ ID NO: 11 and SEQ ID NO: 12.

Embodiment 168

The method of Embodiment 162, wherein the marker molecule is in a genomic region flanked by SEQ ID NOs: 11 and 12.

Embodiment 169

A method to obtain a *Capsicum* plant comprising:
a. isolating a nucleic acid molecule from a *Capsicum* plant,
b. assaying the isolated nucleic acid molecule for a marker molecule associated with a SHY1 QTL, where the marker molecule is within 10 centimorgans or less from a marker selected from the group consisting of SEQ ID NO: 13 and SEQ ID NO: 14, and
c. selecting a *Capsicum* plant based on the genotyping that comprises the marker molecule, thereby selecting a SHY1 containing *Capsicum* plant.

Embodiment 170

The method of Embodiment 169, wherein the marker molecule is within 8 centimorgans or less from a marker selected from the group consisting of SEQ ID NO: 13 and SEQ ID NO: 14.

Embodiment 171

The method of Embodiment 169, wherein the marker molecule is within 5 centimorgans or less from a marker selected from the group consisting of SEQ ID NO: 13 and SEQ ID NO: 14.

Embodiment 172

The method of Embodiment 169, wherein the marker molecule is within 3 centimorgans or less from a marker selected from the group consisting of SEQ ID NO: 13 and SEQ ID NO: 14.

Embodiment 173

The method of Embodiment 169, wherein the marker molecule is within 2 centimorgans or less from a marker selected from the group consisting of SEQ ID NO: 13 and SEQ ID NO: 14.

Embodiment 174

The method of Embodiment 169, wherein the marker molecule is within 1 centimorgans or less from a marker selected from the group consisting of SEQ ID NO: 13 and SEQ ID NO: 14.

Embodiment 175

The method of Embodiment 169, wherein the marker molecule is in a genomic region flanked by SEQ ID NOs: 13 and 14.

Embodiment 176

A method to obtain a *Capsicum* plant, comprising:
a. isolating a nucleic acid molecule from a *Capsicum* plant,
b. assaying the isolated nucleic acid molecule for a marker molecule associated with a SHY12 QTL, where the marker molecule is within 10 centimorgans or less from a marker selected from the group consisting of SEQ ID NO: 15 and SEQ ID NO: 16, and
c. selecting a *Capsicum* plant based on the genotyping that comprises the marker molecule, thereby selecting a SHY12 containing *Capsicum* plant.

Embodiment 177

The method of Embodiment 176, wherein the marker molecule is within 8 centimorgans or less from a marker selected from the group consisting of SEQ ID NO: 15 and SEQ ID NO: 16.

Embodiment 178

The method of Embodiment 176, wherein the marker molecule is within 5 centimorgans or less from a marker selected from the group consisting of SEQ ID NO: 15 and SEQ ID NO: 16.

Embodiment 179

The method of Embodiment 176, wherein the marker molecule is within 3 centimorgans or less from a marker selected from the group consisting of SEQ ID NO: 15 and SEQ ID NO: 16.

Embodiment 180

The method of Embodiment 176, wherein the marker molecule is within 2 centimorgans or less from a marker selected from the group consisting of SEQ ID NO: 15 and SEQ ID NO: 16.

Embodiment 181

The method of Embodiment 176, wherein the marker molecule is within 1 centimorgans or less from a marker selected from the group consisting of SEQ ID NO: 15 and SEQ ID NO: 16.

Embodiment 182

The method of Embodiment 176, wherein the marker molecule is in a genomic region flanked by SEQ ID NOs: 15 and 16.

Embodiment 183

A method comprising:
a. obtaining a population of *Capsicum* plants,
b. genotyping the population using a marker molecule associated with a SMO8 QTL, where the marker molecule is within 10 centimorgans or less from a marker selected from the group consisting of SEQ ID NO: 5 and SEQ ID NO: 6,
c. selecting a *Capsicum* plant based on the genotyping, and
d. producing a progeny from the selected *Capsicum* plant.

Embodiment 184

The method of Embodiment 183, wherein the marker molecule is within 8 centimorgans or less from a marker selected from the group consisting of SEQ ID NO: 5 and SEQ ID NO: 6.

Embodiment 185

The method of Embodiment 183, wherein the marker molecule is within 5 centimorgans or less from a marker selected from the group consisting of SEQ ID NO: 5 and SEQ ID NO: 6.

Embodiment 186

The method of Embodiment 183, wherein the marker molecule is within 3 centimorgans or less from a marker selected from the group consisting of SEQ ID NO: 5 and SEQ ID NO: 6.

Embodiment 187

The method of Embodiment 183, wherein the marker molecule is within 2 centimorgans or less from a marker selected from the group consisting of SEQ ID NO: 5 and SEQ ID NO: 6.

Embodiment 188

The method of Embodiment 183, wherein the marker molecule is within 1 centimorgans or less from a marker selected from the group consisting of SEQ ID NO: 5 and SEQ ID NO: 6.

Embodiment 189

The method of Embodiment 183, wherein the marker molecule is in a genomic region flanked by SEQ ID NOs: 5 and 6.

Embodiment 190

A method comprising:
a. obtaining a population of *Capsicum* plants,
b. genotyping the population using a marker molecule associated with a SZZ3 QTL, where the marker molecule is within 10 centimorgans or less from a marker selected from the group consisting of SEQ ID NO: 7 and SEQ ID NO: 8,
c. selecting a *Capsicum* plant based on the genotyping, and
d. producing a progeny from the selected *Capsicum* plant.

Embodiment 191

The method of Embodiment 190, wherein the marker molecule is within 8 centimorgans or less from a marker selected from the group consisting of SEQ ID NO: 7 and SEQ ID NO: 8.

Embodiment 192

The method of Embodiment 190, wherein the marker molecule is within 5 centimorgans or less from a marker selected from the group consisting of SEQ ID NO: 7 and SEQ ID NO: 8.

Embodiment 193

The method of Embodiment 190, wherein the marker molecule is within 3 centimorgans or less from a marker selected from the group consisting of SEQ ID NO: 7 and SEQ ID NO: 8.

Embodiment 194

The method of Embodiment 190, wherein the marker molecule is within 2 centimorgans or less from a marker selected from the group consisting of SEQ ID NO: 7 and SEQ ID NO: 8.

Embodiment 195

The method of Embodiment 190, wherein the marker molecule is within 1 centimorgans or less from a marker selected from the group consisting of SEQ ID NO: 7 and SEQ ID NO: 8.

Embodiment 196

The method of Embodiment 190, wherein the marker molecule is in a genomic region flanked by SEQ ID NOs: 7 and 8.

Embodiment 197

A method comprising:
a. obtaining a population of *Capsicum* plants,
b. genotyping the population using a marker molecule associated with a SZZ4 QTL, where the marker molecule is within 10 centimorgans or less from a marker selected from the group consisting of SEQ ID NO: 9 and SEQ ID NO: 10,
c. selecting a *Capsicum* plant based on the genotyping, and
d. producing a progeny from the selected *Capsicum* plant.

Embodiment 198

The method of Embodiment 197, wherein the marker molecule is within 8 centimorgans or less from a marker selected from the group consisting of SEQ ID NO: 9 and SEQ ID NO: 10.

Embodiment 199

The method of Embodiment 197, wherein the marker molecule is within 5 centimorgans or less from a marker selected from the group consisting of SEQ ID NO: 9 and SEQ ID NO: 10.

Embodiment 200

The method of Embodiment 197, wherein the marker molecule is within 3 centimorgans or less from a marker selected from the group consisting of SEQ ID NO: 9 and SEQ ID NO: 10.

Embodiment 201

The method of Embodiment 197, wherein the marker molecule is within 2 centimorgans or less from a marker selected from the group consisting of SEQ ID NO: 9 and SEQ ID NO: 10.

Embodiment 202

The method of Embodiment 197, wherein the marker molecule is within 1 centimorgans or less from a marker selected from the group consisting of SEQ ID NO: 9 and SEQ ID NO: 10.

Embodiment 203

The method of Embodiment 197, wherein the marker molecule is in a genomic region flanked by SEQ ID NOs: 9 and 10.

Embodiment 204

A method comprising:
a. obtaining a population of *Capsicum* plants,
b. genotyping the population using a marker molecule associated with a SZZ11 QTL, where the marker molecule is within 10 centimorgans or less from a marker selected from the group consisting of SEQ ID NO: 11 and SEQ ID NO: 12,
c. selecting a *Capsicum* plant based on the genotyping, and
d. producing a progeny from the selected *Capsicum* plant.

Embodiment 205

The method of Embodiment 204, wherein the marker molecule is within 8 centimorgans or less from a marker selected from the group consisting of SEQ ID NO: 11 and SEQ ID NO: 12.

Embodiment 206

The method of Embodiment 204, wherein the marker molecule is within 5 centimorgans or less from a marker selected from the group consisting of SEQ ID NO: 11 and SEQ ID NO: 12.

Embodiment 207

The method of Embodiment 204, wherein the marker molecule is within 3 centimorgans or less from a marker selected from the group consisting of SEQ ID NO: 11 and SEQ ID NO: 12.

Embodiment 208

The method of Embodiment 204, wherein the marker molecule is within 2 centimorgans or less from a marker selected from the group consisting of SEQ ID NO: 11 and SEQ ID NO: 12.

Embodiment 209

The method of Embodiment 204, wherein the marker molecule is within 1 centimorgans or less from a marker selected from the group consisting of SEQ ID NO: 11 and SEQ ID NO: 12.

Embodiment 210

The method of Embodiment 204, wherein the marker molecule is in a genomic region flanked by SEQ ID NOs: 11 and 12.

Embodiment 211

A method comprising:
a. obtaining a population of *Capsicum* plants,
b. genotyping the population using a marker molecule associated with a SHY1 QTL, where the marker molecule is within 10 centimorgans or less from a marker selected from the group consisting of SEQ ID NO: 13 and SEQ ID NO: 14,
c. selecting a *Capsicum* plant based on the genotyping, and
d. producing a progeny from the selected *Capsicum* plant.

Embodiment 212

The method of Embodiment 211, wherein the marker molecule is within 8 centimorgans or less from a marker selected from the group consisting of SEQ ID NO: 13 and SEQ ID NO: 14.

Embodiment 213

The method of Embodiment 211, wherein the marker molecule is within 5 centimorgans or less from a marker selected from the group consisting of SEQ ID NO: 13 and SEQ ID NO: 14.

Embodiment 214

The method of Embodiment 211, wherein the marker molecule is within 3 centimorgans or less from a marker selected from the group consisting of SEQ ID NO: 13 and SEQ ID NO: 14.

Embodiment 215

The method of Embodiment 211, wherein the marker molecule is within 2 centimorgans or less from a marker selected from the group consisting of SEQ ID NO: 13 and SEQ ID NO: 14.

Embodiment 216

The method of Embodiment 211, wherein the marker molecule is within 1 centimorgans or less from a marker selected from the group consisting of SEQ ID NO: 13 and SEQ ID NO: 14.

Embodiment 217

The method of Embodiment 211, wherein the marker molecule is in a genomic region flanked by SEQ ID NOs: 13 and 14.

Embodiment 218

A method comprising:
a. obtaining a population of Capsicum plants,
b. genotyping the population using a marker molecule associated with a SHY12 QTL, where the marker molecule is within 10 centimorgans or less from a marker selected from the group consisting of SEQ ID NO: 15 and SEQ ID NO: 16,
c. selecting a Capsicum plant based on the genotyping, and
d. producing a progeny from the selected Capsicum plant.

Embodiment 219

The method of Embodiment 218, wherein the marker molecule is within 8 centimorgans or less from a marker selected from the group consisting of SEQ ID NO: 15 and SEQ ID NO: 16.

Embodiment 220

The method of Embodiment 218, wherein the marker molecule is within 5 centimorgans or less from a marker selected from the group consisting of SEQ ID NO: 15 and SEQ ID NO: 16.

Embodiment 221

The method of Embodiment 218, wherein the marker molecule is within 3 centimorgans or less from a marker selected from the group consisting of SEQ ID NO: 15 and SEQ ID NO: 16.

Embodiment 222

The method of Embodiment 218, wherein the marker molecule is within 2 centimorgans or less from a marker selected from the group consisting of SEQ ID NO: 15 and SEQ ID NO: 16.

Embodiment 223

The method of Embodiment 218, wherein the marker molecule is within 1 centimorgans or less from a marker selected from the group consisting of SEQ ID NO: 15 and SEQ ID NO: 16.

Embodiment 224

The method of Embodiment 218, wherein the marker molecule is in a genomic region flanked by SEQ ID NOs: 15 and 16.

EXAMPLES

Example 1. Preparation of *C. annuum* Plants Producing Fruits with a *C. chinense* Specific Aroma Sweet bell peppers belong to *Capsicum annuum* (*C. annuum*). Some consumers assess bell peppers as bland and desire more aromas or flavors in sweet bell peppers. *Capsicum chinense* (*C. chinense*), on the other hand, comprises some extremely pungent peppers. *C. chinense* also comprises some desirable flavors, although traditionally *C. chinense* has only been used as donors for certain disease resistance traits. Not much has been explored to incorporate desirable flavors from *C. chinense* into other peppers, e.g., *C. annuum*. Here, a genetic introgression approach is used to breed *C. annuum* plants with *C. chinense* specific aromas or flavors.

In general, a *Capsicum* line is developed as follows: *C. annuum* with aroma profiles typical of *C. annuum* (recipient parent) are crossed to a *C. chinense* with unusual aroma (donor parent). The hybrid plants are either self-pollinated (to generate a segregating $F_2$) or are crossed again to a *C. annuum* with a typical aroma profile (to generate a segregating $BC_1F_1$ population or a segregating modified $BC_1F_1$ population). The segregating populations are grown and selected for fertility, lack of pungency, and presence of aroma from the donor parent. The individual plants in these segregating populations are then self-pollinated and the resulting families ($F_2$ or $BC_1F_2$ or modified $BC_1F_2$) are planted and again, individual plants are selected for self-pollination. This process is repeated several times until fixed lines are created.

For example, a *C. annuum* plant with an aroma profile typical of *C. annuum* (recipient parent or *C. annuum* parent, comprising an approximately 100% *C. annuum* genome) is crossed with a donor parent having a *C. chinense* specific aroma profile. The donor parent comprises approximately 75% *C. annuum* genome and approximately 25% *C. chinense* genome (e.g., line ZSP8T14-6274, deposited at ATCC under accession no. PTA-122300) which is derived from a mild orange *C. chinense* landrace. A landrace is a dynamic population of a cultivated plant that has historical origin, distinct identity and lacks formal crop improvement, as well as often being genetically diverse, locally adapted and associated with traditional farming systems. See Camacho Villa et al., *Plant Genetic Resources: Characterization and Utilization* 3(3):373-84 (2006). An exemplary *C. annuum* line used in the cross is SMO8T14-6275 which deposited at the ATCC under accession no. PTA-122298). From the cross, three separate hybrid plants are produced. They are hybrid SVPS2625, hybrid SVPS2646, and hybrid SVPS2626. They all comprise a *C. annuum* fruit type and aromas unique to *C. chinense*. Hybrid SVPS2625 is deposited at ATCC under accession no. PTA-122296.

Example 2. Origin and Breeding History of Parent Lines ZSP8T14-6274 and SMO8T14-6275

Hybrid SVPS2625 is an $F_1$ progeny of a cross between two inbreds SMO8T14-6275 and ZSP8T14-6274. Inbred ZSP8T14-6274 is the male parent and is developed using pedigree breeding from a three way cross. First, an $F_1$ hybrid is made between AP 2384 (a *Capsicum chinense* variety producing medium sized 2 cm×2 cm fruit that ripens from green to orange) and SMO-28-1284 (a green to orange mini blocky bell pepper). The $F_1$ hybrid is then crossed to 05LB LBGH 0550-M (a green to yellow mini blocky bell pepper that has a resistance gene conferring Tobamovirus (P0)) and single plant pedigree selection is initiated for a number of generations bringing the generation to $F_6$. The F6 seeds are bulked and subsequently named ZSP8T14-6274.

ZSP8T14-6274 develops a medium sized plant that produces small sized, yellow-orange mini fruit with deep interloculary grooves. The fruit matures from a medium green to yellow-orange. ZSP8T14-6274 contains a resistance gene conferring resistance to Tobamo virus (P0) and is easily crossed to *Capsicum annuum*. ZSP8T14-6274 has been observed as uniform and stable during the years 2010 through 2015, and any variation is within commercially acceptable limits.

Inbred SMO8T14-6275 is the female parent and is developed using the doubled haploid technique. Specifically, an $F_1$ hybrid is made between SMO-28-1234 and SBY-29-469 and is used as a donor for anthers for anther culture to grow haploid plants. The haploid plants are doubled to create homozygous diploid plants (doubled haploids, or DH), from which seeds are collected. Doubled haploids are planted in a trial and observed for horticultural characteristics. The DH variety is bulked, used in test crosses, and subsequently named SMO8T14-6275.

SMO8T14-6275 develops a medium sized anthocyanin-less plant that produces medium sized, midi-blocky, fruit. The fruit matures from a medium green to orange. The line contains the L2 resistance gene conferring resistance to Tobamo virus (P0,1). SMO8T14-6275 has been observed as uniform and stable during the years 2010 through 2015, and any variation is within commercially acceptable limits. SMO-28-1234 is a green to orange mini blocky bell pepper and contains the L2 resistance gene conferring resistance to Tobamo virus (P0, 1) and has purple anthers. SBY-29-469 is a green to yellow large deep blocky pepper and has anthocyaninless anthers.

Example 3. Determination of Aromatic Molecules Contributing to *C. chinense* Aromas Via Metabolic Profiling A comparative metabolic profiling approach is used to identify aromatic molecules underlying a *C. chinense* flavor profile. These aromatic molecules can also serve as metabolic fingerprints for identifying and tracking *C. chinense* aromas during pepper selection and breeding. Specifically, solid-phase microextraction (SPME) and gas chromatography mass spectrometry (GC-MS) are performed to analyze volatile metabolites from pepper fruits. The peppers analyzed include *C. annuum* peppers with an aroma profile typical of *C. annuum*, a *C. chinense* aroma donor plant, and a set of fixed progeny lines from Example 1 that comprise *C. annuum* horticultural traits and a *C. chinense* aroma profile. Volatile metabolites shared between pepper plants with a *C. chinense* flavor but absent from *C. annuum* are good candidate *C. chinense* aroma compounds.

To prepare samples for SPME and GC-MS analyses, leaf materials are first removed from pepper fruits which are then cut in half to remove seeds and rib materials. The remaining pepper materials (pericarp) are cut into small pieces and further shredded using a food chopper. The shredded peppers are mixed with an equal volume of water and homogenized in a blender to form a pepper puree. Twenty grams of the homogenized pepper puree are transferred into a 50 mL centrifuge tube, followed by adding 5 mL of a 200 mM EDTA-NaOH solution (pH 7.5) and 5 mL of a $CaCl_2$ solution (0.8 g/mL) to the tube. After mixing the solutions by inverting the tube for multiple times, 100 µL of a working deuterated internal standard solution (5 ppm, d3-Ethyl Acetate in methanol) is added into the mixture, followed by adding 100 µL of Methanol and further mixing by inverting the tube to form a processed pepper puree. Six grams of the processed pepper puree are transferred to a SPME headspace vial and subject to SPME volatile extraction on a Gerstel MPS Rail or similar autosampler with parameters shown in Table 1. After the SPME volatile extraction, a Thermo GC-MS is then used for the separation and detection of the volatile metabolites. The GC-MS uses a SPME injection liner coupled with a Merlin Microseal. The parameters used for GC-MS analysis are shown in Table 2.

Compound detection and relative response is performed using unique ions and retention times related to the compounds of interest. Signal extraction and compound identification is performed in XCalibur with the NIST database. Signal areas are integrated to determine system response. Data processing for calculation of relative response is performed in Microsoft Excel.

A relative response to a known concentration of deuterated-internal standard is used to avoid sampling variability. First, the retention time and unique ions for each compound of interest are used to extract the area under its curve. Curve area for the deuterated internal standard is also calculated using a retention time of 61.2 seconds and selected ions (46+91 m/z). The relative GC-MS response score of a compound is then determined using the following formula: Relative GC-MS Response Score of compound X=Area of Compound X/Area of Deuterated Internal Standard.

TABLE 1

Representative SPME parameters used for volatile extraction.

| Parameter | Value |
|---|---|
| SPME Fiber | 65 µm PDMS-DVB 23 gauge needle |
| Incubation Temp | 50° C. |
| Incubation Time | 4 min |
| Extraction Time | 10 min |
| Desorption Time | 60 sec. |

TABLE 2

Representative GC/MS Parameters for metabolic profiling of pepper aromatic molecules.

| Parameter | Value |
|---|---|
| Column | VF-5MS (20M × 0.15 mm ID × 0.15 µm df) |
| Injection Temperature | 220° C. |
| Injection Type | Splitless |
| Column Flow | 2.3 mL/min |
| Split Flow (ml/min) | 46 mL/min |
| Flow Control | Constant Flow |
| Oven Program | 60° C. (2 min) –> 10° C./min to 160° C. –> 20° C./min to 260° C. –> 260° C. (1 min) |
| Transfer Line | 250° C. |
| Mass Spectrometer Parameters | |
| Acquisition Range | 40-300 amu |
| Scan Rate | 500 amu/sec |
| Ion Source Temp | 200° C. |

Example 4. Identification of Three Terpenes as *C. chinense* Aroma Fingerprints

Through the comparative metabolic profiling approach described in Example 2, predominant volatiles are identified in line ZSP8T14-6274 but not found in *C. annuum* parent. These volatiles include three terpenes (α-Cubebene, δ-Cadinene, and 1,4-Cadinadiene). The same terpenes are also present in $F_1$ hybrid progenies of ZSP8T14-6274 and *C. annuum*.

To evaluate whether any of these volatiles correlate to unique aromas from *C. chinense*, the volatile profiles of a collection of 18 *C. annuum* genotypes are determined by SPME coupled with GC-MS. This more extensive survey reveals that the three terpenes (α-Cubebene, δ-Cadinene, and 1,4-Cadinadiene) appear unique to line ZSP8T14-6274 and its hybrid progenies. Therefore, these terpenes represent volatile fingerprints for *C. chinense* aromas and apparently are inheritable from line ZSP8T14-6274 into its hybrid progenies (Table 3). The same three terpenes are found in very low abundance in only one *C. annuum* (hybrid pepper PS09954859, published in U.S. Pat. No. 8,471,113, deposited at the American Type Culture Collection (ATCC) as accession No. PTA-11514), out of the 18 genotypes surveyed. PS09954859 is a *C. annuum* line with *C. chinense* in the pedigree from a disease resistance introgression cross. PS09954859 has two inbred parent lines SMR 99-1275 and SMY 99-1322, having ATCC Accession Nos. PTA-11520 and PTA-11517, respectively.

A trial from the year 2015 also confirms the identified three terpenes (α-Cubebene, δ-Cadinene, and 1,4-Cadinadiene) as volatile fingerprints of *C. chinense* aromas and their inheritability from line ZSP8T14-6274 into a hybrid progeny (Table 4).

Although the field conditions of the 2015 trial appears not optimal, the pepper plants are still substantially uniform and stable with some variations that are within commercially acceptable limits. As is true with most pepper breeding, a small percentage of variants can occur within commercially acceptable limits for almost any characteristic during the course of repeated multiplication of an inbred or its hybrid progeny.

To assess the best timing for sampling *C. chinense* signature aroma molecules, hybrid SVPS2625 pepper fruits are harvested at various maturation stages together with a control pepper line (Table 3a). These stages are characterized by the percentage of total fruit surface area exhibiting mature color (e.g., color change from green to red). For example, "75% color" stands for a pepper fruit having about 75% of total fruit surface area exhibiting mature color. In this test, peppers are harvested and immediately shipped on day 1 and received at the lab on day 2. Samples are prepared on day 2 and subject to GC-MS analysis on day 3. The observed amounts of signature volatiles (α-Cubebene, δ-Cadinene, and 1,4-Cadinadiene) are highest in fruits with between about 25% and 50% mature color, depending on plant condition. See Samples 1 and 2 in Table 3a. These volatiles are also detected in fruits with around 75% mature color and up to 100% mature color, albeit of lower levels. Therefore, to achieve the most reliable measurement of the identified three *C. chinense* signature aroma molecules (α-Cubebene, δ-Cadinene, and 1,4-Cadinadiene), fruits are preferably picked or harvested around 25%, around 50%, around 75%, between 25% and 50%, or between 50% and 75% color change and subject to flesh sample testing immediately or shortly thereafter (preferably within 3 days or 1 day of harvest). Fruit color continues to change to a higher percent mature color after harvest. Samples assayed outside of the desired time period may result in signature volatile levels lower than the detectable limit. See e.g., fruits in Example 6 below.

TABLE 3

Relative abundance of three terpene volatiles (α-Cubebene, δ-Cadinene, and 1,4-Cadinadiene) that are associated with *C. chinense* aromas (data from a 2014 trial).

| | Relative GC-MS Response Score | | | |
|---|---|---|---|---|
| Capsicum line | alpha-Cubebene | delta-Cadinene | 1,4-Cadinadiene | Plot location |
| Line ZSP8T14-6274 (male parent of SVPS2625) | 2.19 | 4.60 | 2.11 | Woodland |
| SMO8T14-6275 (female parent of SVPS2625) | 0.001 | 0.001 | 0.001 | Woodland |
| SVPS2625 | 0.32 | 0.34 | 0.19 | San Juan Bautista |
| Hybrid 2646 | 0.68 | 1.04 | 0.55 | San Juan Bautista |
| Hybrid 2626 | 3.4 | 4.62 | 3.06 | San Juan Bautista |
| Hybrid 2663 | 5.95 | 10.31 | 7.35 | San Juan Bautista |
| Hybrid 2661 | 13.48 | 22.05 | 16.39 | San Juan Bautista |
| PS09954859 | 0.19 | 0.20 | 0.09 | Woodland |
| PS09954859(resubmit) | 0.001 | 0.09 | 0.001 | Woodland |
| PS09954859 | 0.001 | 0.08 | 0.001 | San Juan Bautista |

TABLE 3a

Evaluation of *C. chinense* signature aroma molecules across fruit maturation stages.

| Variety | N | α-Cubebene (ratio to IS) | δ-Cadinene (ratio to IS) | 1,4-Cadinadiene (ratio to IS) |
|---|---|---|---|---|
| Control Green | 6 | ND | ND | ND |
| Control 75% Color | 8 | ND | ND | ND |
| Control 100% Color | 3 | ND | ND | ND |
| Sample-1 Green | 12 | 0.439 | 0.125 | 0.077 |
| Sample-1 25% Color | 11 | 0.446 | 0.160 | 0.087 |
| Sample-1 50% Color | 11 | 0.332 | 0.092 | 0.061 |
| Sample-1 75% Color | 13 | 0.207 | 0.062 | 0.037 |
| Sample-1 100% Color | 12 | 0.224 | 0.086 | 0.042 |
| Sample-2 Green | 15 | 0.043 | 0.024 | ND |
| Sample-2 25% Color | 13 | 0.056 | 0.018 | ND |
| Sample-2 50% Color | 15 | 0.217 | 0.070 | ND |
| Sample-2 75% Color | 13 | 0.124 | 0.039 | ND |
| Sample-2 100% Color | 20 | 0.056 | 0.030 | ND |

Samples 1 and 2 are hybrid SVPS2625 fruits harvested from two different plots where Sample 2 plants appear more stressed than Sample 1 plants.
Control is a hybrid pepper line related to hybrid PS09954859 described in Example 4.
ND stands for "not detected".
Average abundance of each volatile is shown for each harvest.
N refers to the number of pepper fruits sampled for each stage.

TABLE 4

Relative abundance of α-Cubebene, δ-Cadinene, and 1,4-Cadinadiene in a 2015 field trial (s.d. representing standard deviation).

| Capsicum line | Relative GC-MS Response Score | | | Total Sugars (%) | | Titratible Acidity (millimoles H+/100 g) | | Number of plots |
| --- | --- | --- | --- | --- | --- | --- | --- | --- |
| | alpha-Cubebene | delta-Cadinene | 1,4-Cadinadiene | Average | s.d. | Average | s.d. | |
| PS09954859 | 0.001 | 0.001 | 0.001 | 6.3 | n/a | 3.4 | n/a | 1 |
| SVPS2625 | 0.056 | 0.103 | 0.010 | 6.5 | 0.38 | 4.7 | 0.25 | 8 |
| Line ZSP8T14-6274 (male parent of SVPS2625) | 6.832 | 17.537 | 9.951 | 6.8 | 0.21 | 4.6 | 0.24 | 7 |
| SMO8T14-6275 (female parent of SVPS2625) | 0.001 | 0.001 | 0.001 | 6.4 | 0.24 | 5.0 | 0.17 | 8 |

Example 5. Development of Additional *C. annuum* Plants Having a *C. chinense* Aroma Via Genetic Introgression Additional *C. annuum* plants having a *C. chinense* aroma are produced by crossing a *C. annuum* parent plant with a donor parent having a *C. chinense* specific aroma profile. For example, the donor parent can be a *C. chinense* plant; line ZSP8T14-6274, deposited at ATCC under accession no. PTA-122300; or SVPS2625, deposited at ATCC under accession no. PTA-122296. The donor plant can also be any other *C. chinense* with high levels of one or more aroma molecules identified herein (e.g., α-Cubebene, δ-Cadinene, and 1,4-Cadinadiene). An $F_1$ hybrid plant from this cross is either self-pollinated (to generate a segregating $F_2$) or is crossed again to the *C. annuum* parent plant (to generate a segregating $BC_1F_1$ population or a segregating modified $BC_1F_1$ population). The segregating populations are grown and selected for fertility, lack of pungency, and presence of aroma from the donor parent. Volatile profiling can be performed as described in Example 2 to select progenies comprising signature volatile molecules that are associated with a *C. chinense* specific flavor (e.g., α-Cubebene, δ-Cadinene, and 1,4-Cadinadiene). Plants are also tested for their fruit sweetness (e.g., total sugar content) and sweet individuals are selected. Selected individual plants are then self-pollinated and the resulting families ($F_2$ or $BC_1F_2$ or modified $BC_1F_2$) are planted and individual plants are again selected for self-pollination. This process is repeated several times until fixed progeny lines are created which comprise essentially all the traits of *C. annuum* (e.g., sweet) and an aroma profile similar to the donor parent (e.g., a *C. chinense* specific flavor profile).

Example 6. Consumer Liking Test of Hybrid SVPS2625

Consumer preference is tested for hybrid SVPS2625 compared to PERO® brand mini-pointy yellow and PERO® brand mini-pointy orange peppers (PERO® Family Farms Food Company, LLC). For this example, none of the peppers tested have detectable *C. chinense* volatiles likely due to the harvesting time as described in Example 4 (FIG. 1). Commercially available peppers are purchased locally and hybrid SVPS2625 peppers are harvested at maturity and shipped overnight to the testing facility. The average total sugar content of the hybrid SVPS2625 pepper is 7.1% compared to 5.1% and 5.0% for the orange and yellow retail peppers, respectively (FIG. 1). The Brix rating for hybrid SVPS2625 is 10.3 which is significantly higher than the commercially available orange (9.0) and the commercially available yellow (8.8) (FIG. 1).

All peppers are prepared on the day of testing. Before testing, all abnormal peppers are removed. Test peppers are washed in 8° C. tap water for one minute. The peppers are then submerged in a wash solution containing 200 ppm CHLOROX® regular bleach for five minutes (Chlorox Co., Oakland, Calif.). The peppers are then washed again in fresh 8° C. tap water for one minute before air drying.

Figure 3:
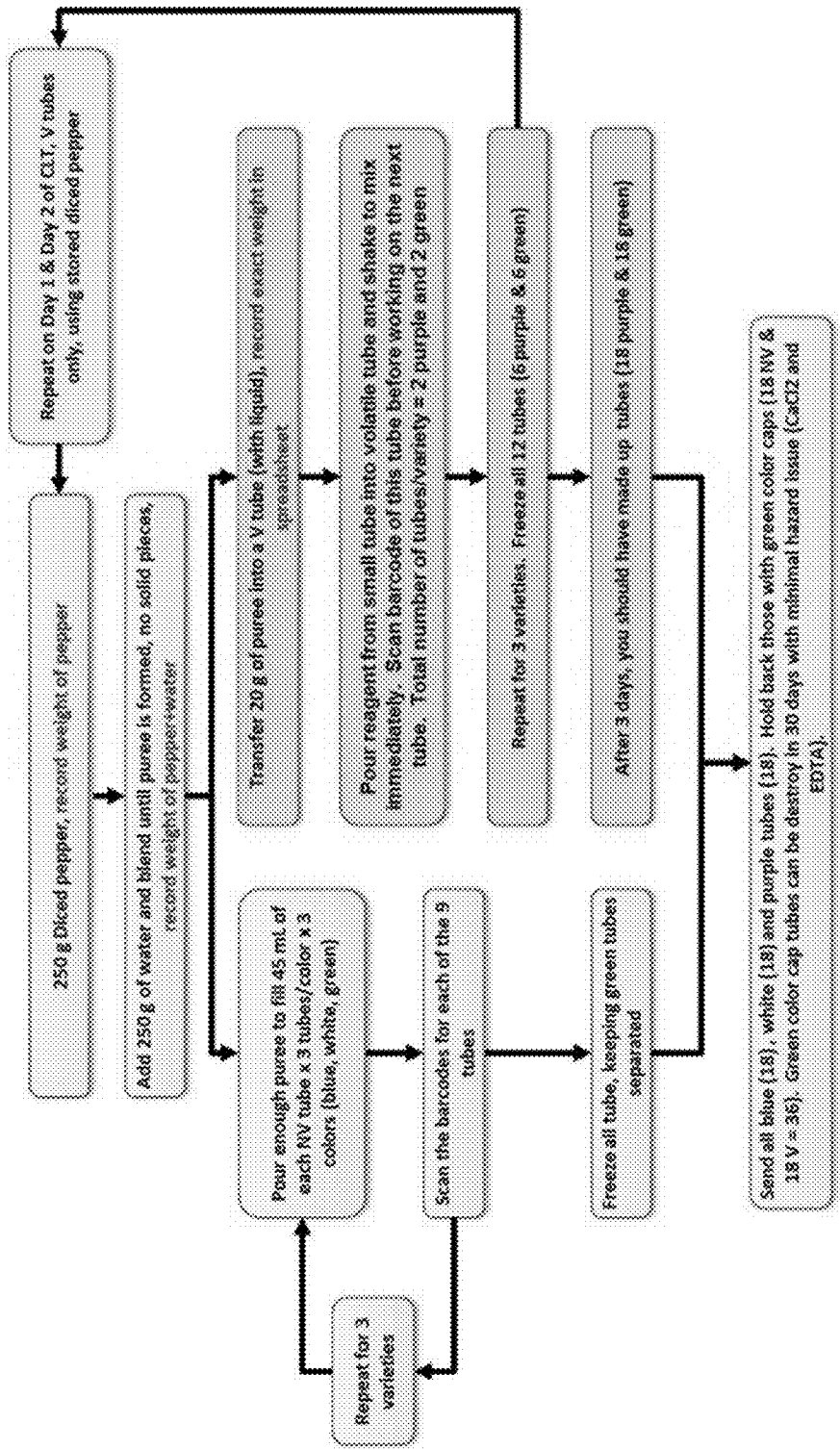
FIG. 3: Flow chart of the pepper non-volatile and volatile sampling process used in the consumer liking test.

Before sample preparation, peppers are sorted by color. The top and bottom 10% of each fruit is cut off. A pepper greater than 3.8 cm is cut in half from stem to peduncle and the seeds and placenta are removed using the pointed end of a knife. A pepper less than 3.8 cm in length is not cut and the seeds and placenta are removed using the pointed end of a knife. The peppers are diced using a NEMCO® easy chopper into 0.95 cm cubes (NEMCO® model 55500-2, Hicksville, Ohio). The diced peppers are mixed using a stainless steel spoon and separated for consumer testing and analytical sampling (FIG. 2). Pepper non-volatile and volatile sampling is performed for each group of peppers. 250 grams of diced peppers are blended with 250 grams of water and separated into sample tubes for testing; two replicates for both non-volatiles and volatiles for all three pepper preparations are collected (FIG. 3).

Consumer testing of 142 people is conducted in a supervised sensory lab setting. A paired preference format is used to make two comparisons: 1) hybrid SVPS2625 versus the commercially available mini-pointy yellow pepper and 2) hybrid SVPS2625 versus the commercially available mini-pointy orange peppers. Consumer testing is conducted under red light to reduce the impact of color differences on outcomes. For the test, consumers are asked to: identify which pepper is preferred (if there is no preference then pick a forced preference) and to identify the reason for a preference with a fill-in-the-blank questionnaire. Demographic, behavioral, and general taste preference questions are asked in follow up.

Figure 4:
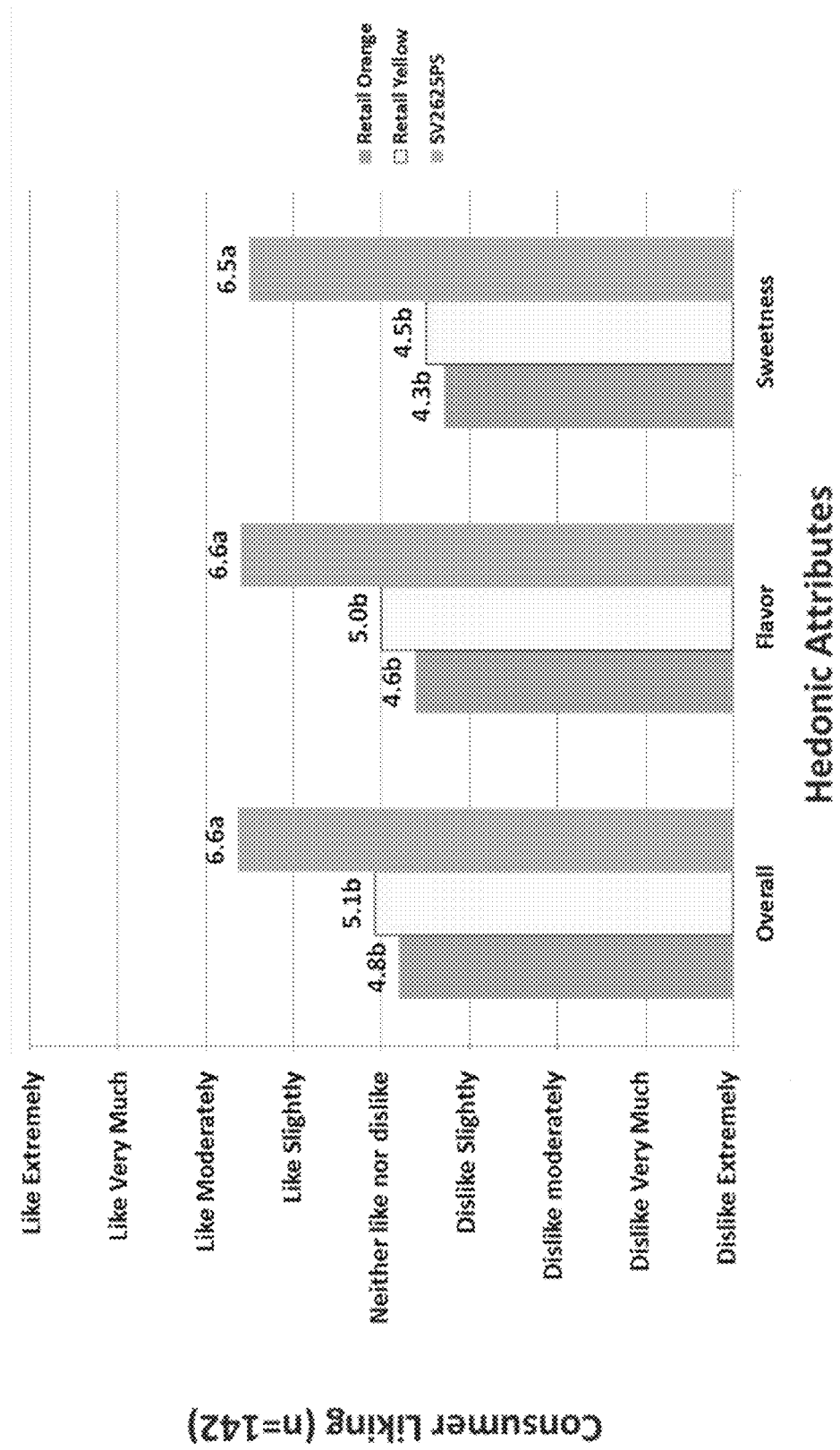
FIG. 4: Hedonic attributes as determined by consumers for the hybrid pepper SVPS2625, PERO® brand mini-pointy yellow, and PERO® brand mini-pointy orange peppers (PERO® Family Farms Food Company, LLC) during a sequential monadic liking test of 142 consumers. Consumers grade each of the attributes on a scale of 1 to 9. A score of 1 meaning "dislike extremely", a score of 2 meaning "dislike very much", a score of 3 meaning "dislike moderately", a score of 4 meaning "dislike slightly", a score of 5 meaning "neither like nor dislike", a score of 6 meaning "like slightly", a score of 7 meaning "like moderately", a score of 8 meaning "like very much", and a score of 9 meaning "like extremely".

Consumers prefer the taste of SVPS2625 (84%) over commercially available mini-pointy orange peppers (16%), citing reasons such as more sweet, more flavorful, and less bitter. Consumers prefer the taste of SVPS2625 (71%) over commercially available mini-pointy yellow peppers (29%), citing reasons such as more sweet, more flavorful, and less bitter. In a sequential monadic liking test, consumers are given all three samples and asked to rate each sample on a 9-point hedonic scale. The hedonic attribute scoring demonstrates that the hybrid SVPS2625 pepper is moderately liked overall, for flavor, and for sweetness. The commercially available orange and yellow peppers have significantly lower scores in all three categories (FIG. 4).

Example 7. Identification of Quantitative Trait Loci from the SMO-28-1234 Parental Line The SMO-28-1234 line is described in Example 2 as a progenitor to the hybrid pepper line SVPS2625. Use of this line is described below in the identification of genomic regions that control variation in total sugar because of its higher sugar, slightly higher acid, and better flavor rating compared to modern commercial bell peppers. Bi-parental $F_2:F_3$ and double haploid mapping populations are used for QTL identification. The SMO-28-1234 parental line is crossed to SBY-29-469 for linkage mapping. $F_2:F_3$ families are phenotyped in a randomized complete block design with four replicate plots of up to ten plants per $F_3$ family. Double haploid lines are generated from the $F_1$ plants of these crosses ($DH_1$ generation). $DH_1$ lines are sown in Felda, Fla. in a randomized complete block design with three replicate plots per $DH_1$ line for phenotypic data collection. A subset of each $DH_1$ line is sampled for genotyping and linkage mapping. Genotyping for $F_2:F_3$ and $DH_1$ lines is performed using over 130 markers from a pepper Taqman library to minimize gaps greater than 20 cM.

Phenotypic data is collected by pooling fruits from multiple plants per plot per sample. Fruits are assessed for total sugars (fructose+sucrose), fructose, glucose, titratable acidity (TA), and a second measure of titratable acidity (TA7) in a vegetable quality lab in Woodland, Calif. Plants at the Felda, Fla. location are also measured for perceived sweetness (sugartaste), acidity (acidtaste), and skin thickness (skin) by an individual tester on a 1-9 scale where 1 corresponds to the sweetest, highest acid, thinnest skin, and most favorable texture, respectively and 9 corresponds to the least sweet, lowest acid, thickest skin, and least pleasant texture. To describe the estimated properties of QTLs, tables are presented with data on the estimated QTL effect size (i.e. how much the QTL is expected to influence the trait), the proportion of total phenotypic variation in the population explained by a QTL, and its dominance estimate. The effect size is one half of the difference between the two contrasting homozygous QTL genotypes. The proportion of phenotypic variation describes how much of the variation present in the experiment is explained by a single QTL. Dominance is the phenotypic difference between the heterozygote QTL genotype and the average of the two homozygous QTL genotypes. Traits that are strongly influenced by the SMO2, SMO3, and SMO8 QTLs are shown in Tables 5, 9, and 12.

QTL identification is performed with the rqtl package implemented in the R platform and three QTL harboring intervals, SMO2, SMO3, and SMOG, are identified in the SMO-28-1234 parental line. To describe the genetic location of QTLs, the LOD profile is used to determine the statistical significance of a QTL result. The significance of a LOD score is determined from 1,000 permutations of the data. Because QTL peak estimates are not perfect, tables are provided with the confidence interval for each QTL. The confidence intervals are estimated using a 1.5 LOD interval calculated by moving down the LOD profile from the peak 1.5 'steps' (−1.5) and up from the peak 1.5 steps (+1.5) to identify the chromosome positions (Table 6, 7, 8, 10, 11, 13, and 14).

The SMO2 interval containing one or more QTLs influencing sugar content is discovered in a Woodland, Calif. field trial and subsequently identified in Culiacan, MX and Felda, Fla. field trials. The SMO2 interval is broad, ranging from 65 cM to 113 cM. In addition, a QTL for perceived sweetness flavor was also identified in Felda, Fla. within this interval. Consequently, there is strong support for a QTL influencing both sugar and the perceived flavor of sugar in the interval harboring SMO2. QTLs for sugars and acids are detected in Woodland, Calif. and Culiacan, MX (Table 5). QTLs for sugars and acid are found on chromosome 2 in the Felda, Fla. location (Table 5). The QTL confidence intervals for Woodland, Calif. (Table 6), Culiacan, MX (Table 7), and Felda, Fla. are shown (Table 8). The *Capsicum* line SMO8T14-6275 is tested and confirmed to comprise a homozygous SMO2 QTL. The hybrid *Capsicum* line SVPS2625 is the progeny of SMO8T14-6275 and is heterozygous at the SMO2 QTL.

TABLE 5

SMO2 phenotype parameter estimates from SBY-29-469/SMO-28-1234 $F_2:F_3$ and $DH_1$ populations

| Name | Trait | Chr | Position in cM | % of variance | Size of Effect |
|---|---|---|---|---|---|
| Woodland, CA; Summer 2010 | | | | | |
| SMO2-sugar | Sugar | 2 | 77.2 | 26.7 | −0.41 |
| SMO2-sugar | Fructose | 2 | 74.2 | 22.6 | −0.19 |
| SMO2-sugar | Glucose | 2 | 98.2 | 27.8 | −0.19 |
| SMO2-acid | TA | 2 | 98.2 | 26.6 | −0.28 |
| SMO2-acid | TA7 | 2 | 102.2 | 27.1 | −0.26 |
| Culiacan, MX; Winter 2010 | | | | | |
| SMO2-sugar | Sugar | 2 | 100.2 | 23 | −0.49 |
| SMO2-sugar | Fructose | 2 | 100.2 | 13.5 | −0.2 |
| SMO2-sugar | Glucose | 2 | 100.2 | 32.2 | −0.3 |
| SMO2-acid | TA | 2 | 76.2 | 13.7 | −0.27 |
| SMO2-acid | TA7 | 2 | 100.2 | 22.6 | −0.23 |
| Felda, FL; Winter 2011 | | | | | |
| SMO2-sugar | Sugar | 2 | 109 | 14.4 | −0.28 |
| SMO2-sugar | Glucose | 2 | 108 | 21.6 | −0.18 |
| SMO2-acid | TA7 | 2 | 111.7 | 17.1 | −0.17 |
| SMO2-sugar | SugarTaste | 2 | 100 | 20.6 | 0.62 |
| SMO2-acid | AcidTaste | 2 | 99 | 18.2 | 0.57 |
| SMO2-thickness | Skin | 2 | 55 | 21.2 | 0.64 |

TABLE 6

SMO2 1.5 LOD QTL confidence interval Woodland, CA, summer 2010

| LOD | chr | pos | Sugar | chr | pos | Fructose | chr | pos | Glucose |
|---|---|---|---|---|---|---|---|---|---|
| −1.5 | 2 | 67.17 | 10.61 | 2 | 63.17 | 8.82 | 2 | 70.17 | 11.60 |
| peak | 2 | 77.17 | 12.31 | 2 | 74.17 | 10.40 | 2 | 98.17 | 13.18 |
| +1.5 | 2 | 100.17 | 10.80 | 2 | 98.17 | 8.76 | 2 | 105.17 | 11.34 |

| LOD | chr | pos | TA | chr | pos | TA7 |
|---|---|---|---|---|---|---|
| −1.5 | 2 | 76.17 | 10.81 | 2 | 95.17 | 11.99 |
| peak | 2 | 98.17 | 12.33 | 2 | 102.17 | 13.92 |
| +1.5 | 2 | 103.58 | 10.67 | 2 | 107.17 | 12.28 |

TABLE 7

SMO2 1.5 LOD QTL confidence interval Culiacan, MX, winter 2010

| LOD | chr | pos | Sugar | chr | pos | Fructose | chr | pos | Glucose |
|---|---|---|---|---|---|---|---|---|---|
| −1.5 | 2 | 95.17 | 6.43 | 2 | 95.17 | 3.34 | 2 | 96.17 | 11.31 |
| peak | 2 | 100.17 | 8.92 | 2 | 100.17 | 4.99 | 2 | 100.17 | 13.17 |
| +1.5 | 2 | 110.17 | 7.41 | 2 | 113.17 | 3.12 | 2 | 107.17 | 11.66 |

TABLE 7-continued

SMO2 1.5 LOD QTL confidence interval Culiacan, MX, winter 2010

| LOD | chr | pos | TA | chr | pos | TA7 |
|---|---|---|---|---|---|---|
| −1.5 | 2 | 50.17 | 3.64 | 2 | 70.17 | 6.87 |
| peak | 2 | 76.17 | 5.22 | 2 | 99.17 | 8.56 |
| +1.5 | 2 | 104.17 | 3.71 | 2 | 106.17 | 6.99 |

TABLE 8

SMO2 1.5 LOD QTL confidence interval Felda, FL, winter 2010

| LOD | chr | pos | Sugar | chr | pos | Glucose | chr | pos | Sugar-Taste |
|---|---|---|---|---|---|---|---|---|---|
| −1.5 | 2 | 72.03 | 1.16 | 2 | 72.03 | 2.37 | 2 | 26.03 | 1.67 |
| peak | 2 | 109.03 | 2.71 | 2 | 108.03 | 3.94 | 2 | 100.03 | 3.18 |
| +1.5 | 2 | 113.62 | 2.45 | 2 | 113.62 | 3.45 | 2 | 113.62 | 1.80 |

| LOD | chr | pos | Acid-Taste | chr | pos | Skin |
|---|---|---|---|---|---|---|
| −1.5 | 2 | 26.03 | 0.25 | 2 | 43.03 | 1.71 |
| peak | 2 | 100.03 | 3.10 | 2 | 55.03 | 3.43 |
| +1.5 | 2 | 113.62 | 1.10 | 2 | 86.03 | 1.92 |

The SMO3 interval is identified as a large but variable QTL on chromosome 3 influencing variation in sugars and acids in plants grown in Woodland, Calif. and acids in Culiacan, MX (Table 9). The QTL is detected in Woodland, Calif. and in Culiacan, MX field plots at a relaxed significance threshold. The SMO3 interval spans 143 to 184 cM on chromosome 3. The QTL confidence intervals are shown for Woodland, Calif. (Table 10) and Culiacan, MX (Table 11). The *Capsicum* line SMO8T14-6275 is tested and confirmed to comprise a homozygous SMO3 QTL. The hybrid *Capsicum* line SVPS2625 is the progeny of SMO8T14-6275 and is heterozygous at the SMO3 QTL.

TABLE 9

SMO3 phenotype parameter estimates from SBY-29-469/SMO-28-1234 F$_2$:F$_3$ populations

| Name | Trait | Chr | Position in cM | % of variance | Size of Effect |
|---|---|---|---|---|---|
| Woodland, CA; summer 2010 | | | | | |
| SMO3-sugar | Sugar | 3 | 159.9 | 10.8 | −0.22 |
| SMO3-sugar | Fructose | 3 | 155.9 | 14.2 | −0.12 |
| SMO3-sugar | Glucose | 3 | 159.9 | 8.6 | −0.098 |
| SMO3-acid | TA | 3 | 161.9 | 20.5 | −0.25 |
| SMO3-acid | TA7 | 3 | 161.9 | 21.2 | −0.23 |
| Culiacan, MX; Winter 2010 | | | | | |
| SMO3-acid | TA | 3 | 184.4 | 14.7 | −0.22 |

TABLE 10

SMO3 1.5 LOD QTL confidence interval Woodland, CA, summer 2010

| LOD | chr | pos | Sugar | chr | pos | Fructose | chr | pos | Glucose |
|---|---|---|---|---|---|---|---|---|---|
| −1.5 | 3 | 143.88 | 2.94 | 3 | 147.88 | 4.43 | 3 | 141.88 | 2.06 |
| peak | 3 | 156.88 | 4.49 | 3 | 155.88 | 6.09 | 3 | 160.88 | 3.62 |
| +1.5 | 3 | 177.88 | 2.82 | 3 | 174.88 | 4.42 | 3 | 180.88 | 1.93 |

TABLE 10-continued

SMO3 1.5 LOD QTL confidence interval Woodland, CA, summer 2010

| LOD | chr | pos | TA | chr | pos | TA7 |
|---|---|---|---|---|---|---|
| −1.5 | 3 | 152.88 | 7.71 | 3 | 151.88 | 8.02 |
| peak | 3 | 161.88 | 9.33 | 3 | 161.88 | 9.82 |
| +1.5 | 3 | 172.46 | 7.64 | 3 | 170.88 | 8.09 |

TABLE 11

SMO3 1.5 LOD QTL confidence interval Culiacan, MX, winter 2010

| LOD | chr | pos | Sugar | chr | pos | Glucose |
|---|---|---|---|---|---|---|
| −1.5 | 3 | 176.88 | 3.40 | 3 | 154.88 | 11.00 |
| peak | 3 | 184.44 | 5.02 | 3 | 159.94 | 12.84 |
| +1.5 | 3 | 184.44 | 5.02 | 3 | 164.88 | 11.06 |

The SMO8 interval contains a QTL on chromosome 8 influencing variation in sugars and acids and is detected in Woodland, Calif. and Felda, Fla. (Table 12). The SMO8 interval spans 37 to 63 cM on chromosome 8. The QTL confidence intervals are shown for Woodland, Calif. (Table 13) and Felda, Fla. (Table 14).

TABLE 12

SMO8 phenotype parameter estimates from SBY-29-469/SMO-28-1234 F$_2$:F$_3$ and DH$_1$ populations

| Name | Trait | Chr | Position in cM | % of variance | Size of Effect |
|---|---|---|---|---|---|
| Woodland, CA; Summer 2010 | | | | | |
| SMO8-sugar | Sugar | 8 | 59.4 | 10.5 | −0.21 |
| SMO8-sugar | Fructose | 8 | 59.4 | 9 | −0.09 |
| SMO8-sugar | Glucose | 8 | 58.7 | 11 | −0.11 |
| SMO8-acid | TA | 8 | 56.7 | 17 | −0.25 |
| SMO8-acid | TA7 | 8 | 59.4 | 10.7 | −0.17 |
| Felda, FL; Winter 2010 | | | | | |
| SMO8-sugar | Fructose | 8 | 45.7 | 26.8 | −0.21 |
| SMO8-acid | TA | 8 | 54.7 | 33.8 | −0.37 |

TABLE 13

SMO8 1.5 LOD QTL confidence interval Woodland, CA, summer 2010

| LOD | chr | pos | Sugar | chr | pos | Fructose | chr | pos | Glucose |
|---|---|---|---|---|---|---|---|---|---|
| −1.5 | 8 | 50.73 | 2.95 | 8 | 50.73 | 2.10 | 8 | 49.73 | 3.36 |
| peak | 8 | 59.37 | 4.61 | 8 | 59.37 | 3.85 | 8 | 58.73 | 4.91 |
| +1.5 | 8 | 64.73 | 3.00 | 8 | 67.23 | 2.29 | 8 | 64.73 | 2.93 |

| LOD | chr | pos | TA | chr | pos | TA7 |
|---|---|---|---|---|---|---|
| −1.5 | 8 | 50.73 | 6.10 | 8 | 49.73 | 2.85 |
| peak | 8 | 57.73 | 7.63 | 8 | 59.37 | 4.55 |
| +1.5 | 8 | 62.73 | 5.36 | 8 | 63.73 | 2.93 |

TABLE 14

SMO8 1.5 LOD QTL confidence interval Felda, FL, winter 2010

| LOD | chr | pos | TA | chr | pos | Fructose |
|---|---|---|---|---|---|---|
| −1.5 | 8 | 42.73 | 5.03 | 8 | 37.73 | 3.18 |
| peak | 8 | 54.73 | 6.76 | 8 | 45.73 | 4.73 |
| +1.5 | 8 | 61.73 | 5.11 | 8 | 62.73 | 3.03 |

Example 8. Identification of Additional Flavor and Taste Quantitative Trait Loci To identify genomic regions that control variation in total sugar the SZZ-8T10901 line is chosen for its higher sugar, slightly higher acid, and better flavor rating compared to modern commercial bell peppers. Bi-parental $F_2$:$F_3$ and double haploid mapping populations are used for QTL identification. The SZZ-8T10901 parental line is crossed to SBY-29-469 for linkage mapping. $F_2$:$F_3$ families are phenotyped in a randomized complete block design with four replicate plots of up to ten plants per $F_3$ family. Double haploid lines are generated from the $F_1$ plants of these crosses ($DH_1$ generation). $DH_1$ lines are sown in Felda, Fla. in a randomized complete block design with three replicate plots per $DH_1$ line for phenotypic data collection. A subset of each $DH_1$ line is sampled for genotyping and linkage mapping. Genotyping is performed using over 130 markers from a pepper Taqman library to minimize gaps greater than 20 cM.

Phenotypic data is collected by pooling fruits from multiple plants per plot per sample. Fruits are assessed for total sugars (fructose+sucrose), fructose, glucose, titratable acidity (TA), and a second measure of titratable acidity (TA7) in a vegetable quality lab in Woodland, Calif. Plants at the Felda, Fla. location are also measured for perceived sweetness (sugartaste) and skin thickness (skin) by an individual tester on a 1-9 scale where 1 corresponds to the sweetest, highest acid, thinnest skin, and most favorable texture, respectively and 9 corresponds to the least sweet, lowest acid, thickest skin, and least pleasant texture. To describe the estimated properties of QTLs, tables are presented with data on the estimated QTL effect size (i.e. how much the QTL is expected to influence the trait), the proportion of total phenotypic variation in the population explained by a QTL, and its dominance estimate. The effect size is one half of the difference between the two contrasting homozygous QTL genotypes. The proportion of phenotypic variation describes how much of the variation present in the experiment is explained by a single QTL. Dominance is the phenotypic difference between the heterozygote QTL genotype and the average of the two homozygous QTL genotypes. Traits that are strongly influenced by the SZZ3, SZZ4, and SZZ11 QTLs are shown in Tables 15, 18, and 20.

QTL identification is performed with the rqtl package implemented in the R platform and three QTL harboring intervals, SZZ3, SZZ4, and SZZ11, are identified in the SZZ-8T10901 parental line. To describe the genetic location of QTLs, the LOD profile is used to determine the statistical significance of a QTL result. The significance of a LOD score is determined from 1,000 permutations of the data. Because QTL peak estimates are not perfect, tables are provided with the confidence interval for each QTL. The confidence intervals are estimated using a 1.5 LOD interval calculated by moving down the LOD profile from the peak 1.5 'steps' (−1.5) and up from the peak 1.5 steps (+1.5) to identify the chromosome positions (Table 16, 17, 19, 21, 22, and 23).

The SZZ3 interval contains one to two QTLs influencing sugars on chromosome 3 and is detected at the Felda, Fla. and Almeria, ES locations (Table 15). The perceived sweetness (sugartaste) data from Felda, Fla. also implicates the SZZ3 interval (Table 15). There is a first potential QTL delimited by a confidence interval spanning 63-115 cM that is detected in Felda, Fla. (Table 17). A second potential QTL is within the interval of 158-186 cM, which is a more significant QTL at the Almeria, ES location (Table 16). Both the Felda, Fla. and Almeria, ES sites show two distinct peaks in the LOD profile on chromosome 3, although in Felda, Fla. the second peak in the 158-186 cM region is not significant. The perceived sweetness data from Felda, Fla. also exhibits a QTL that overlaps with the 63-115 cM QTL (Table 17). For these reasons, the sugar QTL in the 63-118 cM interval is designated SZZ3 due to its repeated observations in two locations and co-location with a perceived sweetness QTL (Table 16 and 17).

TABLE 15

SZZ3 phenotype parameter estimates from SBY-29-469/SZZ-8T10901 $F_2$:$F_3$ and $DH_1$ populations

| Name | Trait | Chr | Position in cM | % of variance | Size of Effect |
|---|---|---|---|---|---|
| Almeria, ES | | | | | |
| SZZ3-sugar | Sugar | 3 | 156.4 | 15 | −0.24 |
| SZZ3-sugar | Fructose | 3 | 156.4 | 15.3 | −0.15 |
| SZZ3-sugar | Glucose | 3 | 107.4 | 13.3 | −0.11 |
| SZZ3-acid | TA | 3 | 185.4 | 14.4 | −0.19 |
| SZZ3-acid | TA7 | 3 | 185.4 | 12.4 | −0.14 |
| Felda, Fl; winter 2010 | | | | | |
| SZZ3-sugar | Sugar | 3 | 82.2 | 17.5 | −0.35 |
| SZZ3-sugar | Fructose | 3 | 82.2 | 18.3 | −0.21 |
| SZZ3-sugar | SugarTaste | 3 | 27.7 | 26.8 | 0.66 |

TABLE 16

SZZ3 1.5 LOD QTL confidence interval Almeria, ES, winter 2010

| LOD | chr | pos | Sugar | chr | pos | Fructose | chr | pos | Glucose |
|---|---|---|---|---|---|---|---|---|---|
| −1.5 | 3 | 99.43 | 3.80 | 3 | 146.43 | 4.46 | 3 | 85.43 | 3.20 |
| peak | 3 | 156.43 | 5.35 | 3 | 156.43 | 5.97 | 3 | 107.43 | 4.81 |
| +1.5 | 3 | 167.43 | 3.84 | 3 | 166.43 | 4.30 | 3 | 185.91 | 3.22 |

| LOD | chr | pos | TA | chr | pos | TA7 |
|---|---|---|---|---|---|---|
| −1.5 | 3 | 158.43 | 3.36 | 3 | 162.43 | 2.71 |
| peak | 3 | 185.43 | 4.97 | 3 | 185.43 | 4.25 |
| +1.5 | 3 | 185.91 | 4.89 | 3 | 185.91 | 4.17 |

TABLE 17

SZZ3 1.5 LOD QTL confidence interval Felda, FL, winter 2010

| LOD | chr | pos | Sugar | chr | pos | Fructose | chr | pos | SugarTaste |
|---|---|---|---|---|---|---|---|---|---|
| −1.5 | 3 | 63.90 | 1.48 | 3 | 64.71 | 1.59 | 3 | 15.71 | 3.30 |
| peak | 3 | 82.21 | 2.99 | 3 | 82.21 | 3.13 | 3 | 27.71 | 5.02 |
| +1.5 | 3 | 115.71 | 1.41 | 3 | 115.71 | 1.56 | 3 | 79.71 | 3.49 |

The SZZ4 interval contains a QTL on chromosome 4 influencing sugars and is detected in Woodland, Calif. but there was no evidence for a QTL at this position in the Almeria, ES trial (Table 18). However, the SZZ4 interval for fructose had a p value of 0.09 in the Felda trial, and because the Woodland trial used a relatively stringent false discovery rate of 5%, the FDR rate was relaxed to 10% at which point the fructose LOD peak for SZZ4 becomes significant for the Felda, Fla. population. SZZ4 is detected within the interval of 84-107 cM on chromosome 4. The QTL confidence interval is shown for Woodland, Calif. (Table 19).

TABLE 18

SZZ4 phenotype parameter estimates from SBY-29-469/
SZZ-8T10901 $F_2$:$F_3$ and $DH_1$ populations
Woodland, CA; Summer 2010

| Name | Trait | Chr | Position in cM | % of variance | Size of Effect |
|---|---|---|---|---|---|
| SZZ4-sugar | Sugar | 4 | 95 | 15.7 | −0.28 |
| SZZ4-sugar | Fructose | 4 | 95.1 | 17.1 | −0.16 |

TABLE 19

SZZ4 1.5 LOD QTL confidence interval Woodland, CA, summer 2010

| LOD | chr | pos | Sugar | chr | pos | Fructose |
|---|---|---|---|---|---|---|
| −1.5 | 4 | 84.05 | 3.83 | 4 | 84.05 | 4.66 |
| peak | 4 | 95.05 | 5.51 | 4 | 95.05 | 6.35 |
| +1.5 | 4 | 107.05 | 3.92 | 4 | 108.05 | 4.64 |

The SZZ11 interval on chromosome 11 influences sugars and acids at Woodland, Calif. and Almeria, ES and acids and skin thickness at Felda, Fla. (Table 20). The consistent acid QTL detected in all three locations within the interval of 50-73 cM on chromosome 11. The QTL confidence intervals are shown for Woodland, Calif. (Table 21), Almeria, ES (Table 22), and Felda, Fla. (Table 23).

TABLE 20

SZZ11 phenotype parameter estimates from SBY-
29-469/SZZ-8T10901 $F_2$:$F_3$ and $DH_1$ populations

| Name | Trait | Chr | Position in cM | % of variance | Size of Effect |
|---|---|---|---|---|---|
| Woodland, CA; Summer 2010 | | | | | |
| SZZ11-sugar | Sugar | 11 | 59.3 | 13.8 | −0.23 |
| SZZ11-sugar | Fructose | 11 | 57.9 | 15.3 | −0.12 |
| SZZ11-acid | TA | 11 | 57.9 | 43.6 | −0.26 |
| SZZ11-acid | TA7 | 11 | 59.3 | 28 | −0.16 |
| Almeria, ES; Winter 2010 | | | | | |
| SZZ11-sugar | Fructose | 11 | 38.9 | 10.9 | −0.11 |
| SZZ11-acid | TA | 11 | 60.9 | 13.1 | −0.2 |
| SZZ11-acid | TA7 | 11 | 59.9 | 13.8 | −0.16 |
| Felda, FL; Winter 2010 | | | | | |
| SZZ11-acid | TA | 11 | 66.9 | 38.4 | −0.43 |
| SZZ11-acid | TA7 | 11 | 65.9 | 39 | −0.34 |
| SZZ11-thickness | Skin | 11 | 50.6 | 20.3 | −0.68 |

TABLE 21

SZZ11 1.5 LOD QTL confidence interval Woodland, CA, summer 2010

| LOD | chr | pos | Sugar | chr | pos | Fructose | chr | pos | TA |
|---|---|---|---|---|---|---|---|---|---|
| −1.5 | 11 | 39.91 | 3.16 | 11 | 38.91 | 3.79 | 11 | 51.91 | 16.79 |
| peak | 11 | 59.91 | 4.75 | 11 | 57.91 | 5.40 | 11 | 57.91 | 18.37 |
| +1.5 | 11 | 80.91 | 3.20 | 11 | 71.91 | 3.87 | 11 | 65.91 | 16.54 |

| LOD | chr | pos | TA7 |
|---|---|---|---|
| −1.5 | 11 | 54.24 | 8.36 |
| peak | 11 | 59.31 | 10.41 |
| +1.5 | 11 | 66.91 | 8.87 |

TABLE 22

SZZ11 1.5 LOD QTL confidence interval Almeria, ES, winter 2010

| LOD | chr | pos | TA | chr | pos | TA7 |
|---|---|---|---|---|---|---|
| −1.5 | 11 | 35.91 | 2.62 | 11 | 35.91 | 2.99 |
| peak | 11 | 60.91 | 4.29 | 11 | 59.91 | 4.59 |
| +1.5 | 11 | 70.91 | 2.65 | 11 | 70.91 | 3.00 |

TABLE 23

SZZ11 1.5 LOD QTL confidence interval Felda, FL, winter 2010

| LOD | chr | pos | TA | chr | pos | TA7 | chr | pos | Skin |
|---|---|---|---|---|---|---|---|---|---|
| −1.5 | 11 | 50.91 | 6.07 | 11 | 50.91 | 6.12 | 11 | 42.91 | 1.94 |
| peak | 11 | 66.91 | 7.66 | 11 | 65.91 | 7.69 | 11 | 50.61 | 3.53 |
| +1.5 | 11 | 73.41 | 5.98 | 11 | 73.41 | 5.94 | 11 | 70.91 | 1.89 |

Example 9. Identification of Further Additional Flavor and Taste Quantitative Trait Loci To identify genomic regions that control variation in total acids and aroma the SHY2761 line is chosen for its acidity and aroma compared to modern commercial bell peppers. Bi-parental $F_2$:$F_3$ and double haploid mapping populations are used for QTL identification. The SHY2761 parental line is crossed to SIT-27-500 for linkage mapping. Double haploid lines are generated from the $F_1$ plants of these crosses ($DH_1$ generation). $DH_1$ lines are sown in Felda, Fla. in a randomized complete block design with three replicate plots per $DH_1$ line for phenotypic data collection. A subset of each $DH_1$ line is sampled for genotyping and linkage mapping. Genotyping for $DH_1$ lines is performed using over 130 markers from a pepper Taqman library to minimize gaps greater than 20 cM.

Phenotypic data is collected by pooling fruits from multiple plants per plot per sample. Fruits are assessed for total sugars (fructose+sucrose), fructose, glucose, titratable acidity (TA), and a second measure of titratable acidity (TA7) in a vegetable quality lab in Woodland, Calif. (Table 24). Plants at the Felda, Fla. location are also measured for perceived sweetness (sugartaste), acidity (acidtaste), and skin thickness (skin) by an individual tester on a 1-9 scale where 1 corresponds to the sweetest, highest acid, thinnest skin, and most favorable texture, respectively and 9 corresponds to the least sweet, lowest acid, thickest skin, and least pleasant texture (Table 24). To describe the estimated properties of QTLs, tables are presented with data on the estimated QTL effect size (i.e. how much the QTL is expected to influence the trait) and the proportion of total phenotypic variation in the population explained by a QTL. The effect size is one half of the difference between the two contrasting homozygous QTL genotypes. The proportion of phenotypic variation describes how much of the variation present in the experiment is explained by a single QTL.

The SHY1 interval is identified from the SHY2761 parental line with the rqt1 package implemented in the R platform. To describe the genetic location of QTLs, the LOD profile is used to determine the statistical significance of a QTL result. The significance of a LOD score is determined from 1,000 permutations of the data. Because QTL peak estimates are not perfect, tables are provided with the confidence interval for each QTL. The confidence intervals are estimated using a 1.5 LOD interval calculated by moving down the LOD profile from the peak 1.5 'steps' (−1.5) and up from the peak 1.5 steps (+1.5) to identify the chromosome positions (Table 25).

One to two QTLs affecting aroma and longipinene were identified on chromosome 1 in Felda, Fla. field trials (Table 24). The region separating these QTLs has no genetic markers. Therefore, it is not clear if these two peaks are a consequence of this marker-gap or represent two true QTLs. The SHY1 aroma QTL is detected within the interval of 38-130 cM on chromosome 1. The chromosome 1 QTL confidence interval for the Felda, Fla. population is shown in Table 25. Within this same population, composite interval mapping detected a QTL for aroma and longipinene on chromosome 12 from 95-106 cM (longipinene) and 97-106 cM (aroma) that was not detected by interval mapping.

TABLE 24

SHY1 phenotype parameter estimates from SIT-27-500/SHY-27-61 $DH_1$ population Felda, FL; Winter 2010

| Name | Trait | Chr | Position in cM | % of variance | Size of Effect |
|---|---|---|---|---|---|
| SHY1-sugar | Fructose | 1 | 44.8 | 19.9 | −0.19 |
| SHY1-thickness | Skin | 1 | 72.8 | 39.6 | −1.1 |
| SHY1-aroma | Aroma | 1 | 113.6 | 25 | 0.82 |
| SHY1-aroma | Longipinene | 1 | 56.4 | 21.8 | −10496 |

TABLE 25

SHY1 1.5 LOD QTL confidence interval Felda, FL, winter 2010

| LOD | chr | pos | Fructose | chr | pos | Skin | chr | pos | Aroma |
|---|---|---|---|---|---|---|---|---|---|
| −1.5 | 1 | 28.78 | 1.85 | 1 | 45.78 | 5.20 | 1 | 38.78 | 1.74 |
| peak | 1 | 44.78 | 3.43 | 1 | 72.78 | 6.73 | 1 | 113.62 | 3.80 |
| +1.5 | 1 | 115.78 | 1.92 | 1 | 91.78 | 5.22 | 1 | 129.78 | 1.80 |

| LOD | chr | pos | Longi-pinene |
|---|---|---|---|
| −1.5 | 1 | 29.78 | 1.15 |
| peak | 1 | 56.37 | 3.23 |
| +1.5 | 1 | 130.78 | 1.15 |

Example 10. Development of Additional C. annuum Plants Having Increased Sugars and Acids Via Genetic Introgression Additional C. annuum plants having increased sugars and acids are produced by crossing a C. annuum parent plant with a donor having one or more QTLs for increased sugars, acids, or both (Table 26). For Example, the donor parent can be SMO-28-1234, SZZ-8T10901, SHY27-61, a progeny thereof, or any other plant with high levels of sugars or acids. An $F_1$ hybrid plant from this cross is either self-pollinated (to generate a segregating $F_2$) or is crossed again to the C. annuum parent plant (to generate a segregating $BC_1F_1$ population or a segregating modified $BC_1F_1$ population). The segregating populations are grown and selected for fertility and checked for the desired traits from the donor parent. Plants are tested for their fruit sweetness (e.g., total sugar content) and sweet individuals are selected. Selected individual plants are then self-pollinated and the resulting families ($F_2$ or $BC_1F_2$ or modified $BC_1F_2$) are planted and individual plants are again selected for self-pollination. This process is repeated several times until fixed progeny lines are created which comprise essentially all the desired traits of C. annuum parents (e.g., sweetness or acidity).

TABLE 26

Summary of Sugar, Acid, and Aroma QTLs presented

| QTL | Chromosome | Interval | Underlying Trait | Flanking Marker SEQ ID NO |
|---|---|---|---|---|
| SMO2 | 2 | 65-113 cM | total sugar content | SEQ ID NO: 1-2 |
| SMO3 | 3 | 143-184 cM | total sugar content | SEQ ID NO: 3-4 |
| SMO8 | 8 | 37-63 cM | total sugar content | SEQ ID NO: 5-6 |
| SZZ3 | 3 | 63-118 cM | total sugar content | SEQ ID NO: 7-8 |
| SZZ4 | 4 | 84-107 cM | total sugar content | SEQ ID NO: 9-10 |
| SZZ11 | 11 | 50-73 cM | total acidity content | SEQ ID NO: 11-12 |
| SHY1 | 1 | 38-130 cM | total aroma | SEQ ID NO: 13-14 |
| SHY12 | 12 | 95-106 cM | aroma-longipinene | SEQ ID NO: 15-16 |

Additional C. annuum plants having increased sugars, acids, C. chinense aroma, or a combination of these traits are produced by crossing a C. annuum parent plant introgressed with the desired sugar or acid QTLs described above with a donor parent having a C. chinense specific aroma profile. For example, the donor parent can be a C. chinense plant; line ZSP8T14-6274, deposited at ATCC under accession no. PTA-122300; or SVPS2625, deposited at ATCC under accession no. PTA-122296. The donor plant can also be any other C. chinense with high levels of one or more aroma molecules identified herein (e.g., α-Cubebene, δ-Cadinene, and 1,4-Cadinadiene). Breeding with a C. chinense donor parent is described in example 5.

As various modifications could be made in the constructions and methods herein described and illustrated without departing from the scope of the disclosure, it is intended that the foregoing description shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents, publications, and references cited in this specification are incorporated herein by reference in their entireties.

DEPOSIT INFORMATION

Applicant has made a deposit of at least 2500 seeds for each of pepper lines SVPS2625, SMO8T14-6275, and ZSP8T14-6274 disclosed herein with the American Type Culture Collection (ATCC), 10801 University Boulevard, Manassas, Va. 20110-2209 USA. The deposit accession numbers for lines SVPS2625, SMO8T14-6275, and ZSP8T14-6274 are ATCC Accession Nos. PTA-122296, PTA-122298, and PTA-122300, respectively. The date of deposit was Jul. 10, 2015. A deposit of pepper hybrid PS09954859 and inbred parent lines SMR 99-1275 and SMY 99-1322 was also made with the ATCC on Dec. 1, 2010, under ATCC Accession Nos. PTA-11514, PTA-11520, and PTA-11517, respectively. Access to the deposits will be available during the pendency of the application to the Commissioner of Patents and Trademarks and persons deter-

What is claimed is:

1. A *Capsicum annuum* seed, plant grown therefrom, or part of either, wherein pepper fruit at or near maturity obtained from said seed or plant or part have a pericarp comprising a total sugar content of at least 5.5%, and one or more of alpha-Cubebene at a level having a Relative GC/MS Response Score of at least 0.05, delta-Cadinene at a level having a Relative GC/MS Response Score of at least 0.1, or 1,4-Cadinadiene at a level having a Relative GC/MS Response Score of at least 0.05;
    wherein said *Capsicum annuum* seed or plant or part is *Capsicum annuum* line ZSP8T14-6274 or *Capsicum annuum* line SVPS2625;
    or wherein said *Capsicum annuum* seed or plant or part is an $F_1$ progeny of a first parent selected from the group consisting of *Capsicum annuum* line ZSP8T14-6274 and *Capsicum annuum* line SVPS2625;
    wherein a representative sample of seed of said *Capsicum annuum* line ZSP8T14-6274 has been deposited at ATCC under Accession No. PTA-122300, and wherein a representative sample of seed of said *Capsicum annuum* line SVPS2625 has been deposited at ATCC under Accession No. PTA-122296.

2. The *Capsicum annuum* seed, plant grown therefrom, or part of either, according to claim 1, wherein said pericarp comprises a titratable acidity at a higher level than that of the pericarp of hybrid pepper PS09954859 grown under similar conditions.

3. The *Capsicum annuum* seed, plant grown therefrom, or part of either, according to claim 1, wherein said pericarp comprises a titratable acidity of at least 4.2 mmol $H^+$/100 grams fresh tissue.

4. The *Capsicum annuum* seed, plant grown therefrom, or part of either, according to claim 1, wherein said *Capsicum annuum* seed is a sweet bell pepper seed.

5. The *Capsicum annuum* seed, plant grown therefrom, or part of either, according to claim 1, wherein said pepper fruit comprises a pungency of below 5 Scoville Heat Units (SHUs).

6. The *Capsicum annuum* seed, plant grown therefrom, or part of either, according to claim 1, wherein said *Capsicum annuum* seed is a hybrid.

7. The *Capsicum annuum* seed, plant grown therefrom, or part of either, according to claim 1, wherein at least 70% of the nuclear genetic material of said *Capsicum annuum* seed is from a *C. annuum* background.

8. The *Capsicum annuum* seed, plant grown therefrom, or part of either, according to claim 1, wherein less than 30% of the nuclear genetic material of said *Capsicum annuum* seed is from a *C. chinense* background.

9. The *Capsicum annuum* seed, plant grown therefrom, or part of either, according to claim 1; wherein said seed, plant, or part is a *Capsicum annuum* seed, plant, or part; wherein said seed or plant or part is heterozygous for a SMO2 QTL; wherein said SMO2 QTL is identifiable by flanking markers SEQ ID NO: 1 and 2 and is obtainable from the *Capsicum annuum* line SVPS2625, a representative sample seed of the *Capsicum annuum* line SVPS2625 having been deposited at ATCC under Accession No. PTA-122296.

10. The *Capsicum annuum* seed, plant grown therefrom, or part of either, according to claim 1; wherein said seed, plant, or part is a *Capsicum annuum* seed, plant, or part; wherein said seed or plant or part is heterozygous for a SMO3 QTL; wherein said SMO3 QTL is identifiable by flanking markers SEQ ID NO: 3 and 4 and is obtainable from the *Capsicum annuum* line SVPS2625, a representative sample seed of the *Capsicum annuum* line SVPS2625 having been deposited at ATCC under Accession No. PTA-122296.

11. The *Capsicum annuum* seed, plant grown therefrom, or part of either, according to claim 1, wherein said seed, plant grown therefrom, or part of either is heterozygous for a SMO2 QTL; wherein said SMO2 QTL is identifiable by marker SEQ ID NO: 1 or 2 and is obtainable from the *Capsicum annuum* line SVPS2625, a representative sample seed of the *Capsicum annuum* line SVPS2625 having been deposited under Accession No. PTA-122296.

12. The *Capsicum annuum* seed, plant grown therefrom, or part of either, according to claim 1, wherein said seed, plant grown therefrom, or part of either is heterozygous for a SMO3 QTL; wherein said SMO3 QTL is identifiable by marker SEQ ID NO: 3 or 4 and is obtainable from the *Capsicum annuum* line SVPS2625, a representative sample seed of the *Capsicum annuum* line SVPS2625 having been deposited under Accession No. PTA-122296.

13. The *Capsicum annuum* seed, plant grown therefrom, or part of either, according to claim 1, wherein said part is an ovule or pollen.

14. The *Capsicum annuum* seed, plant grown therefrom, or part of either, according to claim 1, wherein the second parent of said $F_1$ progeny is:
   a. a plant of an elite variety selected from the group consisting of Aleppo, Anaheim, ancho, bell, cascabel, cayenne, chilaca, chiltepin, cubanelle, de arbol, dandicut, Fresno, guajillo, Hungarian wax, Italian sweet, jalapeño, Japanese, mirasol, macho, mulato, New Mexico, pasilla, pepperoncini, piquin, pimento, poblano, puya, Serrano, and Tientsin; or
   b. a plant of a *Capsicum annuum* variety, wherein the pericarp obtained from a fruit of said *Capsicum annuum* variety comprises a total sugar content of at least 5.5%.

15. The *Capsicum annuum* seed, plant grown therefrom, or part of either, according to claim 1, wherein pepper fruit at or near maturity obtained from said *Capsicum annuum* seed or plant or part have a pericarp which comprises two or more of alpha-Cubebene at a level having a Relative GC/MS Response Score of at least 0.05, delta-Cadinene at a level having a Relative GC/MS Response Score of at least 0.1, or 1,4-Cadinadiene at a level having a Relative GC/MS Response Score of at least 0.05.

16. The *Capsicum annuum* seed, plant grown therefrom, or part of either, according to claim 1, wherein pepper fruit at or near maturity obtained from said *Capsicum annuum* seed or plant or part have a pericarp which comprises alpha-Cubebene at a level having a Relative GC/MS Response Score of at least 0.05, delta-Cadinene at a level having a Relative GC/MS Response Score of at least 0.1, and 1,4-Cadinadiene at a level having a Relative GC/MS Response Score of at least 0.05.

17. The *Capsicum annuum* seed, plant grown therefrom, or part of either, according to claim 1, wherein pepper fruit at or near maturity obtained from said *Capsicum annuum* seed or plant or part have a pericarp which comprises one or more of alpha-Cubebene at a level having a Relative GC/MS Response Score of at least 0.25, delta-Cadinene at a level having a Relative GC/MS Response Score of at least 0.25, or 1,4-Cadinadiene at a level having a Relative GC/MS Response Score of at least 0.15.

18. A *Capsicum annuum* seed, plant grown therefrom, or part of either, according to claim 1, wherein pepper fruit at or near maturity obtained from said *Capsicum annuum* seed or plant or part have a pericarp which comprises two or more of alpha-Cubebene at a level having a Relative GC/MS Response Score of at least 0.25, delta-Cadinene at a level having a Relative GC/MS Response Score of at least 0.25, or 1,4-Cadinadiene at a level having a Relative GC/MS Response Score of at least 0.15.

19. The *Capsicum annuum* seed, plant grown therefrom, or part of either, according to claim 1, wherein pepper fruit at or near maturity obtained from said *Capsicum annuum* seed or plant or part have a pericarp which comprises alpha-Cubebene at a level having a Relative GC/MS Response Score of at least 0.25, delta-Cadinene at a level having a Relative GC/MS Response Score of at least 0.25, and 1,4-Cadinadiene at a level having a Relative GC/MS Response Score of at least 0.15.

* * * * *

SEQUENCE LISTING

<160> NUMBER OF SEQ ID NOS: 16

<210> SEQ ID NO 1
<211> LENGTH: 692
<212> TYPE: DNA
<213> ORGANISM: Capsicum

<400> SEQUENCE: 1

```
gatagtgaaa tagtctttgt tcagttatta tgcgctaaaa gaagaaacat agtcccccaa      60
tcaatgtttg ttaggctggt ttaaggatcc gtaagacata gaagagcttg gaacaattca     120
caacatgtta aatcagaata agtaaatacg gatagtggaa ttgaaaatta tgataaagta     180
aaatagatat agtgattaca atgtaaatca aatgcaaagt tatgctgact tatttcccta     240
tactggattt cttgtttcct attcctaagc atggcaaatc attcatagcg cttggaaata     300
tttaacatat caattagtca acactatcta ttgtttagtg tcgccctatt caagaaggag     360
cccgtgggtg aagaggcgca caccgtagtg ccttggtttc tgcactgaag tgccacctaa     420
gcaaggcaaa gcgccatccg ctttgcacct agttacaggg gataagcgtt cctcaactga     480
gcctttaaca acagtgccat caataagttt aagttaataa tacggcaaat taatgaaaca     540
gaaatctact tcctttaaag aagttacaga gcagaaaatg acaccttaaa caaaccagca     600
tttgaatatg gggggttcta ttcagttgat ccggatattc tttgctaata ttatctccaa     660
gtctgacatt tactacgaat taatccatga at                                   692
```

<210> SEQ ID NO 2
<211> LENGTH: 394
<212> TYPE: DNA
<213> ORGANISM: Capsicum

<400> SEQUENCE: 2

```
gcaaaagctt aataccatgt gtctccagca ggatgcagat acagacaact gctgatacta      60
ctgatctgag ttattggttg aactggaggt tcttgttttg tgcaatatgg gtcttgacac     120
caacagttgc agcagtgatc attctatgga agtatgaacg atcagttaat atcatacagg     180
aatctgatag taggggggat tgccagaaaa gttctttgct tttgtatttt gacaaagctt     240
ggagaccatg tgtgaaaaga ataaacccaa tttgtttggc ggctttccga gtttctgcac     300
ttgctttact cacactagtg attgtctctg attttgttgt tcatggaggt gacatatttt     360
tctattatac tcagtaagta ttcctttat aatg                                  394
```

<210> SEQ ID NO 3
<211> LENGTH: 607
<212> TYPE: DNA
<213> ORGANISM: Capsicum
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t

```
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t

<400> SEQUENCE: 3
tgtgcacttt ggcagttgag gcccctcggt cttcataatt tctaacatct gagctgaatc      60
taaacgagca taacgcaatg gagcaactgc aaaacatctt agttgttcat aaccatagggg    120 ggaaacatat attactagag aaacagcaaa ctgttttact caggccacta attatagtcc    180
ttaccttcat gtatggcact ggtgcatctc tgagacctaa aatgttggcc aaatttgaaa    240
caattagaga tgttcaaaga gttgggtaaa atccaagcgn aaccacgggg gacttacacg    300
tagcataaac agtggactag ctcctgtaca ttatcggacg agcagccaat ctcatccaac    360
agaacaaagt agtgatttgg cctgctagtt ccctgcattg tgttttctac attatgtagt    420 gaaaaaaga ngaagataaa cgaaagngtt cctaagagga ntatgccagt gctagcacaa    480
agtcatatca aactttantg atcattctac aanagttaca tgcgtagctt cagagtcttc    540
atcagaaaag gtttgctagt aaagtactca caactcttgc cgcatgtgca cacatgtaga    600
agttgtt                                                              607

<210> SEQ ID NO 4
<211> LENGTH: 1155
<212> TYPE: DNA
<213> ORGANISM: Capsicum
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t

<400> SEQUENCE: 4
aataaggagc attgaaaatt gctgctctca aagctcctgg ttatggagat cgaaaaaggc      60
aatatcttga tgacattgct gtccttactg gaggtttgtc cataattaag ttatctcagt    120
gttcaatgaa agctatgttt acttgtatag taatttatt tttgcaatat gcattcaggt    180
actgtcatcc gagaggaagt tggtttatac ctggagaagg ctggaagtga ggtcttaata    240 tttnccctt ttcctttttt tttttttttt ttttttttc tccctccctt tcctctttct    300
tcctttcccc cctttctcc ccttctttct ttttcttt ttccttccct ccctccctc      360 ctccctccc ttcttcccct tccctttctc ccccccttt tttctttttc tcttttttt    420 ttcccccccc cctccttttc cccccctcc cttctcctct ctcccctctc cttctcccc    480 ccttccccct cctttcccct ttccccccctt tccccctttt ttttctcct cccttcctt    540 ctccctcccc ctccttcttc ttcctccctc ccctcctc cccttttttt tcccctcttc    600 ccccctttt cttttccccc tcccccctcc cttttttcc ttcccctcc cccccctcc      660 tcccccctcc cctttccccc ctttttctct ttttcctctt cccccccctc tcttcccttc    720
ttcccccctt ttccttttcc cctttttttt ccccctttt cttttcttc tcctcccctc    780
```

```
tccctctntt cttccttctc tcccottcct tttcctttct ttttcttttcc cctctttctt    840 tcccttccct ccccccccct ctttctcctt ccttttcccct cttccttctc tctccttctc    900
ttcctcctct ccctcccctc cccctcttct ccccttttc tcccccccc ttttctcccc      960 ccctctcct ccctcctctt cctctcccct ttcttctcc ccccctctcc cttttttttt     1020 cttttcccc tcttttctt cccttttccc tttctccccc ccccctctt cccctctccc    1080 ccccctccct ccctcttctc cttttctttt tctccctct ctccccctc ccctctcttt   1140 ccttttattc ctctc                                                   1155

<210> SEQ ID NO 5
<211> LENGTH: 1416
<212> TYPE: DNA
<213> ORGANISM: Capsicum

<400> SEQUENCE: 5
gtgtcaaaat ctccatttga gtcttgaaat agttggtctt tgcagagtca aaagttcact    60
tcacaagctc taatactctc tcgactactg taagcaatat taccaagctt cttgtaaaac    120
atgaaactgt gaactatcct ctttatacgt agacgtgatg aactttctca gactaataat    180
tggtttaact ggtgttacta tgattagttc ccttctataa tacatttcag gatcattcct    240
aactgatcat tattttttca ggttgtccct tcaatagcta ttgcttttgt gacatatgag    300
caagtgaagg acctattggg agttgagatc aggatatctg attgatgaag acaggctcca    360 atgttttttcc actgcatacg ataattttgt aggcaaggat agatagagtg ataataacat    420
ggcgggttac cccgtctaaa cagagaattt acgattctgt tttagcttgt gacagaaagt    480
ttaggacttt ccagttgtgc ttataattcc ctatgtattt gcttattcca tattgtcaat    540
aagcaaaatt tacaacagtg taatgactaa tttgaatgtc ttgctatggt tcaagtgaag    600
aaaagctgat tgctggttgc ctttgctaat cctggtctcc attgtacttg tggtcgaatt    660
tttctggcgt cttcaccagt tttcagctct ctttttttca ttggaaaaag ttgaacagtt    720
taggtaagaa aaggggtact cactcatgat ctagtgtatt ctgtaatgcc attttgtatg    780
ttctgattaa tatgacgtga atcgtttctt ttaagaaaat ttgggttgct atgatgtatg    840
ctgtctactg aactgcttta tccgctggag ggctaaacat tttactacct tgcaaagtag    900
gtgagtgttc ggtatgtgta atggatgaaa atcaatgggt ttgagctcga aatgggcaa     960 cacttgacca gataaattta gactagttga atcaatgatt ttcggatacc agaagcaaaa   1020
gaaaaaaaaa gagttggcat ttgcaaaaga gtgatcaatt ctacttctag tactactctt   1080
ttacatgtat gttttcttga aaggtttgaa tgctacacct caacgatcta tctctcttgc   1140
actcacactt gatgcgaaaa acatactat gaaaggtagc ttctatggcc ttgctggaaa   1200
ccttcttttg gtacatttct tgctgctagc tttgctggat gttgatttct tcacatttt   1260 ctgcaatgcc tgaatcaaaa gatgaatcat cttgctggta aaaggaaatg aacttttact   1320
attaacacaa tcaattagta ttaattttgt gctcctgtcc aaaaaaagaa tggcatgatg   1380
tcaaaacatc taattttcta aggtcctaac tcgtac                             1416

<210> SEQ ID NO 6
<211> LENGTH: 2246
<212> TYPE: DNA
<213> ORGANISM: Capsicum

<400> SEQUENCE: 6
ggagaacacc aagcatcagt aattttaaca aataatcgag tctaaaatat ctggtaataa     60
```

```
tgatcaagtc cataacacca ctaaaggagc tatgttgtac ttaatagtag ttaaagtttg      120
ggttcatctc acacaggatt gctaatttca acagttttcc ttgttaatat aaaacctaag      180
cgcctcagtc gacatccaac cagccaaaag gtctgttcat gaatctagac tgcaacttaa      240
aagtaactaa cacatgagca acacaatctt acgctcgcac tcagatcaat caacatgaat      300
gagcaatcaa caaacttaag gtactattcc tgtaaaaaaa cagaaataag cacttttcg       360 cttctctttt ttcccttgta aaatgtatac aggaatgcgg acatatatca tcaatcacat      420
gcaaccaatt tcttctttga tagaagttct aaaatttgta ttttataaaa atgaaagtct      480
tgcaccttaa tgatcttaaa tcactccatt gcctgttaga tgaactccat tttcatgtta      540
tgcagatctc ccagacacat cacaaccatt gaaaaataat caagtttgag tactgtttaa      600
acttggtaaa acatagaatg gagcatcagg atatgcacca tgaagtgttg aagccttct       660 gattcaggtt caactttacg agatatttga ttctcatgat gagtcctggc gttcatcatg      720
tcgagggcct tttgatataa agaggccaaa tgtggcgaga gcccatccaa gttactggag      780
tctacatcaa gattggctcc ctgttctgct tcccaagcct gaatgcgag gagagttgaa       840 cttagatcag caagagggac agataactgg cgatggaata aattcctaat tcgctggaca      900
tgcttctctc tcgactgcat tacaatgaag caaatatcaa cagaaaagat caactatcaa      960
atgtggaaaa gataaaaaca gatcaagtta tcattggaca ttgtctaata tagaaacacc     1020
aatgatacat caatcttctt tacacaaaaa tacagaacag gctataattg agcgaagttt     1080
tagatctaac attctttgat cttcagcaca gatactaata gtatagacat cgttttgaaa     1140
ccaaaacctc tgacctaaaa ttcaagccac agctcaacta actgaaatta ctaaaaatca     1200
atacgcagtt tcttgccatt aactcaacca aataattaaa tagaatattg tgcaaagtgc     1260
aaactcataa cacaagagag aacaactcaa tatgcgtttt ccttttcatg gtcttcattc     1320
aataagggaa gtaaggtttt cccatcattt aagtttcata acatttcaat ctgctaccag     1380
ttgttgaagt atgcttatct aaaaaggaaa gaagtatgct tgtctaaaag gaactccaat     1440
actaagtcat atcagtctca tgacagtaaa agcaaccaaa gcatttgagg tacacctctt     1500
cttcgtatct gttcctgatc tcttgacagt caaacaacga gacgaggtta acccatttaa     1560
gttcttttgg gaaggggtgg gagtgaaaga tgcttcagag gaacaacaag aagatgcagc     1620
agcaactttt taccatccca tgcttaaacc caaggggtac gctaaaagcc agtaaagtct     1680
cagaaaaagt gatttgagag cactataaga tgaatagtca cgagctccgc aaagacacaa     1740
ctcatgatat agagtactac cttcccaggg aattatattt acgagaattg aacaaagaca     1800
tgttacatta tgcctctaaa ttctctcatg cttccaggga agaaacagg gacaggaggt      1860 gatatacaac ctaacggaaa aagatatatt ccacctttcc atcatcctgg aggaatagga     1920
cggcacaacc ttagaaaaac aagtgctaag ctaaaaaaag aacggcatct agctctttga     1980
caatacgaac aacaacatct cagtctcaaa ctagatacag ctagctctta ctatatcttt     2040
aaaaaggcta aagtgacaac ggcatgcatc ctaggaaaga aagagaagca ccaagctctt     2100
acattggcat cagtttcatc aatagtgagg aaaatagctt gttcaaattc cctatataat     2160
tcccatatcc tgctgccttc agcaacatgc aaaccagtag caaccagggc acgctcaaag     2220
agatttcttg ccttttgaaat tccagc                                          2246
```

<210> SEQ ID NO 7
<211> LENGTH: 725
<212> TYPE: DNA

<213> ORGANISM: Capsicum

<400> SEQUENCE: 7

```
ggctgtagtt ggagatatca tagtgacttg acttgcaaca tatttcccat gtctcaactt      60
accaagcatc caggccaaag aagcagggtc actagactat tatcaaatta actctagttt     120
ttctcagtat acaaagattt catcagagca tctcctactt tcaataggtc atgaactaga     180
ttagagttgc tctcgacgaa tccataagtg acgccatttt tcatcgggcc gtataacgac     240
caaagatctt gaccaaccga tccaaacaac tcaaagatta ataaatgtat cgttaatctc     300
ttcatactcg aggtaccatt tgtacaaaca aaaatcccct tcagtcacgt ggtttcttct     360
tcatacaaat agacaatagt agttataatg caacattgaa gtacattttg tgctaagatc     420
ccattatcct gaaccgatct taccagggca tttgctcatt gccagagaga cgtagcaata     480
aacgtacata caccaacaaa gtaaacaacc cagctcatgt tatctataaa taaccttatg     540
acacaaaaca tattcatcat catcggctat ttacccacag aattaatatt ctcaaaacag     600
attaaagtca tcactgggta tcaccagtca ttcccgccaa agcctaatag tcgtttgtta     660
agcatattga ttacttttca caaccaccta atactacaca ttcaattaac atcagaaata     720
caacc                                                                 725
```

<210> SEQ ID NO 8
<211> LENGTH: 455
<212> TYPE: DNA
<213> ORGANISM: Capsicum

<400> SEQUENCE: 8

```
gcgttttcgc agtttgcagt tgcattatgc gtattctccc aaccttccca agagcgaact      60
tccaccttca gctttaaaga aaatcctttg ctgtttttat cagaagctgc ataagttgc      120
ataagctcta gtatgtaaac tctaacatgg ttggggagcc gaaagttttc agagaactct     180
tccaatctct cccaaactgc ctgcctgaca ctctgcagat gatccaagtc accagctaat     240
ttgctcaaag atgacaagta atagtgtaga cactgatgct cacgggattc gtcagtcaac     300
tcctgcaaga tggtcttcaa tatactaagg tagagatctc gaagattctg gatgctgaaa     360
gcttcttttt taaagtccgc caccgatcca gcttcacgct ggaaatgagc catgacttca     420
tcatatatat ctgcaaccgc tcgaaagcaa caacc                                455
```

<210> SEQ ID NO 9
<211> LENGTH: 357
<212> TYPE: DNA
<213> ORGANISM: Capsicum

<400> SEQUENCE: 9

```
gaatatttta aaaatcaagc aagaactcaa ctcaagtatg ttcttccggg gttggatatt      60
tcacatgctt gaccagttga catgttgaat tctgtggcat tgtcatctga tttaataaac     120
aatatgggtt tctcttctcc atgcccactc ttttgcattt tgtgtacttc aattcaagga     180
tccatctttt gcatcttcag gtcaagacat aggcgggagt gcaaagttac cactaacacc     240
aacaccacct ccgagtggtt tgacatcaaa tccgttgcca acaactgaac aacaaagaag     300
cccgcatgga catgcagttg caccggccat tgctggtaaa gctaccccta aaccatc        357
```

<210> SEQ ID NO 10
<211> LENGTH: 515
<212> TYPE: DNA
<213> ORGANISM: Capsicum

<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t

<400> SEQUENCE: 10

```
gcagctgaat tctaaaaaag agctgagctt gggacaattc aaagagacaa gatcgttaag      60
gaagtccaga gcagctgaat tcacatattt tacctgtgga gcatgtccat tagagtctga     120
gacagatgta agattactta gattatggat ttttttttgt tgctcaatga tgcattgctc     180
tcgctctttt tgtgatcttc tctcctcctc caactccatg gcaagcttct ctcgctctaa     240
ttcgtactaa taaatgaaga gtaagcagtc ataagccatg tcaacacaag ataagatcag     300
tcttcttctc ttaacaaaan caagaaaaat agtaatgata attaccgtna gtaggtcatt     360
tctgagtttt agtatctctt gctcaagcac ctcggaatgt gatccctgtg taggaggttt     420
catcccatat aagatatttt tatgcaactt atgaatatat aaatcctgag agacaagaca     480
ctcacctgaa gtttcatgcg tagttccctc aattt                                515
```

<210> SEQ ID NO 11
<211> LENGTH: 1905
<212> TYPE: DNA
<213> ORGANISM: Capsicum

<400> SEQUENCE: 11

```
gaagcaatag aaaatattgt ctctttagca aaaaagttac ggggcagatc tggtaaggaa      60
attcatgcta ctctaatagt ggttttaata tcacgttcaa accacggatc ccatttaagt     120
gttcgcatct gtcaataccet ctctctagat ttaatataaa aagttgttgt atatgaaaca     180
tctgaacata attttcaaga ctggttaatc tgattaaaat atgccttgtg tccaaaactc     240
ctatagcaca ttcatgtttg ataccacaat ggccaggaat attcttcctt aacgtaatta     300
tatcaggttt tcctgcatga taagggactt gacttctgag gacttcgatg tgatatttgg     360
ctcccctcgc agcataacaa tcgattttgg gggaactcta ggcgttgagt ttgtttagat     420
tttaggtttt agtacagcag cgtattgatt tgattgtca ttggtatttg ggtacttatt     480
aacatgggaa gatccgttga gttactttgt gatggaaggg atgggtattc tgccgtggga     540
gcaacccact ggtggtgttt accgtcatcg ccgccaatag ttttctaagg ttttatggta     600
ttattattga ttccgttcaa gtaacactca caatagtcat attgctactt aaaagttaa      660
atagtctcta tgtactaatt tatatgatgc agctaaattc aaaattcaaa tagagatttt     720
tgaaatgggg cgaaggaagt gttgaattta tgttcatttc atcaaaacct ctaatttttt     780
gttttcaaaa ttactaaaat ccacataaag aaaagatgtt ttgactctag tatttgaac      840
atttcacata aagttggata attaactggc tctcgaattg taatttgtta ttagttgcca     900
gcaaacaccc tcttcctta ggacttccct tttcctccta gcagccactg gtaaaaagtt      960
attcatatta ggtgtttcaa tcaagcaaat ggatacatga tatgatattt gtttatattt    1020
acataattat tacttaatca cagtatttt atgcattttt tacttattta attataacaa    1080
acatcgatat gactaaatat ttatcgatac cacacagtca tacattttat cagtttgaaa    1140
atttactcaa attaataata ggccaaaagg aaaaggtaaa attgatggat ttgagcaa      1200
atggctaggg cctcttctta atatacccttg attgtactat tcaactctgt gtaacttttt    1260
```

| | |
|---|---:|
| tgaaagaaaa aaaacggtaa gtttccctat gaattcaata ttgtttttttt aaaagaaata | 1320 |
| cattatattt cccaaaaaaa atcaggagga aaataaatta ctaaaatagt tctttcataa | 1380 |
| ttaatttgaa gttcatatgc atataaccag agggaggaga gggggaggg ataggttgg | 1440 |
| tcgaggggc tcatcagaac cttcttagat agaaaattac cttgtttgta tatgtttaaa | 1500 |
| ttatttttta tgtgaaactc ctttgataag tatcagacat aataagcttc ttaatttgtt | 1560 |
| caataactat atatattata agtcacatag gctcttcaat cagtacataa taacattata | 1620 |
| tatatgattt gaataccatc caaatcaaac tatagattat aacataattc ttattaagca | 1680 |
| attaatacac ttttaaggat aatcattgtg cctaggtgat ggtccagtag aaattggaac | 1740 |
| tcctttggt ggcaatggaa ccaattattc ttgtgaacga aattctttct ttcaatcgtt | 1800 |
| gtatttagaa attggttctg agaattttga gattggttca gaaaatttcg aaactggctc | 1860 |
| tgaaaatttg aaactaggtt caaaaatatt tcgaaacttc tgaga | 1905 |

<210> SEQ ID NO 12
<211> LENGTH: 2405
<212> TYPE: DNA
<213> ORGANISM: Capsicum

<400> SEQUENCE: 12

| | |
|---|---:|
| gagttactat ttcttcccta aatagtcaaa atgatatctt tgggatgttc ggttattcct | 60 |
| gtatgtgtta cttaaaagca ccttaagttt gccattaatt tctcacaact tcttggagaa | 120 |
| tattgtaaat tgtttcatat gattttaggt gttgatggaa gcattattat tgcagatggg | 180 |
| aaaccgcgac cttgttttca ctgcttttg gagggatttg cttcgctgga aggttcacat | 240 |
| tgttttctca cttttgctga ttcatgttcc gcttttgtta ttatcatgat tagtaaccccc | 300 |
| ttgttaagaa ccaatgacta caagtatgct ttgcttttaa aaatagtttg atccatgaag | 360 |
| gtttagtgca tcttgtaaga gaaggttgag ggaaattgtc tacaaaatag atgctctgac | 420 |
| atgcttccat attcatatga agaatggtct aatttcaaat tgaactcttt gctctgtgac | 480 |
| cttcctctgt gctttatggc tccttaattc tttgttacat ctgaaaaact atactcatca | 540 |
| aaagtaaaac gaaatataaa catctgaaga aaaacttgtt ataaccccca acttttctt | 600 |
| ccctattcaa agataggatg ccatctgctt cactaaatac tcacattgtg tgtgaaattc | 660 |
| atttcatgta aatggatttg ctcttttcaa ctgttggtaa agtaaaacgt tgctaaataa | 720 |
| tggcaaagca atatcttgtg ccctggatat tttatactcc acagttaacc taatcgttgt | 780 |
| tctcttccac atggaagaac aattcctttc ctttttgaaa aacaatacat gattttcatc | 840 |
| tttagaaaat tgcgaaagta acacattttc taattttgtt tagccagcga actattggag | 900 |
| cagttaacgc tgtccttgtg tttggaatca tcgcttcttt cacagctctt gtggtaatt | 960 |
| ccattcttga ttcagtagaa aaaaactgct attattatct ttaggataat gtagctgttt | 1020 |
| tacatttttac ttttagggtg cagtattgat attcatcttt gtggacagta attttcgtat | 1080 |
| ttcactgaaa ttggtgccat cgtatctgac tcatgccaat atatgcctca attggtgaca | 1140 |
| ccaacatagg atagctgccg cctgaattat ttagatggcc tggagtctgg ggactttaaa | 1200 |
| tgttagatgt tgcatgggat ggtaaatgct tcctgccaac aggtttggcc agtgggggt | 1260 |
| ccaaaaatta aatggtaga tatgaaaaaa gtgaattact tcacatagta ctacatgcat | 1320 |
| attagattgg tagatgatta tttcattcat ttgaactttt taatgctcgg agatgcttag | 1380 |
| ctttgtttct tgttatttat gccatagaca tgatatttct tacttttccat gagtgcagac | 1440 |
| cttttctgat gaatttcttc gaaaggacat taatagaatt tctatttgag atattggatg | 1500 |

```
atttagtaaa tggttcgtcc aacaggtttg cttaatggaa gttcctgaag ctacatctgg      1560
tgttacatgt aaaagaagtg ataacttcaa atgggccact taataggaac gttatgttaa      1620
taatggttat tggctaagat gagcttctta atagatatgg tctgctttat ttgtcctttg      1680
tacgtgctat atgcatgaca aaaaggattc aatacattcc catacatctc gtgaagacca      1740
acaaaccaag gttctaagta atgcacatta aaagaatgtt cattgagata cttgcatgag      1800
atggtaaatg ttcatgtcaa caggttttcc taatggcagg tcgtgaggca tatgagtatt      1860
acattggtag atgattattg gtgcatttgc ggttcttaat gcttatactt gatcccagtt      1920
atttgatgtt tatatacgct atacagataa aggatttaat ataatctcat acatcatgcc      1980
aagaccagaa aacaagtgat gtttcaaata acaaatttaa atattcaatg gcaaatttgt      2040
gccaatatta atctatatct tggaaacaca tgcgtcaagc ttcatgtaat gcactggaaa      2100
tggttgagag agaaatctta atatctcatc ttttacgctt aaggttgttg ccagtggaga      2160
cttgcattgg gaggctcttc tgaaagctaa ttttgaagct gttactcaaa gtatacccat      2220
aatcgcactt tcttttgttt atcaggtaac aagtgttcct gatcaactca tatagtcgcc      2280
ctgggattgt gcatctaagt taatcacttg cttttcaatc gcagaatgtc gtacctgttc      2340
tctgcacaaa tcttgaaggg gacctgtcaa aagtaaggtg attatcagta tcttgcttgc      2400
attac                                                                 2405

<210> SEQ ID NO 13
<211> LENGTH: 696
<212> TYPE: DNA
<213> ORGANISM: Capsicum
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t

<400> SEQUENCE: 13
tttctaagcc agagaatgtc ctcttgattg ctccttcact ctcattccac tctacaaggt        60
gggattcacc ttctttactn gtaccacaag agaaaagtct gaaagaagat cagaaaagtt       120
aaaaatgact agatataaaa tcaaatgcaa acaagtttgt attgcttctc aaaaaagttc       180
gtcttctttc agacatcaat cataaaatcg cgtaggcctc tttacaattc attttctac        240 cttcaataag caccattaan tcattcacta ttgctgccat atnttttatc ctggcacctt       300
ttgagtataa aactcacccct aatgagtcct cctccaacgg ngtcatattt tgccttaggg     360
agtgtgcata actttagccc tttttttattt tttggccaac ggtatgtttg atagagtgcc      420
```

| aaagaaggtt gttagagaga gcacactttt atttatttaa aaatgttttt caacacacna | 480 |
| tctcaagtcc gtcttaatct tttttcacga atcaagcgca tggaaattct ctttgatagt | 540 |
| gagtgactca agacctntgc taccatgttg aagggtatga tcatctcatc caacaactta | 600 |
| agctagacag aaacttttat atatttaatc atgtcgttca acaaagaaac cgaaattaga | 660 |
| gctaatagga ggaagaccac tgataaaatc acaaac | 696 |

<210> SEQ ID NO 14
<211> LENGTH: 1314
<212> TYPE: DNA
<213> ORGANISM: Capsicum

<400> SEQUENCE: 14

| aactgtaata tcattctcct ttatggtatc ttttcatca tctacaattt gagttggtga | 60 |
| aactggcaat gatagtactg attcaatttc tttatcttgc gatgatgttt gtattattaa | 120 |
| tggagttggt ggtggagatg gtaatgacaa ctttggtagt gacgttattg gtggttccgg | 180 |
| ggctggtagt gttactatat ctgtttgcat ttctgatgct ctctccctca aaggcttccc | 240 |
| ctgatgatct aattgtggaa ttctacgttt gcttttttctt gcacaatttc taactgcttt | 300 |
| cgaatgtata ccaagttctt ctccaatcgt agttctgatt actcttttat ctcttgtctc | 360 |
| agatgaagaa ggatcctgga tgttcttgtt cccagaagaa acattcaagt aggacgatgt | 420 |
| tctttcttct ttgcctttgc gtacaaagta agatgcactc cattcttgta cctatttgta | 480 |
| acataatata attaagtagt taaaagtgta ttctagatct ctttaataac ttacgctttt | 540 |
| agatgaaatg atcacaaact tcaataatac cttgatagct aaatttgata tagaaccgga | 600 |
| acttgttgaa aacgctgata ggttgctatc ttttccatga gtattactaa actctgctaa | 660 |
| cagttttttgt cgattaatct ctttggacga atcagtaagt cctttgtaat atggacttct | 720 |
| tggagagtat ctcttttctt cttgaatcac atttcttttg ttgaattcct tcacattatt | 780 |
| agctgttaag ctcctcgagt tctttgaaga cgaacttccc tttcttccct catcgacttt | 840 |
| tttagcccat gttggtttca ctgagtcagc tgaatatgtt gatctgactg taggggtat | 900 |
| tatgagtgaa ttttgagttt ctgatatcct gcagggaaca gattttgaac gtgggatcga | 960 |
| cattgaagag ctgagattga aagttgctgt tttttttttt ttcctttttgt aggatattat | 1020 |
| aggatcaata gagaactatg gaatttaaca caattaatat gttaatgtg aatgggaaaa | 1080 |
| aaagagtttc ggttatttta ccatttgttt gttgttgttg ttgttactgt ttccatatct | 1140 |
| gttaccatgt ttcttcactg tcgctttcc tgtttgtact ttctttgatt tgctctactc | 1200 |
| gagtcgtggg tcctccaaga acagtctgta aggtctgcgt acgctctacc ttctcccgac | 1260 |
| ctcacttgtg aaatttcatc gaatgtgttg ttgtaatgtg aatggaaaag aagc | 1314 |

<210> SEQ ID NO 15
<211> LENGTH: 747
<212> TYPE: DNA
<213> ORGANISM: Capsicum

<400> SEQUENCE: 15

| gaagaagctg ccagagctta tgatgttgaa gctcggagga tcagaggcaa taaagctaag | 60 |
| gtaaactttc ctgatgaagc tccagttcct gccccaaggc aagctgctaa ggtaaatcct | 120 |
| gagaaggttc tttctgatga gagttccaac ccagttctgt ccgacaccgc gttaatgaat | 180 |
| ttgactgatg gatgttgcaa caacctgggc ttttttgaag agaaaacgaa aaaactgtat | 240 |
| ggctataaag ttttgcgcac tactactgta aatatgggac ctaactcata tgtccctcca | 300 |

-continued

```
cctgctgctg gtgtttactt caattctgac caaggaagta actcatttga cccctccgac    360
tttggttggg gagaaacgtg ttccaggact ccagaaatat catctgttct gtcagctgct    420
atagaatgtg atgaaactca atttgttgaa ggtgccgatg tggaggtgaa cctaaaatct    480
tgttccaaca atttggtgcc cgatgatgga aacactgcta acaagccacc tgaagaattt    540
ccagcttttg aatcccagat gaagttcttt cacaccccat atccggaagc aaattgggat    600
gtatcagttg atgctttcct taacgcagat gcatctcagg gtggcgaaaa tgctgtggac    660
ctttggtcca ttgatgaact ttcttcttta atgagaggtg tctactaagc taagaatgcg    720
ctatgtgaat aaggcttcac atgagtt                                         747

<210> SEQ ID NO 16
<211> LENGTH: 833
<212> TYPE: DNA
<213> ORGANISM: Capsicum

<400> SEQUENCE: 16
gattggaaat atatgaagaa ggggaattac agtggcaatt caagggaatc atatcaatcc     60
ttcactaata atcaatctca tggaagattt gatagatatg gacatcaggc tgctggtcaa    120
tccaataatc agttttcagc tcataacttt actgggagtc aatcaggaga ggatacaggt    180
ttagcagttt catctagcag tcaagggagc aaggacatca acaatgctat gatagccaag    240
gcacaaggct tctcagatga agagtacgta cagacaaatc atgtcattac taaataaaga    300
tgcacatgat tccaaacagg tcaacatgtc aggcatagtt acttgtttat caacacatgt    360
tccacatgaa tgggtaatag attctggtgc cacataccat gttgcagcac ataaaggtgt    420
cttctcacac tgtcataaga tatttacaca gaaaatgata tggtgaatct tcctactgga    480
gccaaggcag atatctcaca tgttggagaa gcacagatta taaatgatga aattgttaga    540
gatgtgatgt ttgtccctga cttcaaagct caatctattg tcagtgtcaa aaatgactaa    600
agaactttca tgctttgtat cattctatcc cgatttctgt gtatttcagg accttcacac    660
tggcaaggtg aagggattg gtaaggagaa aagaggatta tacatcctta agaaggtctg    720
tggattgaat gatatacatg aaggaagttc tcaaagttg ctggttgcag aagtagatat    780
gcaagactgc aacttatgcc ataggaggct tggacaccct tcttcttagg ttc            833
```